(12) United States Patent
Schyler et al.

(10) Patent No.: US 7,126,126 B2
(45) Date of Patent: *Oct. 24, 2006

(54) COMPACT CONSCIOUS ANIMAL POSITRON EMISSION TOMOGRAPHY SCANNER

(75) Inventors: David J. Schyler, Bellport, NY (US); Paul O'Connor, Bellport, NY (US); Craig Woody, Setauket, NY (US); Sachin Shrirang Junnarkar, Sound Beach, NY (US); Veljko Radeka, Bellport, NY (US); Paul Vaska, Sound Beach, NY (US); Jean-Francois Pratte, Stony Brook, NY (US); Nora Volkow, Chevy Chase, MD (US)

(73) Assignee: Brookhaven Science Associates, LLC, Upton, NY (US)

( * ) Notice: Subject to any disclaimer, the term of this patent is extended or adjusted under 35 U.S.C. 154(b) by 380 days.

This patent is subject to a terminal disclaimer.

(21) Appl. No.: 10/687,797

(22) Filed: Oct. 16, 2003

(65) Prior Publication Data

US 2005/0082486 A1 Apr. 21, 2005

(51) Int. Cl.
*G01T 1/164* (2006.01)
(52) U.S. Cl. .................. 250/363.03; 600/407; 600/436
(58) Field of Classification Search ........... 250/363.03; 600/407, 436
See application file for complete search history.

(56) References Cited

U.S. PATENT DOCUMENTS 4,864,140 A    9/1989  Rogers et al.
5,793,254 A    8/1998  O'Connor
2005/0113667 A1*  5/2005  Schyler et al. ............... 600/411
2005/0167599 A1*  8/2005  Schyler et al. ......... 250/363.03
2005/0215873 A1*  9/2005  Peter ........................... 600/407

OTHER PUBLICATIONS

J.-F. Pratte, et al., "Design of a Fast-Shaping Amplifier for PET/CT APD Detectors with Depth-of-Interaction", *IEEE Transactions on Nuclear Science*, vol. 49, No. 5, pp. 2448-2454, Oct. 5, 2002.
Paul O'Connor, et al., "Prospects for Charge Sensitive Amplifiers in Scaled CMOS", *Nuclear Instruments and Methods in Physics Research*, Section A, vol. 480, pp. 713-725, Mar. 27, 2002.

(Continued)

*Primary Examiner*—Otilia Gabor
*Assistant Examiner*—Christine Sung
(74) *Attorney, Agent, or Firm*—Lori-Anne Neiger

(57) ABSTRACT

A method of serially transferring annihilation information in a compact positron emission tomography (PET) scanner includes generating a time signal for an event, generating an address signal representing a detecting channel, generating a detector channel signal including the time and address signals, and generating a composite signal including the channel signal and similarly generated signals. The composite signal includes events from detectors in a block and is serially output. An apparatus that serially transfers annihilation information from a block includes time signal generators for detectors in a block and an address and channel signal generator. The PET scanner includes a ring tomograph that mounts onto a portion of an animal, which includes opposing block pairs. Each of the blocks in a block pair includes a scintillator layer, detection array, front-end array, and a serial encoder. The serial encoder includes time signal generators and an address signal and channel signal generator.

33 Claims, 45 Drawing Sheets
(1 of 45 Drawing Sheet(s) Filed in Color)

OTHER PUBLICATIONS

G. De Geronimo, et al., "Front-End Electronics for Imaging Detectors", *Nuclear Instruments and Methods in Physics Research,* Section A, vol. 471, pp. 192-199 (2001).

P. Vaska, et al., "Effects of Inter-Crystal Cross-Talk on Multi-Element LSO/APD PET Detectors", pp. 1-3, Apr. 19, 2002.

A. Kriplani, et al., "Comparison of Experimentally Measured Light Output with Monte Carlo Simulations from LSO Crystals", pp. 1-2 (2001).

C. Woody, et al., "RatCAP: A Small, Head-Mounted PET Tomograph for Imaging the Brain of an Awake RAT", *Elsevier Science,* pp. 1-4, May 2003.

P. Vaska, et al., "RatCAP: Miniaturized Head-Mounted PET for Conscious Rodent Brain Imaging", pp. 1-2 manuscript received May 16, 2003.

S. Shokouhi, et al., "System Performance Simulations of the RatCAP Awake Rat Brain Scanner", pp. 1-2, Oct. 2003.

B.J. Pichler, et al., "A 32-Channel LSO Matrix Coupled to a Monolithic 4×8 APD Array for High Resolution PET", Abstract, *Proceedings of 2000 IEEE Med. Imag. Conf.* (2000).

G. De Geronimo, et al., "A CMOS Fully Compensated Continuous Reset System", *IEEE Transactions on Nuclear Science,* vol. 47, No. 4, pp. 1458-1462, Aug. 2000.

P. Vaska, et al., "Imaging the Unanesthetized Rat Brain with PET: A Feasibility Study", *IEEE,* pp. 1569-1571 (2002).

S. Shokouhi, et al., "A Non-invasive LSO-APD Blood Radioactivity Monitor for PET Imaging Studies", pp. 1-5, Nov. 10, 2002.

S.R. Cherry, et al., "MicroPET: A High Resolution PET Scanner for Imaging Small Animals", *IEEE Transactions on Nuclear Science,* vol. 44, No. 3, pp. 1161-1166, Jun. 1997.

S. Shokouhi, et al., "a Non-invasive LSO-APD Blood Radioactivity Monitor for PET Imaging Studies", pp. 1-2 (2002).

S. Shokouhi, et al., "A Non-invasive LSO-APD Blood Radioactivity Monitor for PET Imaging Studies", pp. 1-2 (2003).

A. Villanueva, Jr., et al., "Spatial Resolution of a Noninvasive Measurement of the Arterial and Venous Input Function Using a Wrist Monitor", pp. 1-2, Oct. 2003.

J.F. Pratte, et al., "Front-end Electronics for the RatCAP Mobile Animal Pet Scanner", pp. 1-2, Oct. 2003.

P. Vaska, et al., "Imaging the Unanesthetized Rat Brain with PET: A Feasibility Study", pp. 1-2, Apr. 20, 2001.

P. Vaska, et al., "Imaging the Unanesthetized Rat Brain with PET: A Feasibility Study", *IEEE,* pp. 1569-1571 (2002).

A. Chatziioannou, et al., "Performance Evaluation of microPET: A High-Resolution Lutetium Oxyorthosilicate PET Scanner for Animal Imaging", *The Journal of Nuclear Medicine,* vol. 20, No. 7, pp. 1164-1175, Jul. 1999.

P. van Zant, "Chapter 5: Overview of Wafer Fabrication", *Microchip Fabrication,* 3rd edition, pp. 99-118 (1997).

P. O'Connor, et al., "Low Noise Charge Amplifiers in Submicron CMOS", 5th International Workshop on Front End Electronics, pp. 1-21, Jul. 2, 2003.

P. Vaska, et al., "A Practical and Competitive Alternative of Mega-Crystal PET: A Miniature Anger Detector with LSO and APDs", Jun. 2001.

C. Woody, "New Detectors for PET Imaging of Small, Awake Animals", Instrumentation Seminar, pp. 1-50, Mar. 12, 2003.

"Scanning Lab Rats as they Scurry", Popular Mechanics, p. 22, Aug. 2003.

"Electronique Du Scanner Pet", Oct. 2002.

* cited by examiner

Energy Spectra for Crystal 20

Individual Serial Links

Common Serial Bus with Busy

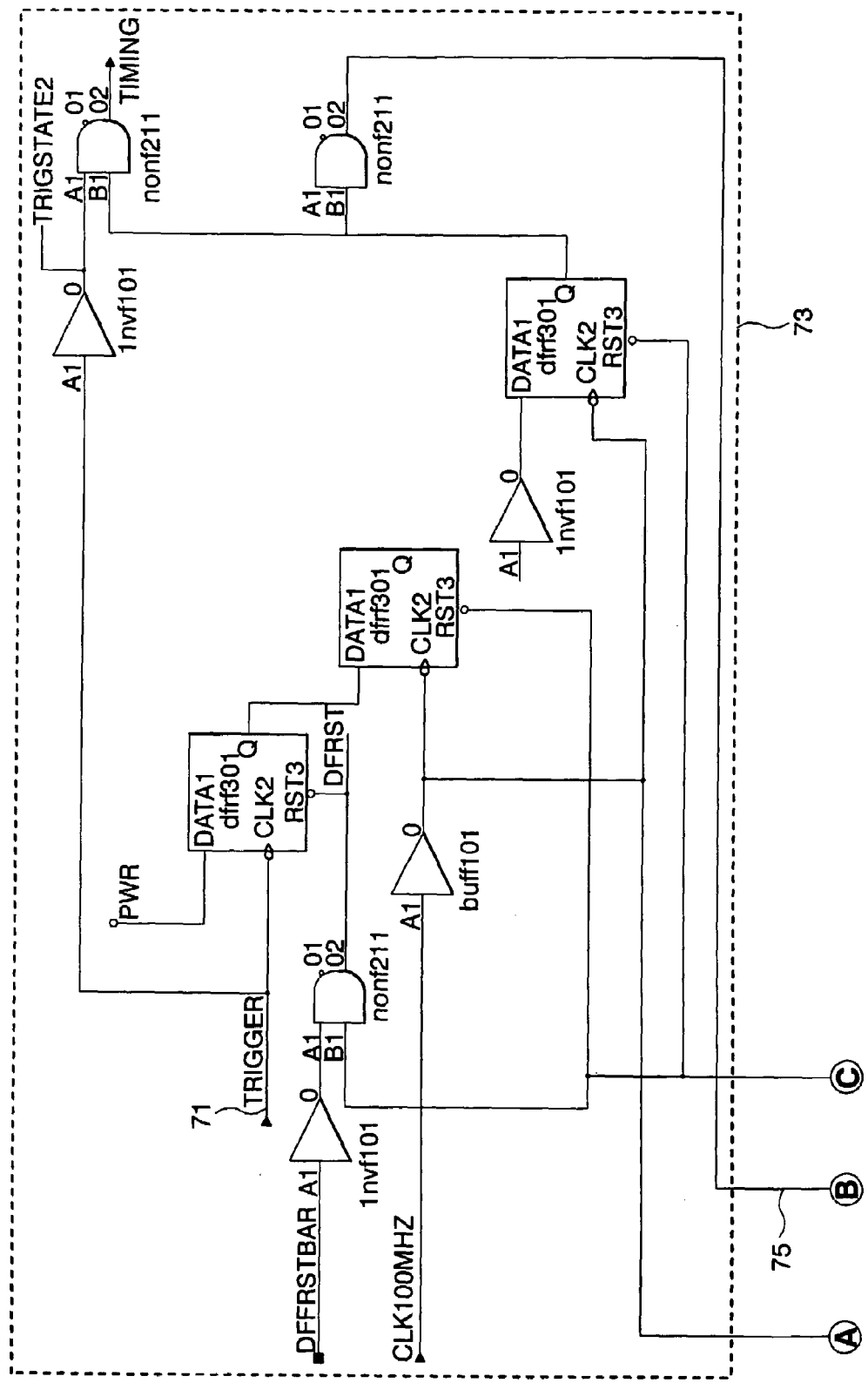
Figure 19a(1)

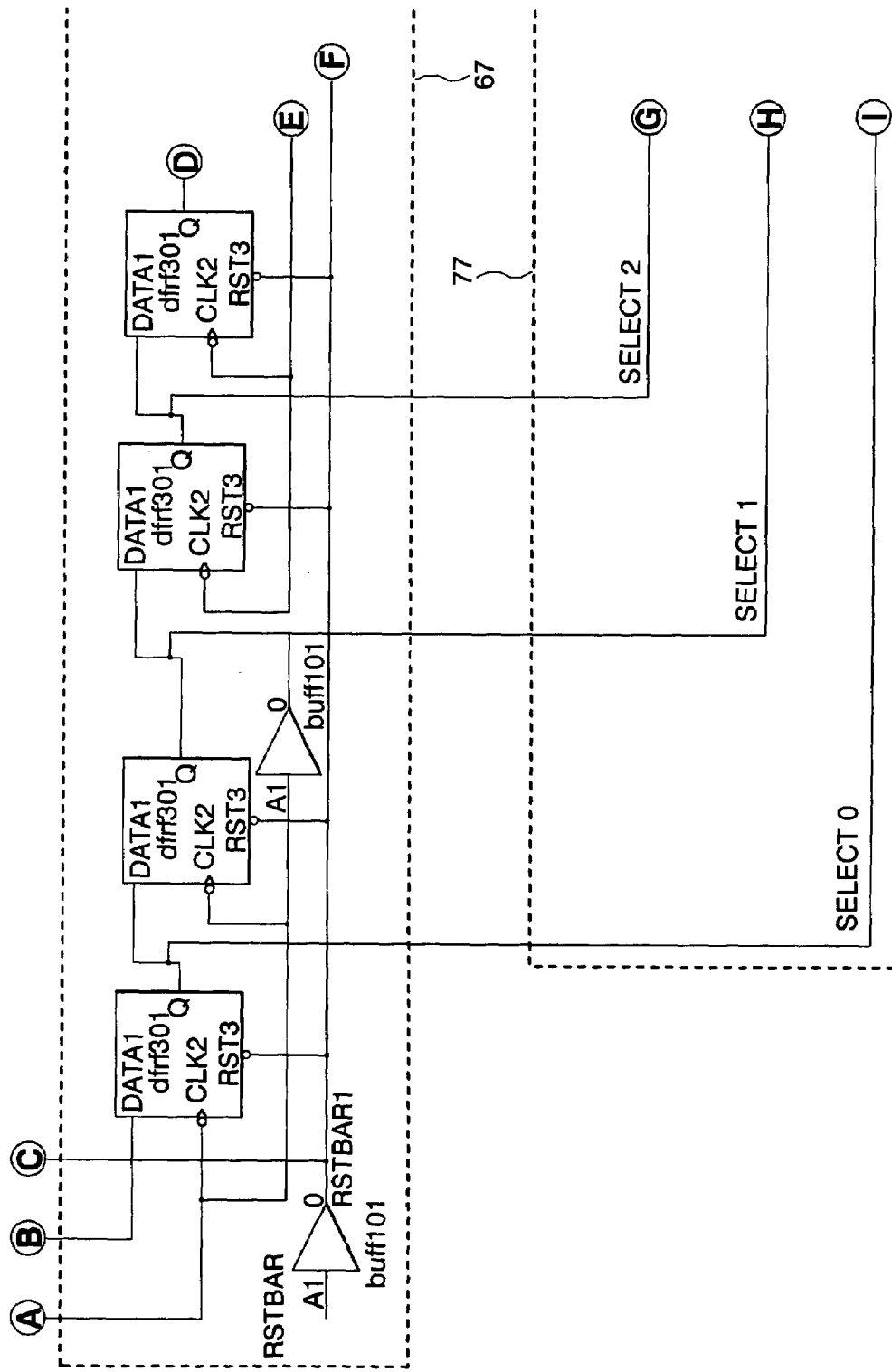
Figure 19a(2)
TRIGGER=Asynchronous Trigger
A[4.0]=5 Bit Crystal ID from the 32 to 5 Priority Encoder
SERADD - serialized 5 bit Crystal ID at 100MHz

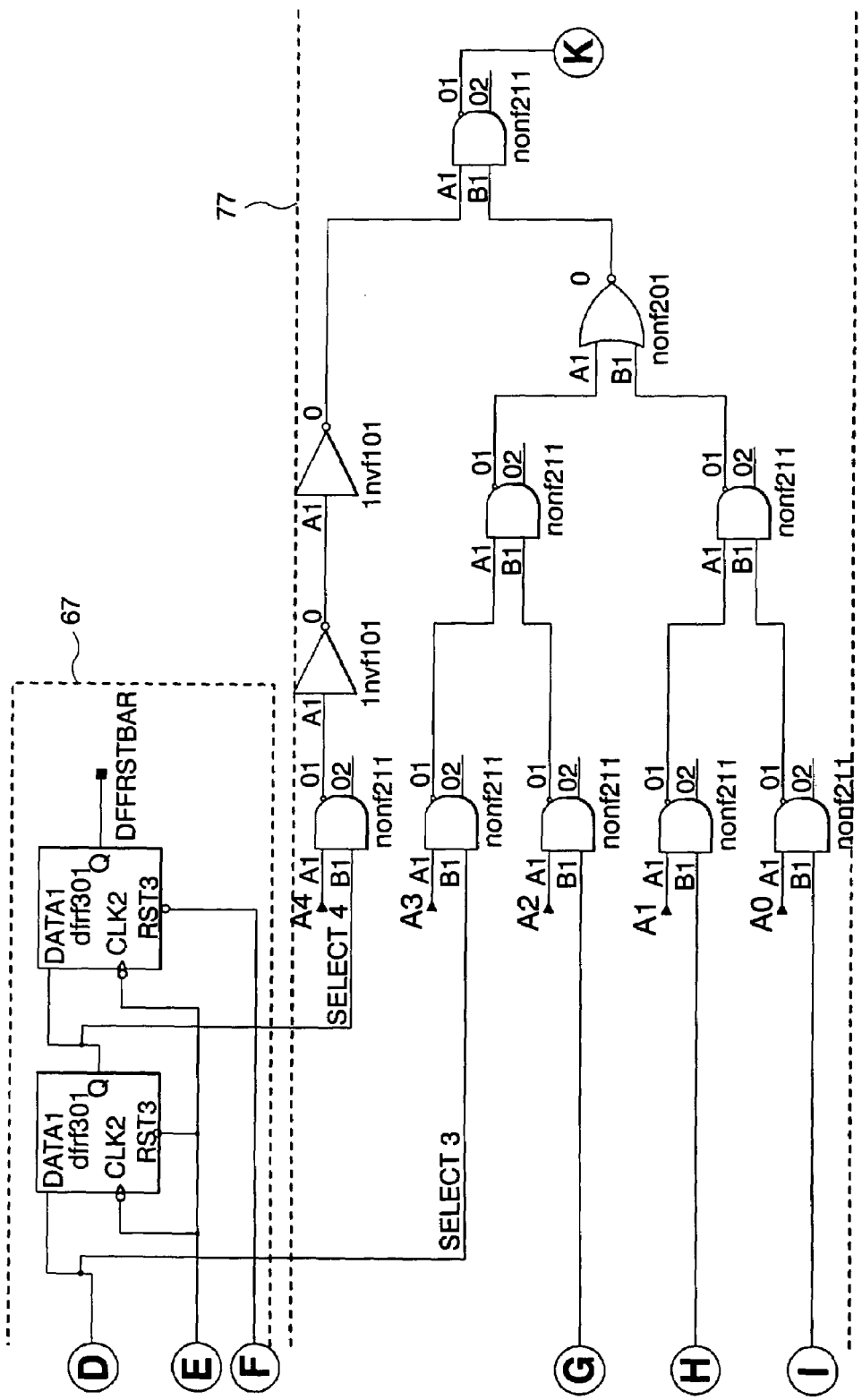
Figure 19a(3)

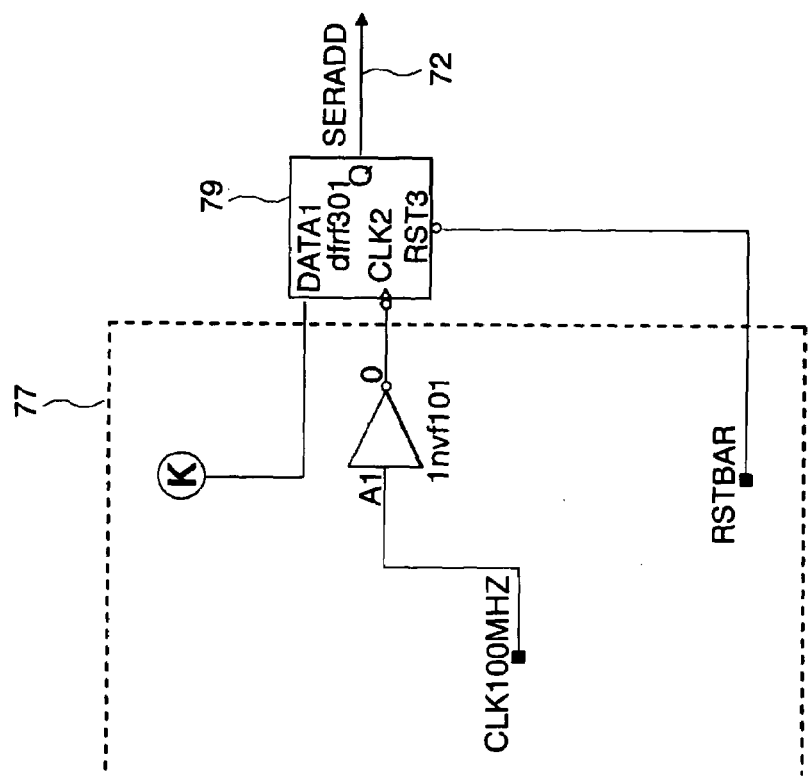
Figure 19a(4)

COMPACT CONSCIOUS ANIMAL POSITRON EMISSION TOMOGRAPHY SCANNER

This invention was made with Government support under contract number DE-AC02-98CH10886, awarded by the U.S. Department of Energy. The Government has certain rights in the invention.

BACKGROUND OF THE INVENTION

1. Field of the Invention

The present invention relates to positron emission tomography (PET) scanners, and more particularly, to low-power, low-noise front-end electronics in compact conscious animal positron emission tomographs for use in imaging portions, such as the brain, of conscious animals.

2. Description of the Prior Art

Positron emission tomography (PET) is a non-invasive imaging technique that uses radioactive isotopes to map chemical or metabolic activity in living organisms. PET is commonly used to diagnose and monitor cancers, brain disorders and disease. It has also been an important research tool for investigating chemical and functional processes in the areas of biochemistry, biology, physiology, anatomy, molecular biology, and pharmacology. While traditional radiography and three dimensional imaging techniques, such as x-ray computed tomography (CT) and magnetic resonance imaging (MRI), provide structural information, PET scanning provides physiological information of metabolic activity leading to biochemical changes that generally occur long before the associated structural changes can be detected by the more traditional imaging techniques.

Positrons are positively charged electrons emitted by the nucleus of an unstable radioisotope. The radioisotope is unstable because it is positively charged and has too many protons. Release of the positron stabilizes the radioisotope by converting a proton into a neutron. For radioisotopes used in PET, the element formed from positron decay is stable. All radioisotopes used in PET decay by positron emission. The positron travels a small distance, which depends on its energy, before combining with an electron during a so-called "annihilation". The annihilation of the positron and electron converts the combined mass into two gamma rays that are emitted at 180° to each other along a so-called "line of coincidence". These gamma rays are readily detectable outside the human body by the detectors of the tomograph. The coincidence lines provide a detection scheme for forming the tomographic image.

Several radioisotopes are commonly used for PET including $^{11}C$, $^{18}F$, $^{15}O$, and $^{13}N$. The radioactive isotope that becomes a source of gamma rays for PET is first chemically incorporated into a compound forming a "tracer" of chemical or metabolic activity, which is then administered to the patient, typically by injection or inhalation. Compounds naturally occurring in the body are most useful for monitoring metabolic activity. Such compounds include glucose, oxygen, water, nitrogen, or ammonia. One common use of PET is to pinpoint which areas of the brain are used to perform a particular function. The technique uses a naturally occurring compound as a radioactive tracer. For example, when a subject is injected with a form of radioactive glucose, the glucose is delivered to the brain through the bloodstream. Since glucose normally fuels brain activity, the more active a part of the brain is during some experimental task, the more glucose it uses and the higher concentration of glucose in that part of the brain is revealed in the generated PET image.

Pharmaceutical drugs can also be tagged and administered, so that the drug itself is used as a tracer to determine the pharmacokinetics of its interactions in the brain or other body sites. PET scans can then provide in vivo repeated static measurements at a given time interval, or even dynamic measurements of the efficiency and distribution of the drug over time. Such measurements have been extremely useful to quantify the performance of a drug using a non-invasive technique. Such studies are becoming a more routine portion of testing used in the development of new, particularly psycho-active, pharmaceuticals.

Analogously, the phenomena of drug addiction has also been studied using PET. For example, PET images of drug addicts are compared with those of normal subjects. Such studies may make use of tagged neurotransmitters to examine the changes in receptor densities (numbers) or receptor binding affinities that result from long-term drug abuse.

Like other clinical imaging scanners, the typical PET scanner consists of detectors surrounding the subject to be imaged. The detectors are coupled to a scintillator, which converts gamma rays to light photons. The light photons are then converted into electrical impulses. Each electrical impulse generated at a detector corresponds to an "event", or the arrival at the detector of a gamma-ray photon that originated at an annihilation within the subject.

Common prior art scintillator materials for gamma-ray detection include sodium iodide crystal, bismuth germinate (BGO), and barium fluoride ($BaF_2$). The common prior art detectors include photomultiplier tubes.

The simultaneous or "coincident detection" of a pair of annihilation gamma rays by two detectors locates the line of coincidence along which an annihilation occurred due to chemical activity in the body. The detectors communicate with a central processing unit (CPU), at which a tomographic reconstruction technique is applied to generate or "reconstruct" a spatial mapping of the chemical activity in the body from a superposition of multiple lines of coincidence obtained from the entire array of detectors. Reconstruction of images from tomography data, using techniques such as filtered back-projection, is well known in the art and is described, for example, in A. C. Kak and M. Slaney, *Principles of Computerized Tomographic Imaging*, IEEE Press (1988), which is incorporated herein by reference.

In a typical PET scanner, each detector communicates with the CPU via independent data links, each of which is dedicated to a particular channel. The detector area commonly limits the spatial resolution obtainable in the reconstructed tomographic image. Therefore, to obtain good spatial resolution, it is not unusual for a PET scanner to be comprised of thousands of detectors with an equally large number of corresponding channels and data links.

One area of research that has benefited tremendously from the use of PET technology is medical research on the effects of pharmaceuticals in treating various diseases, cancers and drug addictions. For most of these types of studies, animal models must be used in place of human subjects, for obvious ethical reasons. PET imaging of animals, however, poses some problems. For example, in order to eliminate motion-induced artifacts from the PET image, it is necessary to immobilize the animal using an anesthetic. Unfortunately, anesthesia profoundly disturbs the neurological state of the animal, complicating the interpretation of PET results. The present state of the art PET scanners and methods of using PET have not addressed the problem of how to perform positron emission tomography on a conscious and awake animal or how to perform positron emission tomography on an awake animal while the animal performs some task.

In addition, human patients whose health management may benefit from the information provided by a PET scan are not always compliant with the requirement for maintaining a fixed position. Non-compliance may arise as a result of the very disease indication for which the PET scan results could usefully address, e.g. Parkinson's patients. Non-compliance may also arise in patients that are unable to understand the necessity of remaining in a fixed position, such as in children and/or the mentally disabled. The present state of the art PET scanners and methods of using PET have also not addressed the problem of how to perform positron emission tomography in human patients that are unable to maintain a fixed position, i.e., in a moving subject.

OBJECTS AND SUMMARY OF THE INVENTION

It is an object of the present invention to provide a method and apparatus for acquiring positron emission tomography (PET) images of the chemical and metabolic activity of a conscious animal and/or moving human subject.

It is another object of the present invention to provide a method and apparatus for performing PET studies on animals used for medical research and on non-compliant human subjects, without administering anesthesia.

It is yet another object of this invention to provide a method and apparatus for allowing an animal and human subject freedom of movement to perform tasks during a PET scan.

It is a further object of this invention to provide a method and apparatus that utilize low-power consumption front-end electronics for generation and serial encoding of pulse signals from annihilation information for use with a conscious animal PET scanner.

It is yet a further object of this invention to provide a compact, low power consumption Application Specific Integrated Circuit that includes the front-end electronics for data encoding to be used with a miniaturized wearable PET scanner.

It is still a further object of the present invention to provide a method and apparatus that utilize improved timing resolution and selective shielding techniques to effectively reduce random coincidences and detector cross-talk.

A method of serially transferring annihilation information from sequential events recorded by detectors on a detector block in a conscious animal/moving human positron emission tomography (PET) scanner used to image a portion of a conscious animal or moving human, which incorporates some of the preferred features of the present invention, includes the steps of inputting a first time pulse on a detector channel corresponding to a detector in a block array, and generating a first time signal representing a time-of-occurrence of the first time pulse from a first event. The first time pulse is asynchronous to a clock signal.

The method further includes generating a first address signal, which is synchronous to the clock signal, and which represents an address identifying the detector channel where the event was recorded. Additionally, the method includes generating a first detector channel signal, which includes the first time signal and the first address signal. The method is repeated for sequential events, and a composite signal comprising the sequential detector channel signals, collected from detector channels in the detector block, is generated and serially transmitted over a data link.

An apparatus to serially transfer annihilation information from sequential events recorded by detectors on a detector block, in a conscious animal/moving human positron emission tomography (PET) scanner used to image a portion of a conscious animal or moving human, which incorporates some of the preferred features of the present invention, includes a time signal generator associated with each detector channel, and an address signal generator and a detector channel signal generator for each block. The time signal generator inputs a first time pulse on a corresponding detector channel, which includes a position in time representing a time-of-occurrence of the first event. The time signal generator generates a first time signal representing the time-of-occurrence of the first time pulse and the first event. The first time pulse is asynchronous to a clock signal.

The address signal generator generates an address representing the detector channel at which the first event is recorded, and a first address signal that includes the address. The first address signal is synchronous to the clock signal. The detector channel signal generator generates a first detector channel signal that includes the first time signal and the first address signal, which represents the detector channel at which the first event is recorded. The detector channel signal generator generates a composite signal that includes sequentially recorded detector channel signals from the detector channels and serially outputs the detector channel signals over a common data link.

A compact positron conscious animal positron emission tomography (PET) scanner for acquiring images of a portion of a conscious animal, which incorporates some of the preferred features, includes a ring tomograph which further includes at least one pair of blocks, in a ring configuration. The blocks in a pair are arranged opposite each other on the ring tomograph, and each block includes a scintillator layer, a detection array, a front-end array, and a serial encoder. The front-end array and serial encoder are preferably implemented in a single Application Specific Integrated Circuit (ASIC). The scintillator layer preferably includes a plurality of crystals and outputs light photons in response to an event originating from an annihilation within the animal. The detection array includes a plurality of detectors and outputs a detection signal in response to detecting the light photons.

The front-end array includes a plurality of front ends and outputs a time pulse in response to receiving the detection signal. The serial encoder includes a plurality of time signal generators corresponding to the detector channels, an address signal generator, and channel signal generator for serially outputting a composite signal, which incorporates sequential events recorded at a plurality of detectors on a block, over a common data link.

These and other objects, features, and advantages of this invention will become apparent from the following detailed description of illustrative embodiments thereof, which is to be read in connection with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 19a is a schematic diagram of a preferred embodiment, which is implemented in an ASIC, of the serial encoding circuitry shown in FIG. 19.

FIG. 32b is a linear intensity profile plot through the center of FIG. 32a.

DETAILED DESCRIPTION OF THE PREFERRED EMBODIMENTS

A compact conscious animal positron emission tomography scanner of the present invention addresses the need for imaging of metabolic or chemical activity of conscious animals, especially rats. Rats are commonly used as animal models in medical research because it is possible to genetically alter rats to isolate a specific trait, and to follow the trait through generations. The knowledge gained in these animal models can then be applied, for example, to human disease, cancer, drug research, and drug addiction.

An additional embodiment of the compact positron emission tomography scanner of the present invention includes the adaptation of the apparatus and methods of the present invention to the imaging of non-compliant moving human subjects.

Figure 1:
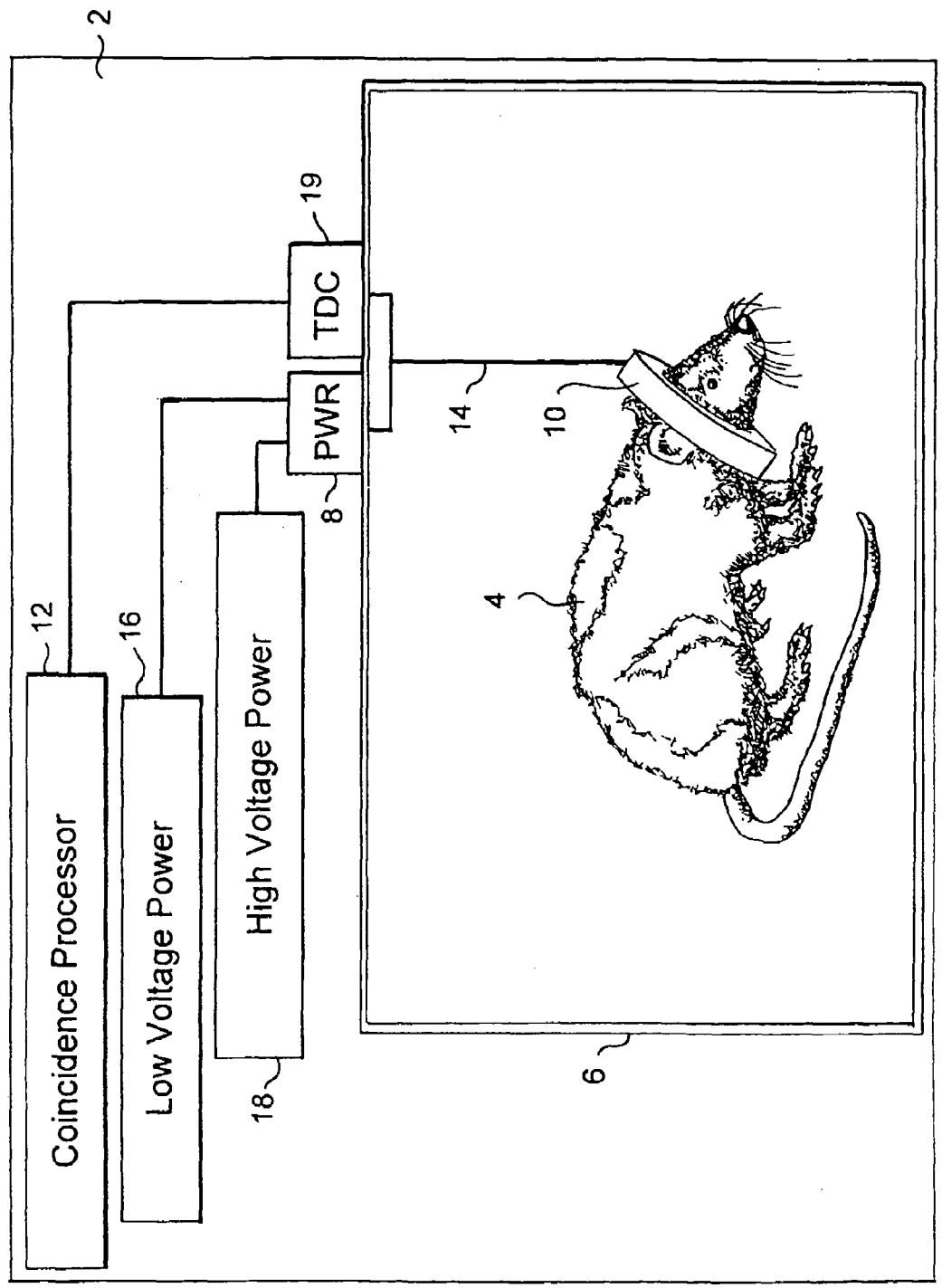
FIG. 1 is a block diagram of a preferred embodiment of the invention, which is a compact or miniaturized head-mounted PET scanner for conscious rodent brain imaging, appropriately named "RatCAP", for "Rat Conscious Animal PET".

The method and apparatus formed in accordance with the present invention provides positron emission tomography (PET) images of chemical and metabolic activity within a conscious animal. FIG. 1 shows a block diagram of a preferred embodiment of the invention, which is a compact or miniaturized head-mounted conscious animal PET scanner 2 for conscious rodent brain imaging. A head-mounted ring tomograph 10 for use on a rat has been appropriately named "RatCAP", for "Rat Conscious Animal PET".

Figure 13:
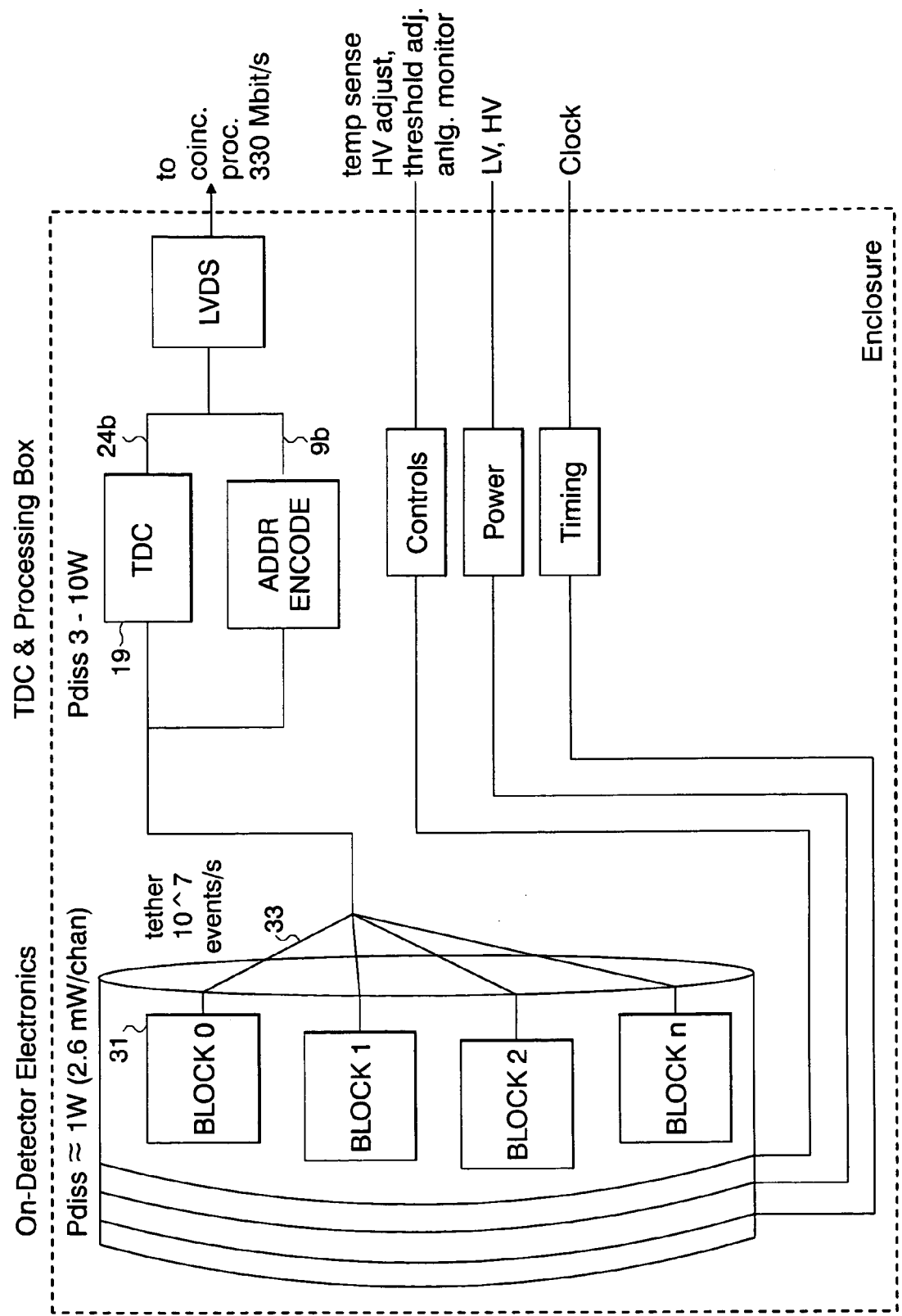
FIG. 13 is a block diagram of the read-out electronics for a conscious animal Positron Emission Tomography (PET) scanner.

Referring to FIG. 1, the conscious animal positron emission tomograph (conscious animal PET) 10, which mounts directly onto an animal, is also referred to herein as a ring tomograph or a detector ring. The ring tomograph is mounted to the head of a rat 4 in FIG. 1 and preferably includes scintillator and detector arrays to record gamma-ray events resulting from annihilations within the rat, and front-end electronics for converting the gamma rays to electrical pulses and encoding the annihilation information. Processed signals, including the electrical pulses from the detector ring 10 with encoded addresses, are preferably transmitted via an attached detector cable or tether 14 to a Time-to-Digital Converter (TDC) 19, which adds time stamp information. The tether 14 includes a separate data link 33 for carrying annihilation information for each block, as shown in FIG. 13. The TDC 19 is preferably mounted on an animal containment system 6 housing the animal 4. Also mounted on the outside of the animal containment system 6 is a power input unit (PIU) 8 for supplying both High Voltage (HV) 18 and Low Voltage (LV) 16 power from the respective power supplies, via the tether 14, to the electronics resident on the detector ring 10.

The TDC 19 shown in FIG. 1 preferably detects the time-of-occurrence pulses, corresponding to an "event", with a resolution of about 1.3 ns. An "event" is defined as the arrival at a detector of a gamma-ray photon that originated at an annihilation within the subject. The TDC 19 then translates these asynchronous timing pulses into digital information, such as a time stamp, and transmits the coded digital information including a detector channel address, to a coincidence processor 12. A high speed data acquisition system (not shown) preferably collects and stores the data for further processing. PET image maps of brain activity are preferably reconstructed from the data processed by the coincidence processor 12 using reconstruction and image processing techniques well known in the art.

Figure 2:
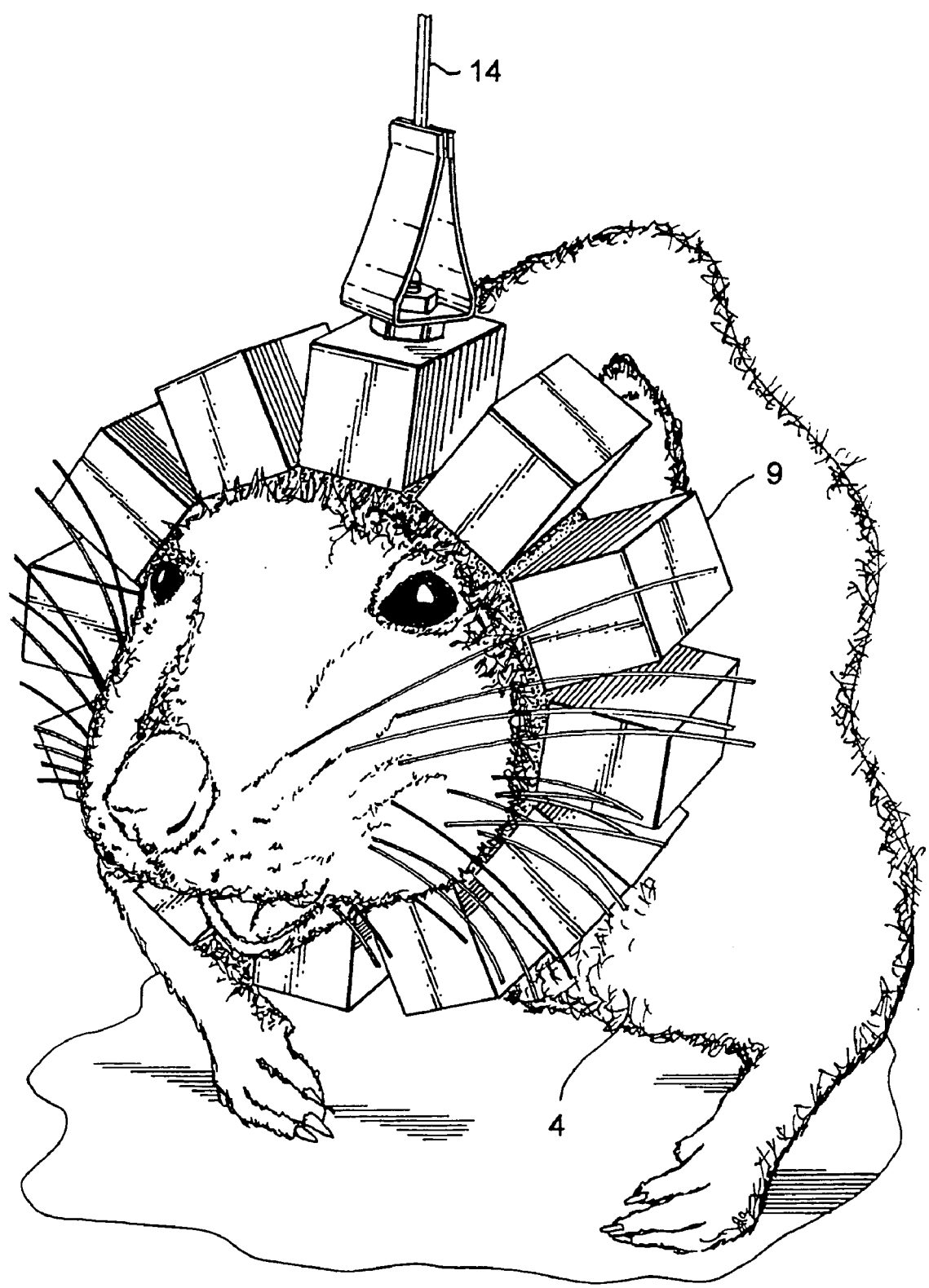
FIG. 2 is a pictorial representation of a rat wearing a mockup of the conscious animal PET formed in accordance with the present invention.

Referring to FIG. 2, a preferred geometry of the conscious animal PET 10 is a full ring septa-less tomograph that fits between the eyes and ears of the rat 4, positioning nearly the entire brain within the field of view. The ring slips easily over the head of the rat and fits between the eyes and ears. This places nearly the full rat brain within the field of view (FOV) of the detectors and also allows the brain to be centered in the transaxial FOV with sufficient clearance below the head for a substantially normal posture. The scanner may alternatively be rigidly attached to the skull with standard techniques commonly used for mounting microdialysis probes into the rat brain.

In addition to small-animal PET requirements of high spatial resolution and sensitivity, the present invention satisfies several practical structural conditions required for a wearable miniaturized PET. For example, the weight of the assembly attached to the animal is preferably minimized so that normal activity is not inhibited. In addition, the entire tomograph, excluding the inner portion of the ring, is preferably encased in a protective cover 9, which may consist of a thin layer of plastic or a metal casing. Therefore, the compact tomograph formed in accordance with the present invention is lightweight, durable, directly mountable to an animal, and rugged enough to withstand scratching and pawing by the animal.

Figure 3A:
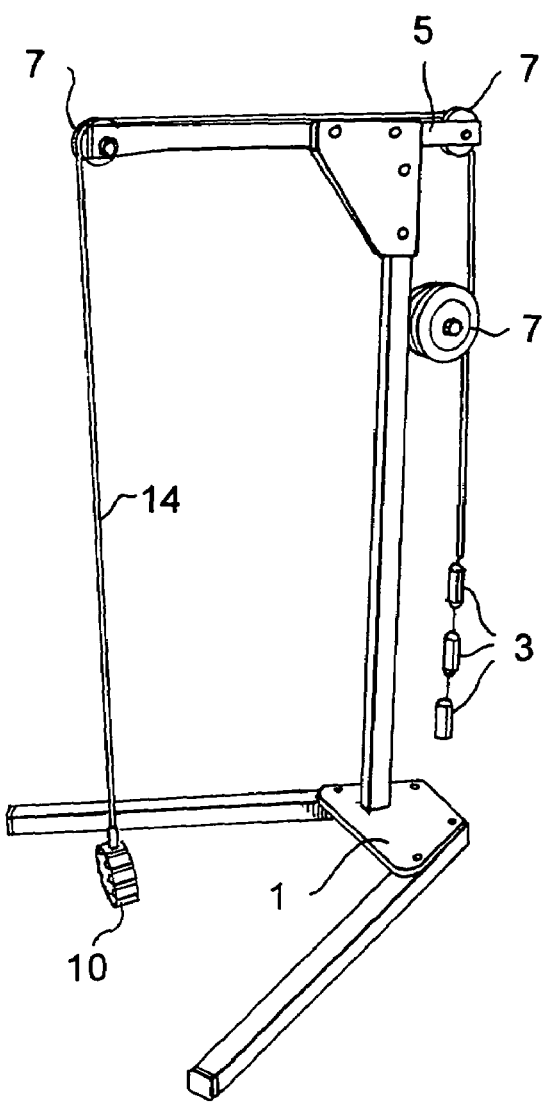
FIG. 3a is a pictorial view of a suspension support stand, with the PET scanner attached.

Referring to FIG. 3a, it is advantageous to counterbalance the weight of the scanner and dampen the inertial motion of the detector 10 as the animal moves, in order to prevent motion-induced artifacts in the PET images and to minimize stress on the animal. In a preferred embodiment, a suspension support stand 1, as shown in FIG. 3a is used. A tether 14 is preferably attached on one end to the ring tomograph 10 and on the other end to a counterweight 3. The tether 14 preferably hangs vertically from a pivoted arm 5, and is guided over the arm by two small grooved wheels 7. A third grooved wheel 7, attached to the side of the suspension support stand 1, further guides the tether 14 along a vertical direction to the attached counterweight 3. The pivoted arm 5 is preferably attached to the stand 1 as shown.

Figure 3B:
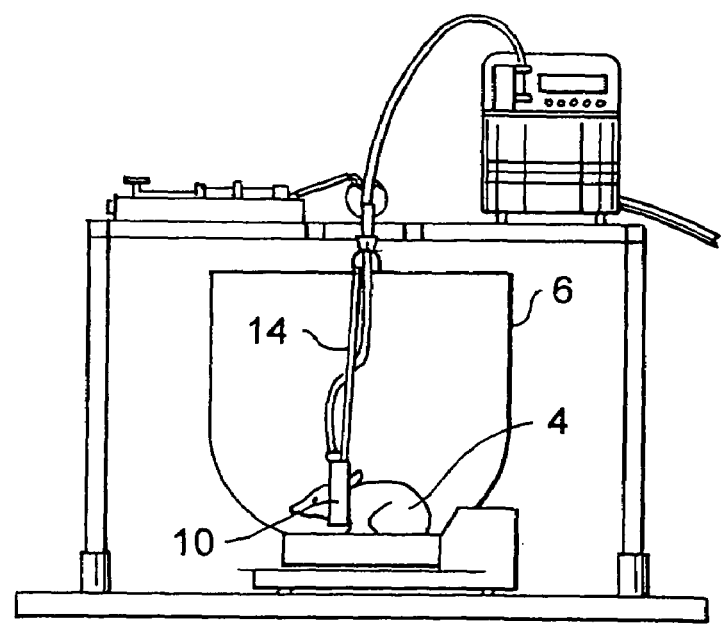
FIG. 3b is a pictorial representation of the suspension support system used within an animal containment system that allows freedom of movement.

The suspension support stand 1 is preferably used in conjunction with an animal containment system 6, as shown in FIG. 3b, to allow the animal freedom of movement to perform experimental tasks while wearing the compact ring tomograph 10. However, the size and mass must still be minimized to allow a normal posture and permit the animal to overcome the inertia of the scanner assembly.

The present invention minimizes the weight and size of a compact PET, so that the suspended ring tomograph 10 weighs only about 125 g. In addition, the size of the head-mounted ring tomograph 10 for a typical laboratory rat, weighing about 250 grams, is 4 cm diameter with an axial extent, or axial field of view of 2 cm. Tolerance of a rat to the weight and size of the tomograph formed in accordance with the present invention was tested with excellent results; the rat moved about with modest effort and did not appear to suffer excessive stress.

Figure 4:
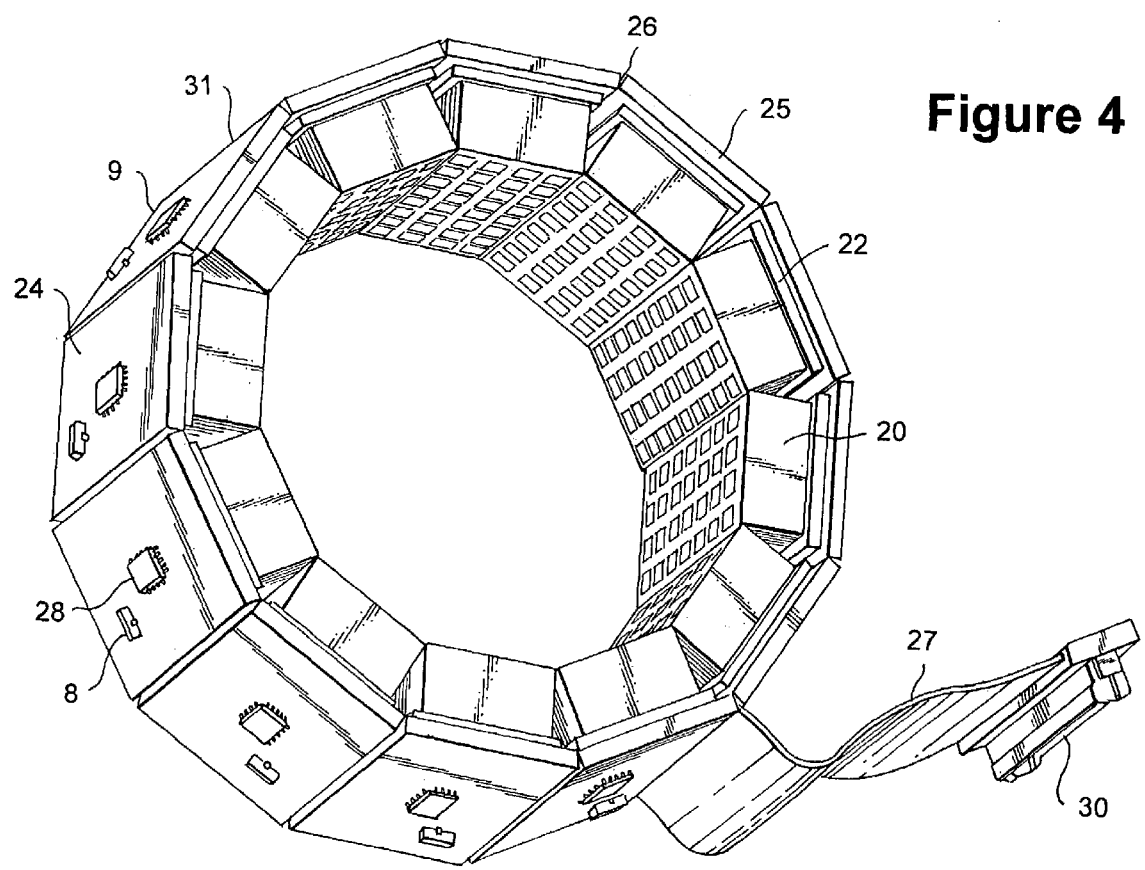
FIG. 4 is a perspective view of the conscious animal PET, showing ring geometry with a preferred configuration of scintillator and detector arrays.

FIG. 4 illustrates the compact ring geometry and a preferred configuration of the detectors in the scanner 6 formed in accordance with the present invention. There are preferably twelve (12) blocks 31 arranged in the ring configuration. Each block 31 includes a two-dimensional array of scintillators 20 disposed on the inside of the detector ring 10, toward the rat 4, as shown in FIG. 4. Each block 31 further includes a two-dimensional array of detectors 22 coupled to a scintillator array 20. The detector arrays 22 are preferably located on the face of the scintillator arrays 20, directed away from the rat 4. The detector arrays 22 are preferably mounted onto a rigid printed circuit board 24. The circuit boards 24 corresponding to the blocks 31 are preferably connected via a flex cable 26. The entire tomograph, excluding the inner portion of the ring is preferably encased in a protective cover 9, such as a thin layer of plastic.

Referring to FIG. 4, for each block 31, there is a second corresponding block 31 that is located directly opposite the first block 31, for coincidence detection. The front-end electronics, for recording, filtering and encoding the electric pulses representing gamma ray events at each detector, are preferably mounted on the back of each rigid printed circuit board 28, away from the animal. An external cable 27 is preferably attached to detector ring 10 for transmitting the annihilation information to external electronics and a remote processor for image processing and reconstruction. The external cable 27 also provides high and low voltage power to the detector ring 10, via the PIU 8.

Figure 5:
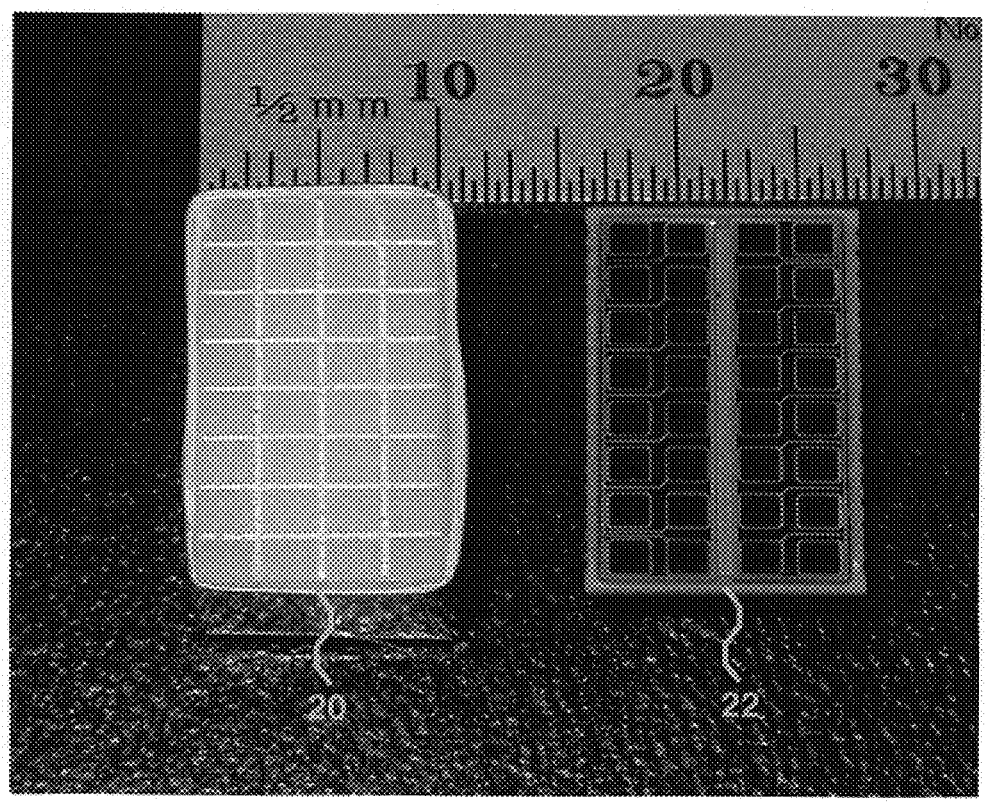
FIG. 5 is a pictorial view of a scintillator array and a corresponding avalanche photodetector array.

In one embodiment, each block 31 is comprised of a 4×8 array of lutetium oxyorthosilicate (LSO) crystals 20 of about 2 mm×2 mm square area and 10 mm depth, which have optimum characteristics for PET. These LSO crystal arrays are available from Proteus, Inc., Chagrin Falls, Ohio 44022 and CTI. Inc., Knoxyille, Tenn. 37932. Instead of position-sensitive photomultipliers (PSPMTs) used in prior art small animal PET designs, the present invention preferably utilizes a 4×8 array of thirty-two (32) avalanche photodiodes (APD) 22. These arrays are useful for their thin, lightweight design, and high performance. In addition, ADP arrays are available from Hamamatsu Corporation, Bridgewater, N.J. 08807 as part number S8550. A pictorial representation of a 4×8 array of 2×2×10 mm LSO scintillator array 20 and a matched APD detector array 22 is shown in FIG. 5.

The spatial resolution of a PET scanner is determined in large part by the scintillator design and detector configuration. Increasing the depth or length of the scintillator, for example, increases the signal strength from the detector, by increasing the path length of the gamma-ray within the crystal. The increased path length results in an increase in the conversion efficiency of gamma rays to light photons.

Increasing the scintillator depth, however, also reduces the spatial resolution, due to the increase of scatter, unwanted reflections and detector cross-talk, for example. A preferred embodiment of the ring tomograph 10 shown in FIG. 6, therefore, includes a 5 mm thick LSO scintillator array 20 for higher spatial resolution than is available with a 10 mm thick LSO array.

Figure 7:
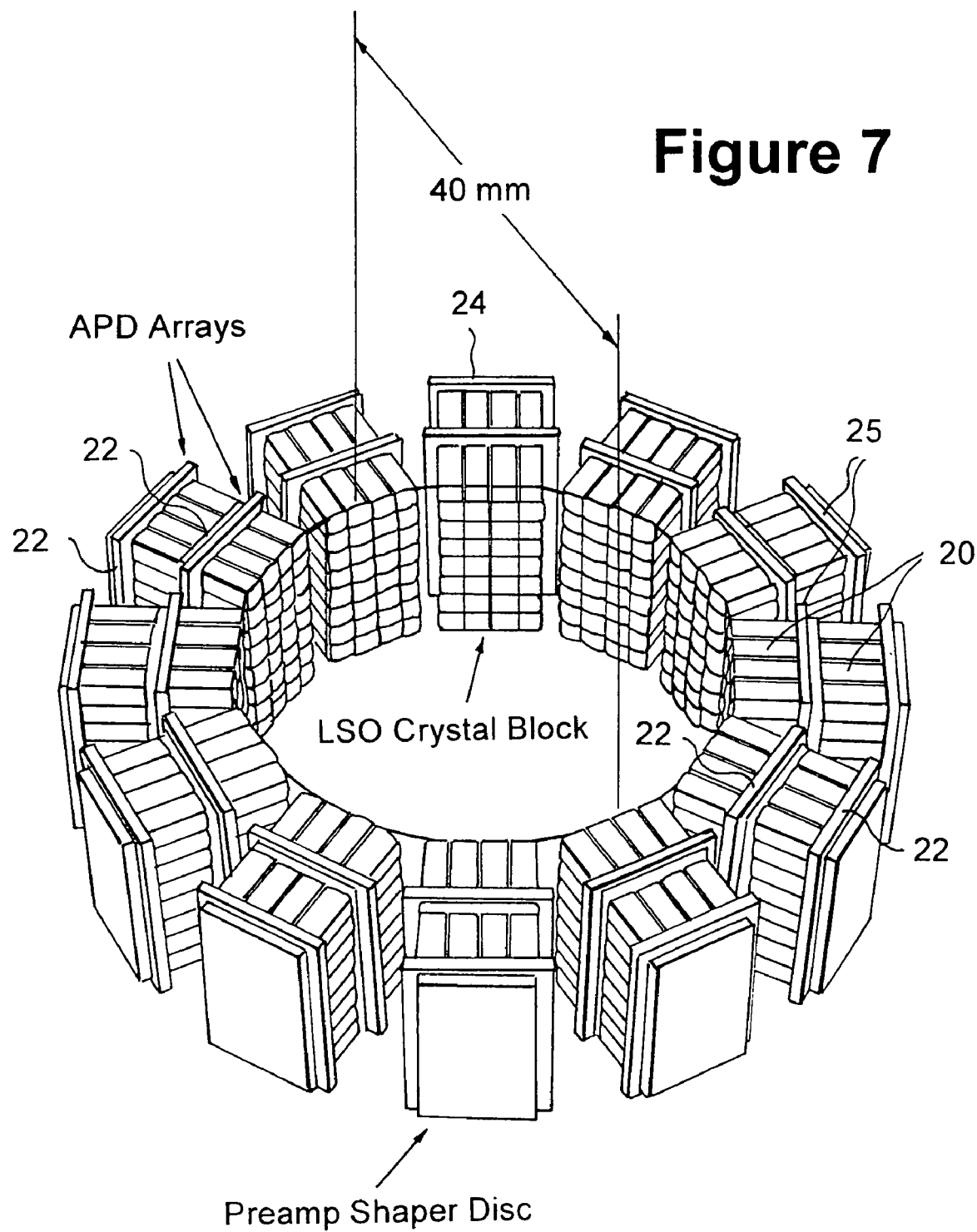
FIG. 7 is a perspective outline view of an alternative embodiment of a ring geometry, which includes two stacked layers of thin scintillator arrays, with two corresponding photodetector arrays.

An alternative embodiment, shown in FIG. 7, includes two layers of 5 mm thick LSO scintillator arrays 20, with two corresponding, matching APD arrays 22. This embodiment combines the advantages of higher sensitivity from a thinner scintillator and higher signal-to-noise ratio than would be achievable with a thicker scintillator. The depth of interaction is preferably measured in this embodiment and used to increase spatial resolution. Variations of this embodiment include changes in the stacking order from that shown in FIG. 7. For example, the two layers of LSO may optionally be adjacent to one another with the detector arrays positioned on the ends of the stack.

Figure 8:
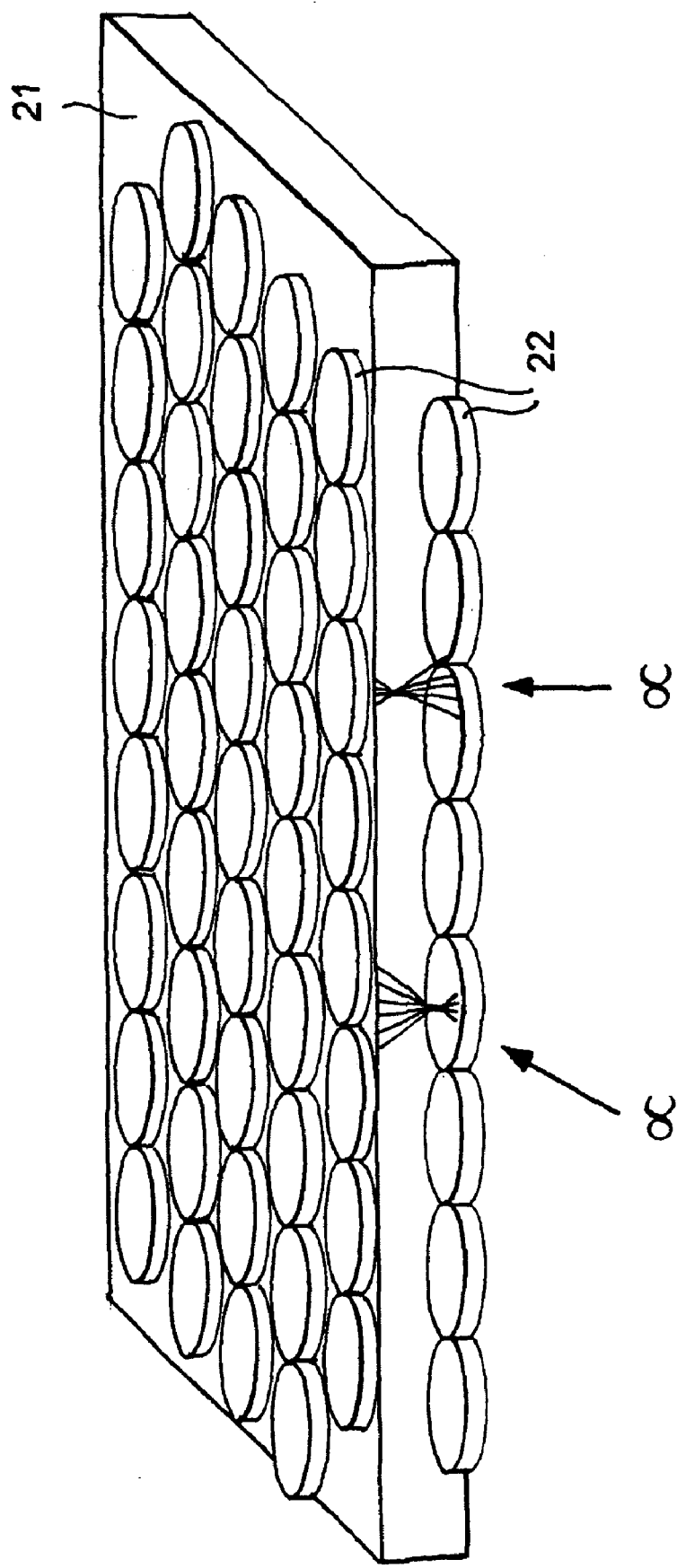
FIG. 8 is a perspective view of a single slab of scintillating material, coupled to two detector arrays, for use in a light-sharing arrangement.

In still another embodiment shown in FIG. 8, the LSO scintillator array is replaced with a solid slab of LSO 21, preferably of about 10 mm thickness. An array of APDs 22 is coupled to each side and aligned as shown in FIG. 8. In this light-sharing LSO/APD approach, pixelating the crystals is avoided, and the depth of interaction (DOI) is determined directly as described in *Reconstruction In PET Cameras With Irregular Sampling And Depth Of Interaction Capability*, IEEE on Nuclear Science, 45:3, pp. 1225–1230 (June 1998), which is incorporated herein by reference.

Figure 9A:
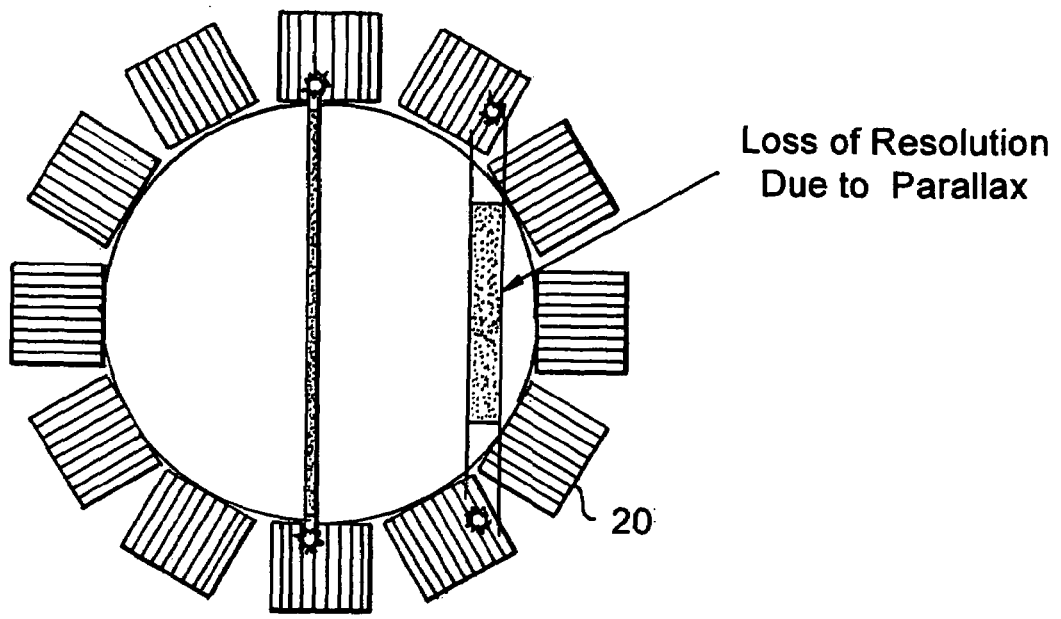
FIGS. 9a and 9b are pictorial representations of a parallax problem in a conscious animal PET formed in accordance with the present invention.
Figure 9B:
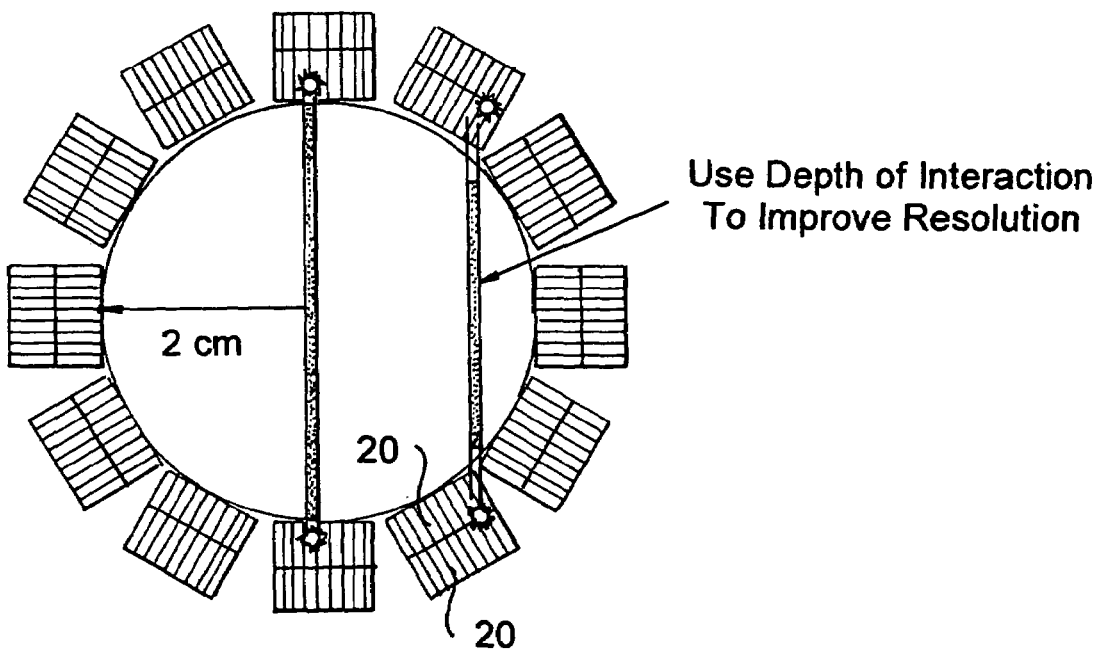

The small animal PET scanner of the present invention is unique when compared with conventional PET scanners, in that the subject totally fills the volume between the detectors. The conscious animal PET 10 of the present invention is a factor of four times smaller than conventional small animal tomographs. The scheme shown in FIG. 9a used in conventional scanners is avoided in the present invention because it creates greater parallax errors in coincidence detection from annihilations occurring off-axis. This off-axis error increases as the size of the PET detector ring 10 decreases relative to the object scanned. As shown in FIG. 9a, the gamma-ray pairs emitted off-axis impinge on the scintillators 20 at an off-normal angle of incidence. Therefore, there is a reduced depth of interaction, resulting in a lower gamma-to-light photon conversion efficiency. The consequence is a weaker pulse, as well as a blurring of the image.

To assess the impact of this error on the present invention, an analytical model is preferably developed. At each radial position, the intrinsic detector resolution is convolved with the parallax blurring, projected to the radial direction, and convolved with the same image from the opposing detector of the coincident pair to estimate image resolution.

Figure 10:
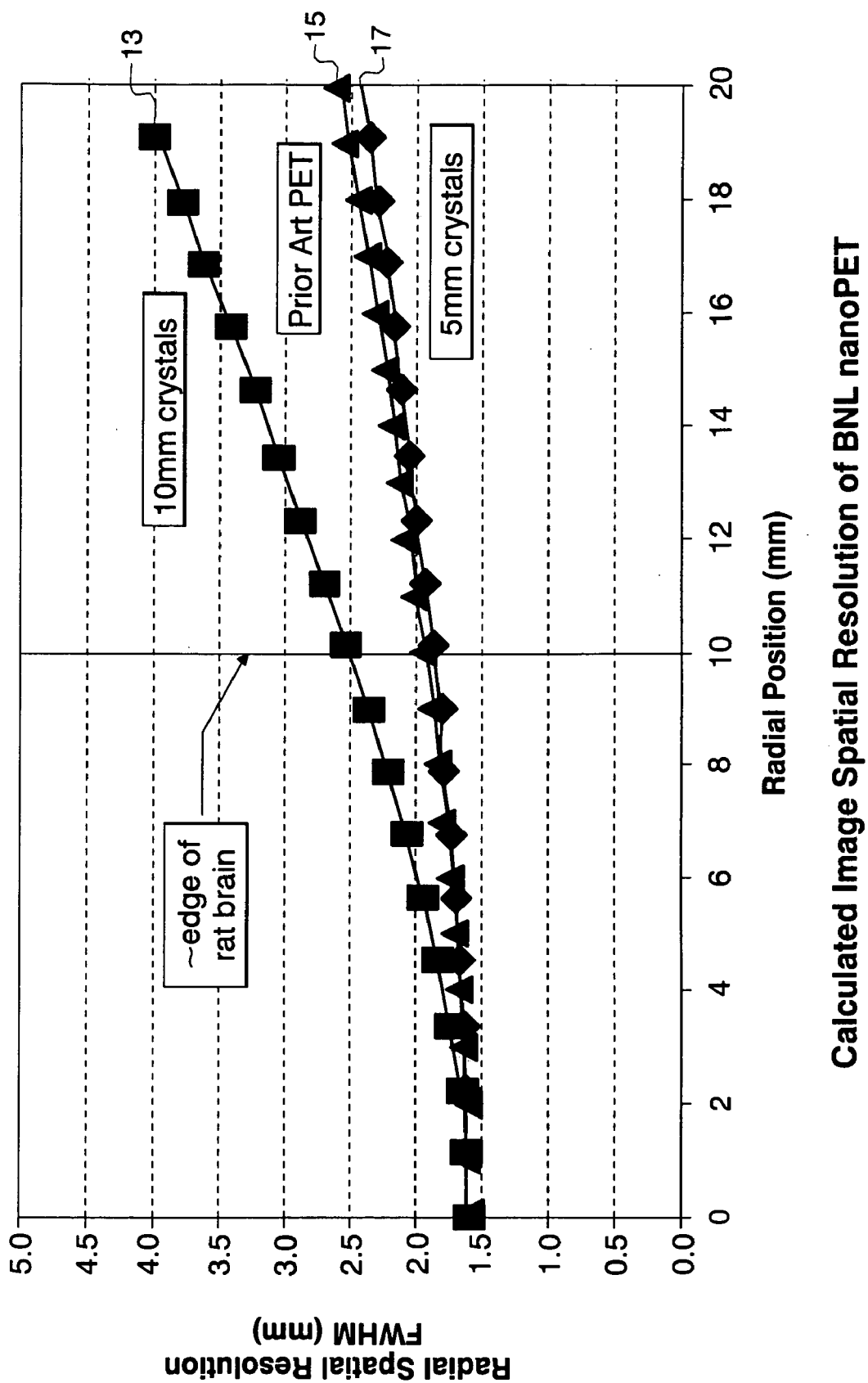
FIG. 10 is a graph of image spatial resolution as a function of off-axis position calculated from an analytical model of a conscious animal PET formed in accordance with the present invention.

FIG. 10 is a graph of image spatial resolution calculated from the analytical model discussed above. The results for a conventional small animal PET scanner of about 17 cm diameter by about 2 cm axial FOV, plotted as diamonds on line 17, are compared with two embodiments of the present invention. One embodiment, plotted as triangles on line 15, includes a 5 mm thick scintillator and the second, plotted as squares on line 13, includes a 10 mm thick scintillator. The model reproduced published resolution values as a function of radius to within about 10% for a range of conventional small animal PET scanners.

The edge of a rat brain is indicated at 10 mm from the center (radial position of 0) of the field of view in the plot. At the edge of the rat brain, the expected spatial resolution is 2.5 mm for a single layer of 10 mm thick LSO, and 1.9 mm for a single layer of 5 mm thick LSO. Over the radial position from 0 to 10 mm, the predicted spatial resolution for the 5 mm thick scintillator is comparable to much larger conventional scanners. Improved uniformity in resolution over the entire extent of the brain, corresponding to 0 to 10 mm in radial position, is preferably achieved by using the alternate embodiment, shown in FIG. 7, which includes two layers of 5 mm thick crystals, in conjunction with well-known depth of interaction capability.

Figure 11B:
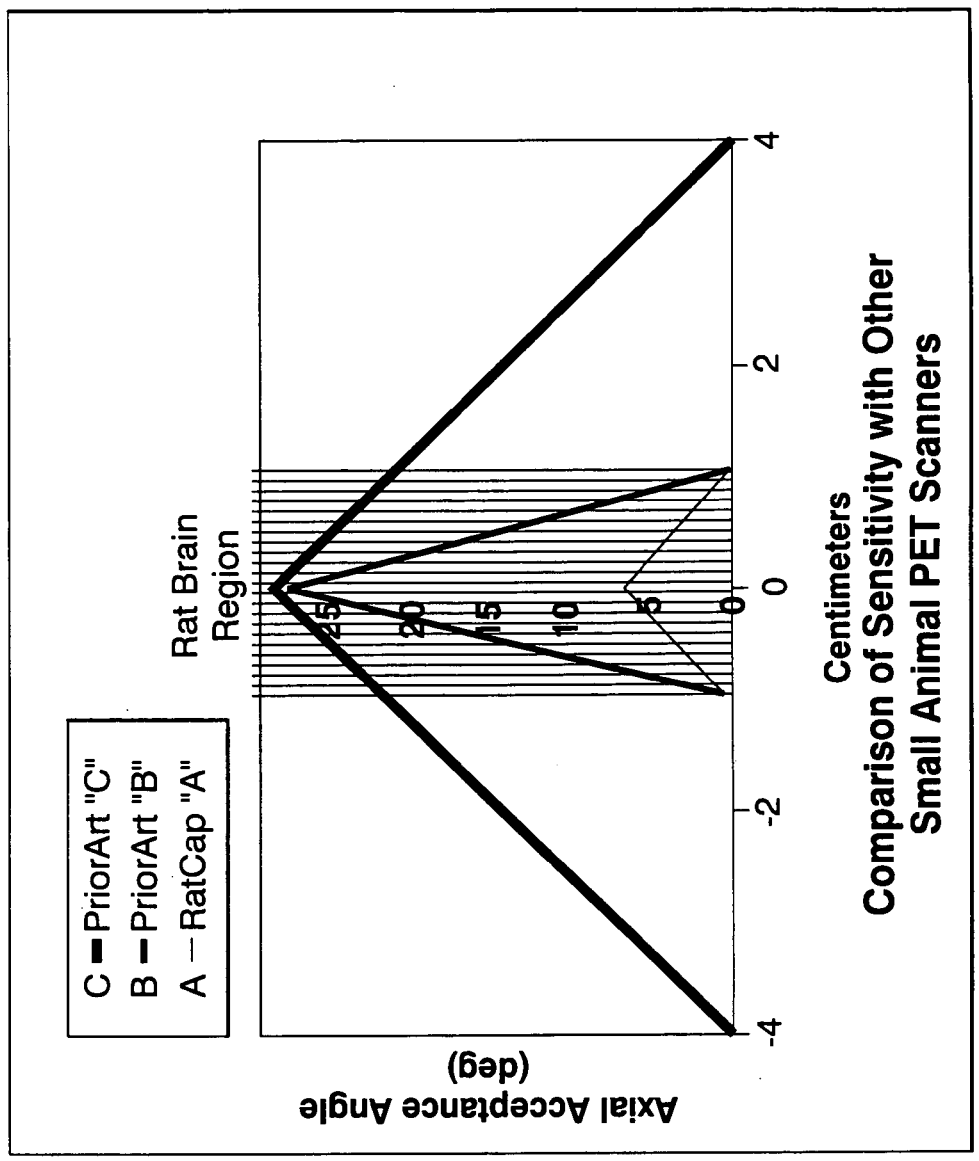
FIG. 11b is a graph showing the effect of miniaturizing a small animal PET scanner on the axial acceptance angle in comparison with conventional small angle PET scanners.
Figure 11A:
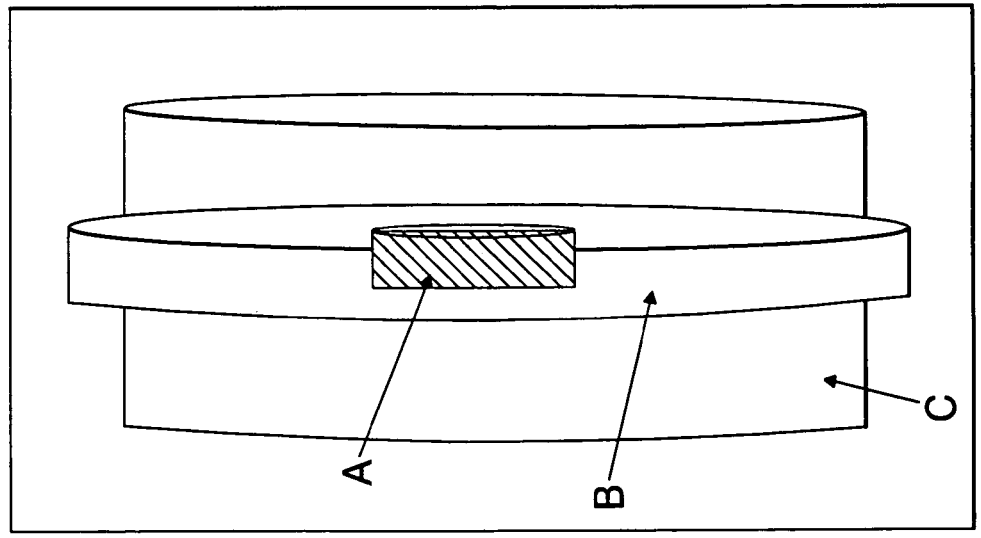
FIG. 11a is a pictorial representation of the relative size of the conscious animal PET of the present invention compared with the conventional small animal PET scanners.

System coincidence sensitivity is a function of the axial acceptance angle of the tomograph, defined as the light cone of acceptance from an on-axis emitter, i.e. by arc tan (L/R), where L is the length of the exposed detector area and R is the radius of the detector ring. The coincidence sensitivity degrades essentially linearly from the center to the axial edges in fully three-dimensional systems. FIG. 11a is a pictorial view of the relative size of the conscious animal PET 10 of the present invention compared to conventional small animal PET. Conventional tomograph A described above and shown in FIG. 11, has the largest diameter, 17 cm, of the three scanners and the same axial FOV, 2 cm, as the ring tomograph 10 of the present invention. The second conventional small animal scanner B has a 15 cm diameter and a large 8 cm axial FOV.

The system coincidence sensitivity also depends on the intrinsic detector sensitivity, but since this parameter does not differ from known conventional scanners, differences in the axial acceptance angle dominate comparisons of system coincidence sensitivity. The conscious animal PET 10 of the present invention preferably has the same 2 cm axial FOV, but about a factor of four smaller diameter compared to conventional scanner A. As shown in FIG. 11b, therefore, the axial acceptance angle of the conscious animal PET 10 is over four times larger than that of scanner A. Coincidence sensitivities are proportional to the axial acceptance angle. Therefore, the conscious animal PET 10 of the present invention preferably has over four times the coincidence sensitivity of conventional scanner A.

Compared to the much longer scanner B, although the solid angle in the center of the FOV is comparable, the axial FOV of the conscious animal PET formed in accordance with the present invention drops off more rapidly, as shown in FIG. 11b, resulting in lower sensitivity for the front and back of the brain. An alternative embodiment of the present invention may include a longer scanner design for an increased axial FOV and increased sensitivity in the front and back regions of the brain. However, an axial extent of 2 cm is the preferred embodiment of the present invention, offering the advantages of reduced size and weight, as well as a significant reduction in noise generated by random scattered gamma rays from outside the FOV.

The preferred mode of the present invention utilizes twelve 12 arrays of small, optically isolated scintillator crystals 20. Each scintillator crystal in the array 20 is preferably coupled to an independent avalanche photodiode 22, representing one channel of the scanner. This configuration avoids complex readout schemes required in current commercial block detectors that rely on light-sharing among, typically, a small number of photomultiplier tube channels.

Figure 12A:
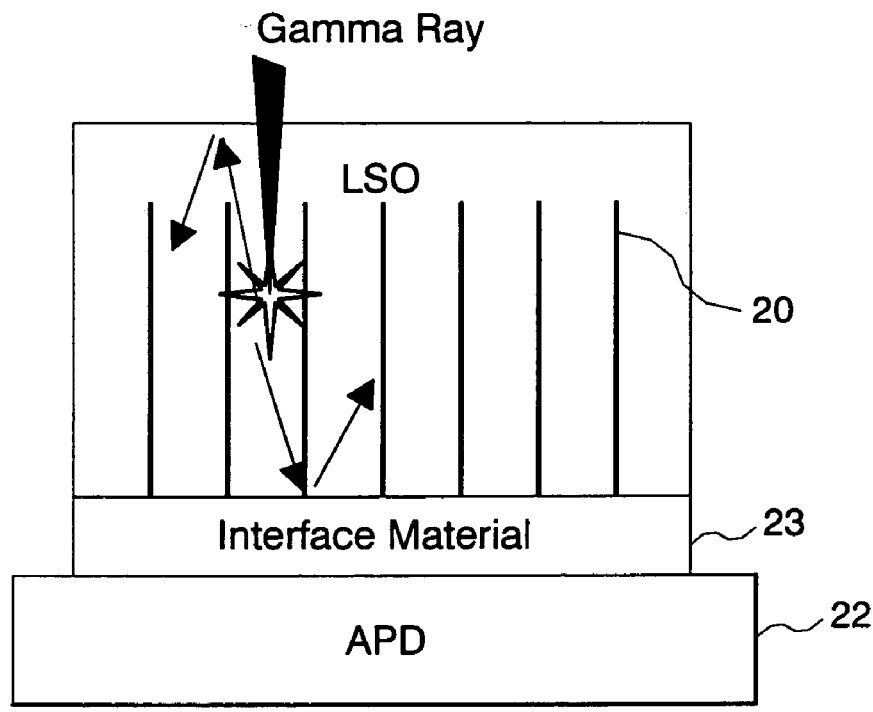
FIG. 12a is a side view of a pixelated scintillator block coupled to a detector array showing cross-talk between pixels.

However, an issue arises with independent-readout crystal arrays as to how to handle cross-talk between crystals. Cross-talk, as defined here, occurs when a single incident gamma ray causes signals in more than one readout channel. Cross-talk can reduce spatial, energy, and time resolution. It arises from Compton scattering from one crystal to another or from the escape of the photoelectron from the primary crystal following photoelectric absorption. Cross-talk also includes direct hits from gamma rays due to imperfect optical isolation of the scintillation photons within a single crystal, as shown in FIG. 12a. Each of these effects can be expected to increase as crystal size is reduced in an effort to achieve higher spatial resolution.

FIG. 12a shows an interface material 23 between the scintillator array 20 and the APD array 22. The present invention optionally includes the interface material 23 which preferably includes glass.

Light output and full-width half maximum (FWHM) energy resolution at 511 keV for LSO scintillator arrays from different manufacturers is provided in P. Vaska et al., *RatCAP: Miniaturized Head-Mounted PET for Conscious Rodent Brain Imaging*, IEEE Medical Imaging Conference (Oct. 18, 2003), which is incorporated herein by reference. Arrays of scintillator "pixels" formed by cutting into a solid block of LSO were tested with and without various types of reflective separators between the scintillator pixels, which were matched to the avalanche detector area. Measurements of the cross-talk using different scintillator and reflector configurations, along with an analysis of the effects of inter-crystal cross-talk on independent-readout crystal arrays, are also provided in the above-identified reference.

Figure 12B:
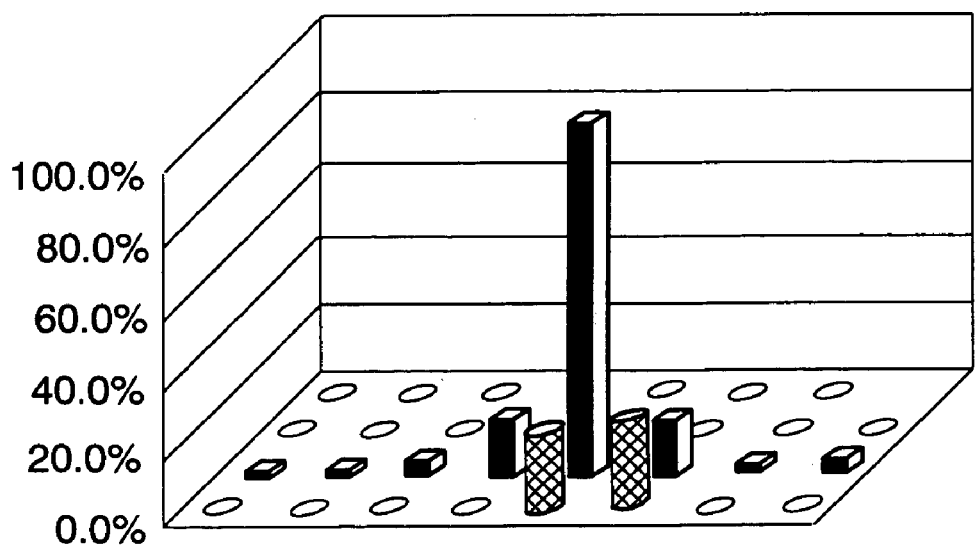
FIG. 12b is a distribution of cross-talk signals for a selected crystal.

A quantitative measure of cross-talk is the increase in signal produced by cross-talk correction, i.e., the inclusion of signals from adjacent pixels. FIG. 12b depicts the distribution of cross-talk signals for a selected crystal in a 4×8 LSO scintillator array 20 of about 2 mm×2 mm pixel cross-sections. The 10 mm thick array 20 is manufactured by Proteus by first cutting a solid LSO block parallel to the short side, into 8 square slabs and polishing to a specular finish. Reflector sheets are inserted between slabs and the block glued back together. The block is then cut along the long dimension, polished, and reassembled, resulting in continuous reflectors in the long direction, and short reflectors in the short direction.

There is less cross-talk between crystals separated by a continuous reflector sheet (along the long axis) than between crystals separated by the narrow, cut reflector strips (along the short axis). There is preferably about a 25% increase in the coincidence sensitivity by using the combined signals, which is preferably achieved by adding the analog pulse height information to the readout chip. Improvements in the placement of reflective sheets are preferably used to decrease the amount of cross-talk.

Figure 6:
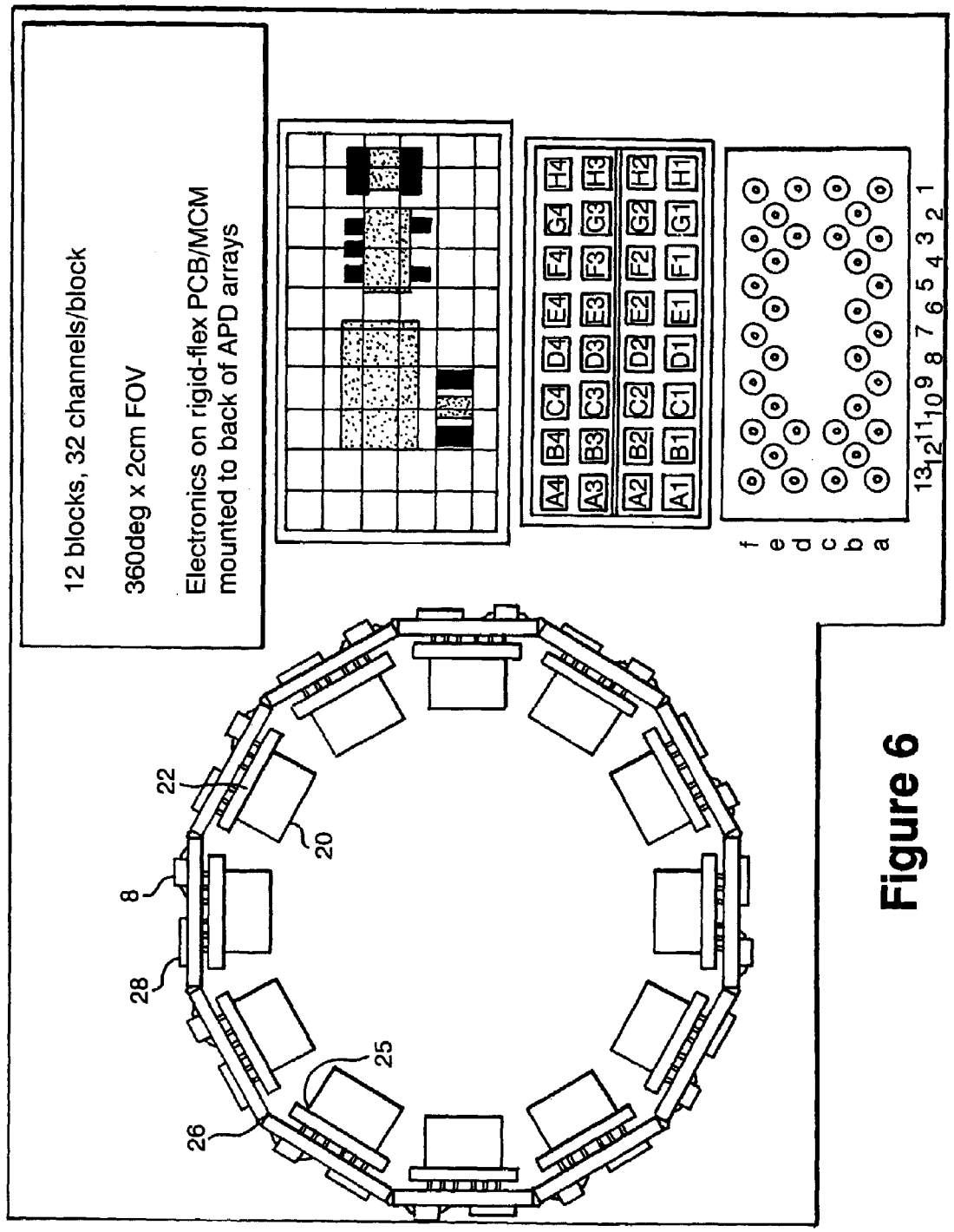
FIG. 6 is a top outline view showing the ring geometry of the preferred configuration shown in FIG. 4.

In another embodiment, the effects of cross-talk are reduced with the use of a reflective mask 25, preferably positioned on the end of the crystal array and in contact with the APD as shown in FIG. 4 and FIG. 6. By allowing light only through an aperture that exactly matches the sensitive area of the APD array 22, the light output of the detector is increased. The mask may be cut from the same reflective coating that is used in the Proteus crystal arrays and has real advantages in light gain over the powder packing used in other crystal arrays. The reflective coating is available from 3M Corporation, St. Paul, Minn. 55144. The light gain and reduced cross-talk improves both the energy resolution and the timing resolution.

In another embodiment, energy digitization for each crystal is preferably provided, and a correction for the effects of cross-talk performed. The effects of cross-talk correction for various scintillator array configurations, with different reflectors, has been discussed and analyzed in P. Vaska et al., *Effects of Inter-Crystal Cross-Talk on Multi-Element LSO/ APD PET Detectors*, IEEE Trans. Nucl. Sci., (2003), which is incorporated herein by reference.

The degree of cross-talk has particularly important implications for the design of the front-end electronics to read out the detector blocks. If all of the gamma-ray photons can be contained within one crystal, there is theoretically no need for energy digitization since an energy window can be enforced via simple discriminator thresholds for each crystal.

Figure 12C:
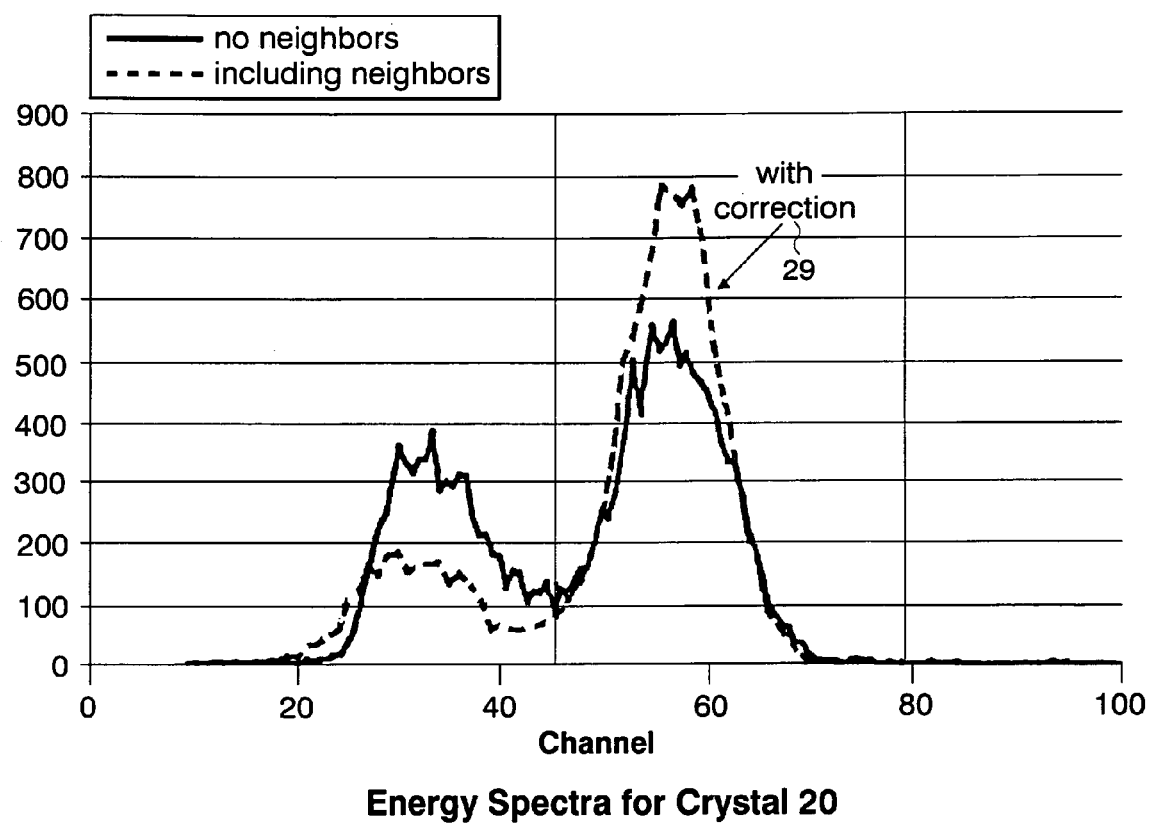
FIG. 12c is a plot of the uncorrected energy spectrum for a selected crystal in the array, and the spectrum corrected for cross-talk.

An example of the effect of cross-talk correction is shown in FIG. 12c for a selected crystal from a scintillator array. Line 29 in FIG. 12c represents the corrected spectrum and has been compressed to align the peaks so that the resolution and sensitivity can be directly compared. Though a 25% increase in coincidence sensitivity is possible, the position and time resolution is not affected. Therefore, in a preferred embodiment, digitization is not provided for cross-talk correction, simplifying the design of the front-end electronics.

In the preferred embodiment of the present invention, shown in FIG. 13, each block 31 preferably includes a 4×8 scintillator array and a 4×8 detector array, having thirty-two (32) channels. Each channel corresponds to a detector. The front-end electronics required to process each detector output include preamplification, shaping, and programmable-level zero-crossing discrimination or constant fraction discrimination. Referring to FIG. 4, a single Application Specific Integrated Circuit (ASIC) 28 is preferably provided on each block 31, in place of discrete components, to perform the front-end electrical processing and produce a discriminator pulse for each of the thirty-two (32) detectors 22 in one block array.

Each discriminator pulse is preferably encoded in the ASIC 28 with an address, corresponding to a channel on an nth block 31, which identifies the physical location of the encoded discriminator pulse on the detector ring. The encoded discriminator pulses, originating from 32 channels of data, are then serially read out over a single data link 33 corresponding to "Block n" as shown in FIG. 13. The tether 14, which attaches to the detector ring 10, serves the dual purpose of transmitting power to the detectors 22 and electronics 28 on the detector ring, and of transmitting the encoded discriminator pulses from the twelve (12) blocks 31 to the time-to-digital (TDC) 19 converter located on the animal container or cage 6. The singles rate over the entire detector is expected to be from 5–10 MHz. The tether 14, therefore, transmits about $10^7$ events per second.

Figure 14A:
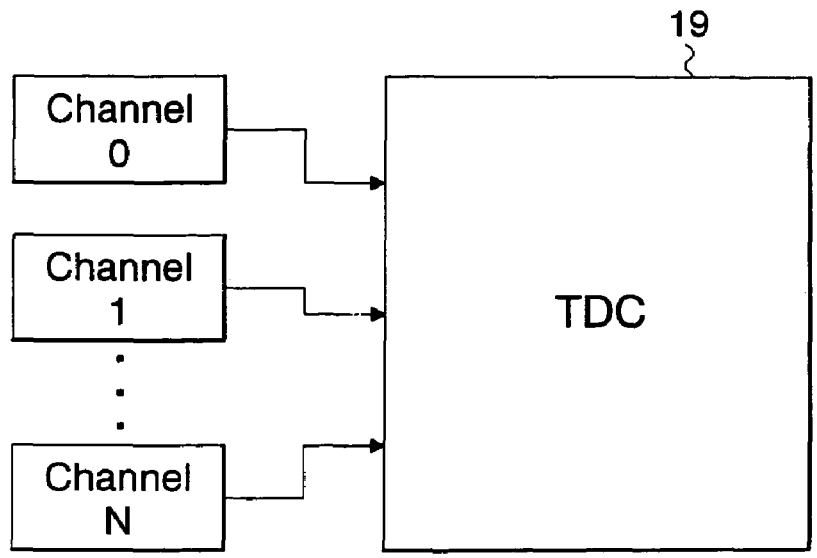
FIG. 14a is a block diagram of a conventional technique for transferring information from PET detectors for remote processing.

Time-of-occurrence information concerning an event and the corresponding address of the specific APD detector element that detected the event has conventionally been transferred to remote electronics, such as the TDC 19, for off-line processing via separate lines. In conventional PET scanners, each of these separate lines is dedicated to a single detector channel, as shown in FIG. 14a. The majority of PET scanning systems include hundreds or even thousands of these channels, which renders the conventional method far too cumbersome for a compact imaging system.

Figure 14B:
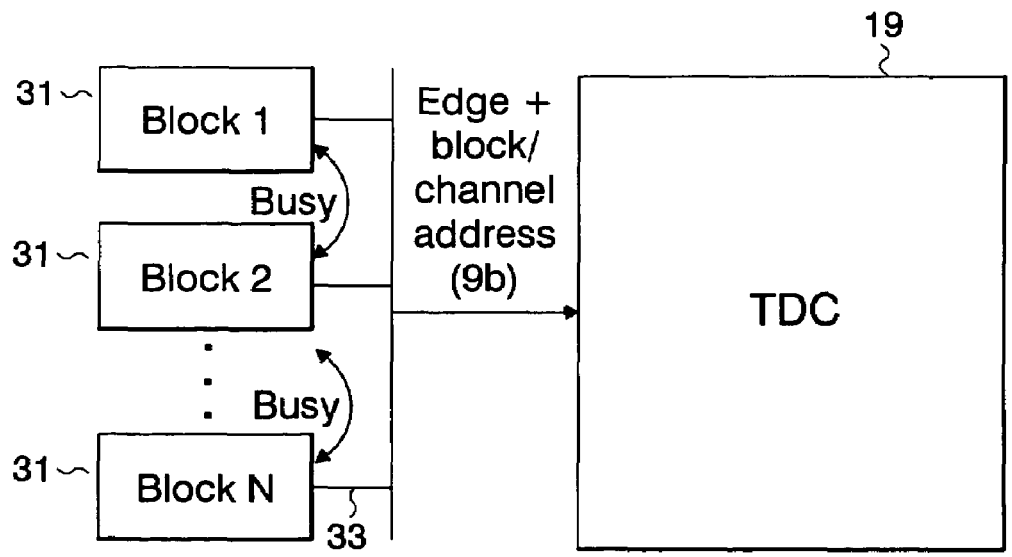
FIG. 14b is a block diagram of a technique in accordance with the present invention for serially transferring information in accordance with the present invention.

The conscious animal PET scanner formed in accordance with the present invention solves this problem by using a limited number of data links to transmit information concerning multiple events from a large number of channels (N) that share the link, as shown in FIG. 14b. The information required for each event is its time-of-occurrence, the address of the channel that detected the event, and the corresponding detector block. Information concerning the energy recorded in that channel may also be transmitted with the time and address information from the detector ring in accordance with the present invention.

Figure 15:
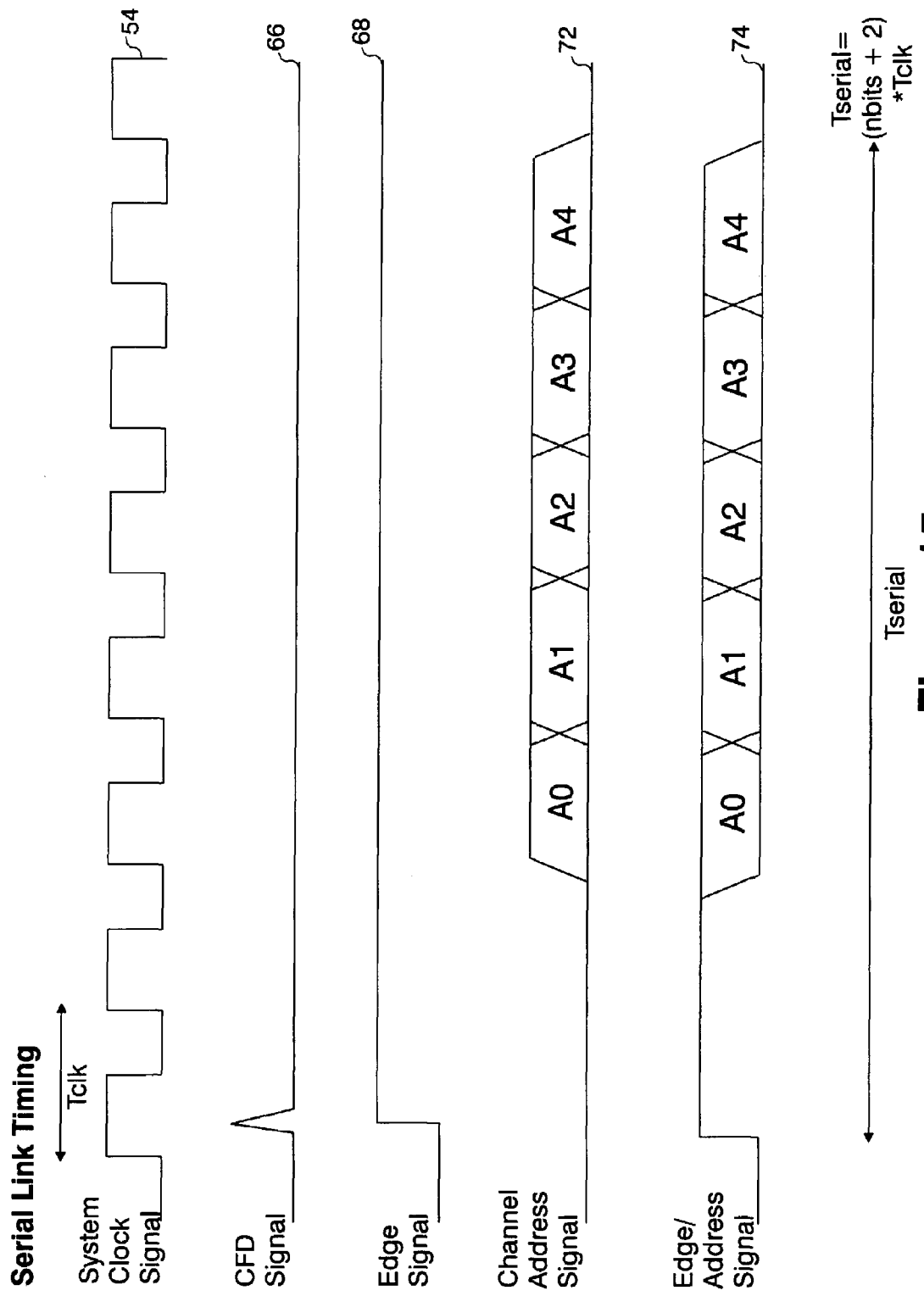
FIG. 15 is a timing diagram showing signals associated with the serial transfer of information from PET detectors in accordance with the present invention.

The time-of-occurrence of the event is preferably represented by an asynchronous position of a leading edge of a data packet from each of the ASIC devices in the detector ring. The address corresponding to the channel that detected the event is preferably serially encoded in the same data packet by a digital word having a length of $\log_2(N)$ bits, where N is the number of channels in the detector block. Thus, for a detector block 31 having thirty-two (32) channels, a minimum of five (5) bits would be required to encode the channel address. Information concerning the energy of the gamma ray is preferably encoded by the position of a second edge in the data packet. Therefore, edges representing time-of-occurrence and energy are preferably asynchronous with respect to a system clock while edges representing the channel address are preferably synchronous with respect to the system clock, as shown in FIG. 15.

Since the data link 33 is shared between N channels, the total duration of the data packet is preferably much less than the average inter-arrival time of events in the N channels. This is preferably accomplished by increasing the frequency of the system clock. For instance, assuming no energy information is transmitted and there is one guard bit, which has a duration of one period of the system clock, between the leading edge representing the time-of-occurrence and the beginning of the channel address, the maximum duration of the data packet is preferably represented by the following equation:

$$T_{packet} = (\log_2(N)+2)*T_{clock} \quad (1),$$

where $T_{clock}$ is the period of the system clock. To prevent events from being blocked by a busy link condition the duration of the packet is preferably represented by the following equation:

$$T_{packet} \ll 1/(N*\text{rate}) \quad (2),$$

where rate refers to the average rate of events per channel. The busy link condition, when there is a conflict between the detection of two or more substantially simultaneous events, is preferably resolved by a priority encoder, which preferably neglects the event associated with the lower channel address.

Figure 16:
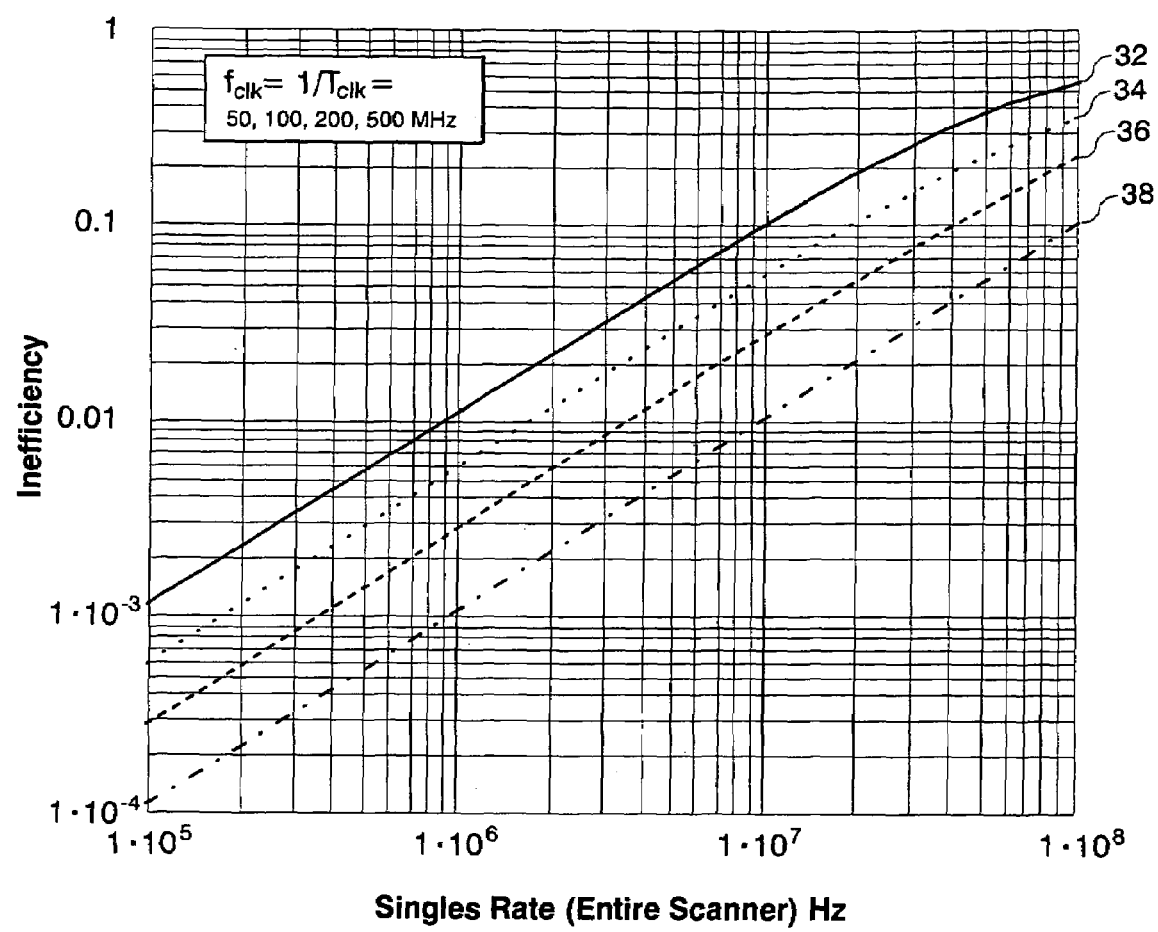
FIG. 16 is a graph of inefficiency or the probability that an event will be blocked by a busy link condition in the conscious animal PET scanner formed in accordance with the present invention.

A graph showing the probability that an event will be blocked by a busy link condition, which is also referred to as inefficiency, is shown in FIG. 16 for the case of N=32 channels and system clock frequencies of 50, 100, 200, and 500 MHz as indicated by lines 32, 34, 36, and 38, respectively. The abscissa of the graph is the singles rate for the entire scanner, which is assumed to have 384 total channels organized in twelve (12) blocks of thirty-two (32) channels.

The singles rate for the small animal conscious PET scanner of the present invention formed in accordance with the present invention is expected to be from 5–10 MHz over the entire detector. For a system clock frequency of 200 MHz, for example, this translates into an efficiency or probability that an event will be blocked of between 0.01 and 0.02.

Figure 17:
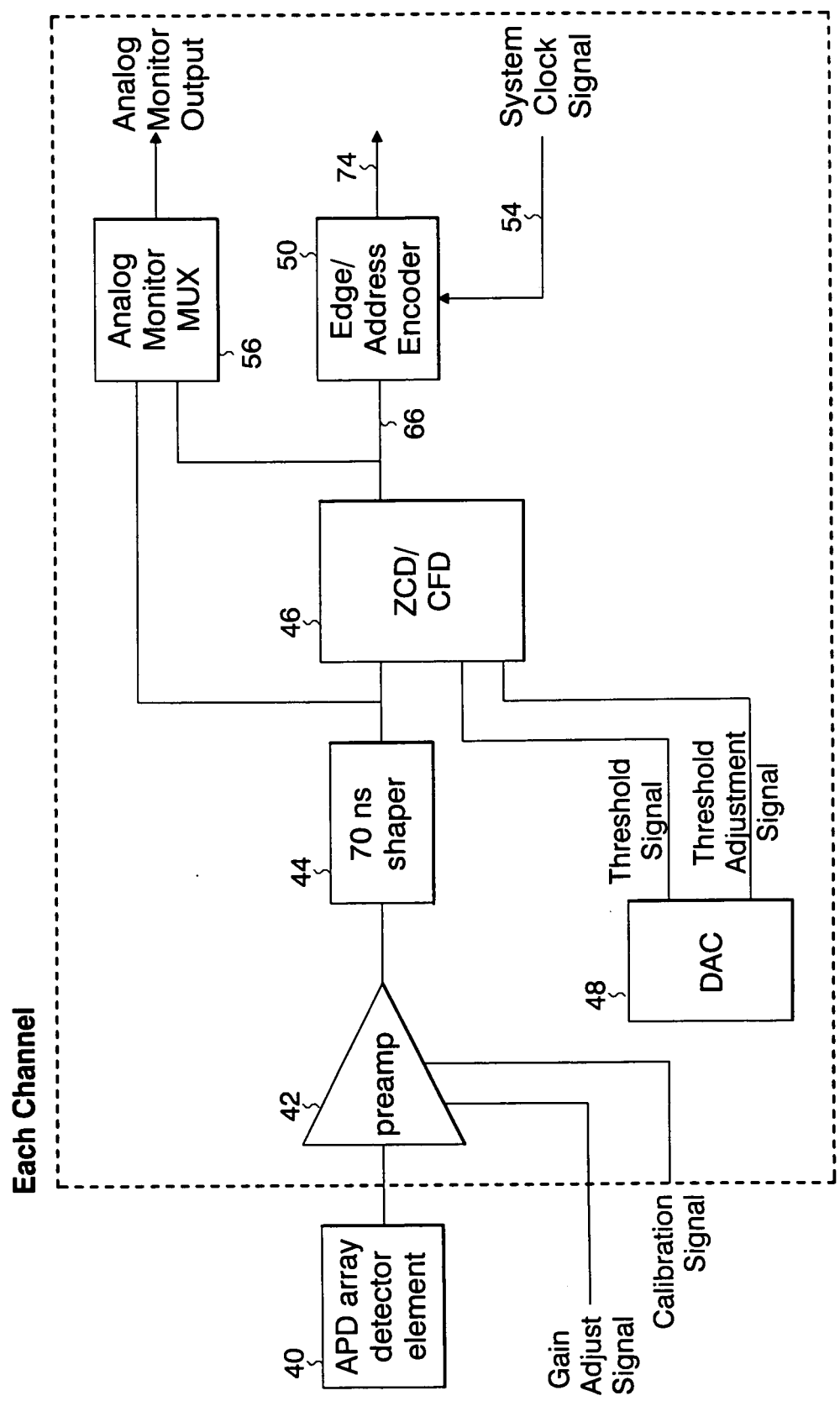
FIG. 17 is a block diagram of a preferred embodiment of the circuitry associated with detector channels in a detector ring formed in accordance with the present invention.

FIG. 17 is a block diagram of a preferred embodiment of electronic circuitry corresponding to a channel of the conscious animal PET scanner formed in accordance with the present invention. The output of an element 40 of the APD detector array is preferably connected to a preamplifier 42, which inputs gain adjustment and calibration signals obtained from a digital-to-analog converter (DAC) 48. The output of the preamplifier 42 is preferably shaped to be about a 70 ns pulse by one or more filtering networks in a shaper network 44. The shaped pulse is preferably inputted to a Zero Crossing Detector (ZCD) or Constant Fraction Discriminator (CFD) circuit 46, which generates precise logic pulses in response to the shaped pulse input crossing a given threshold, as well as the peak of the shaped pulse.

Detection of the peak of the shaped pulse preferably yields a timing pulse from the ZCD/CFD 46 that represents a time-of-occurrence of the corresponding event. The time between the first threshold crossing of the shaped pulse and the second threshold crossing of the shaped pulse indicates the energy of the event using a so-called "time-over-threshold method". The energy of the event is preferably represented by the position of an energy pulse from the ZCD/CFD 46. Since the energy measurement is being performed on the shaped pulse following the preamplifier 42 and shaper circuit 44, the value of the energy measurement is preferably calibrated to yield a more accurate result.

A DAC 48 preferably provides a threshold signal and a threshold adjustment signal to the ZCD/CFD 46. The ZCD/CFD 46 is preferably based on two comparators. One comparator is used for arming the ZCD/CFD 46 by triggering on signals having the proper energy by independently setting the threshold signal for the detector channels. The threshold is preferably set for the detector channels through a serially loaded shift register (not shown). The shift registers for each of the detector block ASICs are preferably daisy-chained and share the same data, control, and clock signals. The shift registers preferably set the detector channel DACs 48 to appropriate values. The remaining comparator in the ZCD/CFD 46 is preferably used to determine the baseline crossing of the bipolar signal, which represents the energy of the event as described above.

CFDs generally use a constant fraction or percentage of the input pulse to determine the timing of the output pulse relative to the input signal. This technique is not subject to jitter, which is typically caused by varying amplitudes or rise times of the inputs, such as in leading edge discriminators. The pulse output from the ZCD/CFD 46 preferably has a standardized amplitude and a preset duration.

The output of the ZCD/CFD 46 is preferably applied to an edge/address/priority encoder 50 that outputs a serialized edge/address signal 74, which includes the time-of-occurrence and the channel address corresponding to the detected event. The system clock signal 54 is preferably inputted to the edge/address/priority encoder 50 for synchronous timing. An analog monitor multiplexer 56 is preferably provided to enable external access to analog signals within the channel circuitry, such as the analog signals before and after the ZCD/CFD 46.

Figure 18:
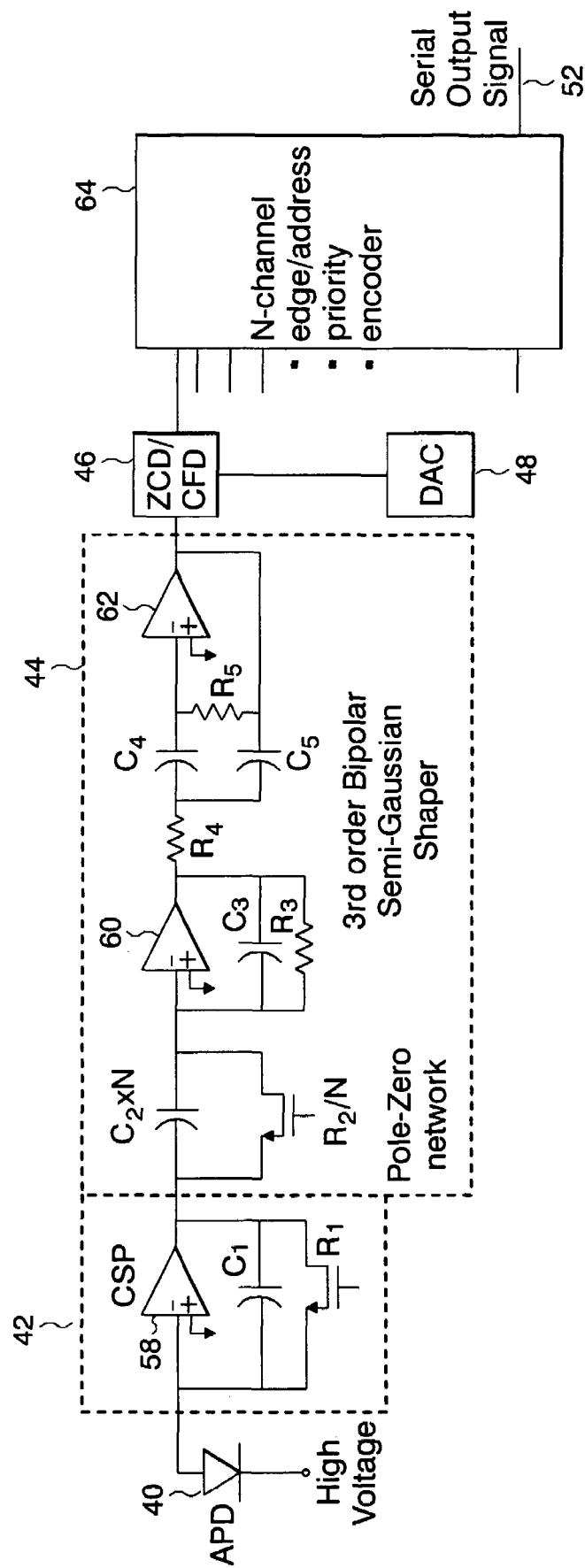
FIG. 18 is a partial schematic diagram of a preferred embodiment of front-end circuitry and a block diagram of the remaining circuitry associated with detector channels in a detector ring formed in accordance with the present invention.

FIG. 18 is a schematic diagram of front-end circuitry in relation to subsequent functional blocks for each of the detector channels. Preamplifier and shaping network parameters are preferably optimized with respect to technological parameters and operating point characteristics of the detectors, such as leakage current and gain, to minimize the Equivalent Noise Charge (ENC). Simulations have predicted an ENC of about 700 electrons rms at about a 70 ns peaking time. A gain of 3.3 mV/fC (where Cf=300 fC) was set for the preamplifier with about 1.3 mW of power dissipation.

The output of the APD element 40 is provided to the preamplifier 42 that preferably includes a parallel connection of a capacitor C1 and a resistance R1, which are connected in parallel across an inverting terminal and an output terminal of an operational amplifier 58. The resistance R1 is preferably realized by a Field Effect Transistor (FET) and the preamplifier 42 is connected in series with the output of the APD element 40.

Figure 31:
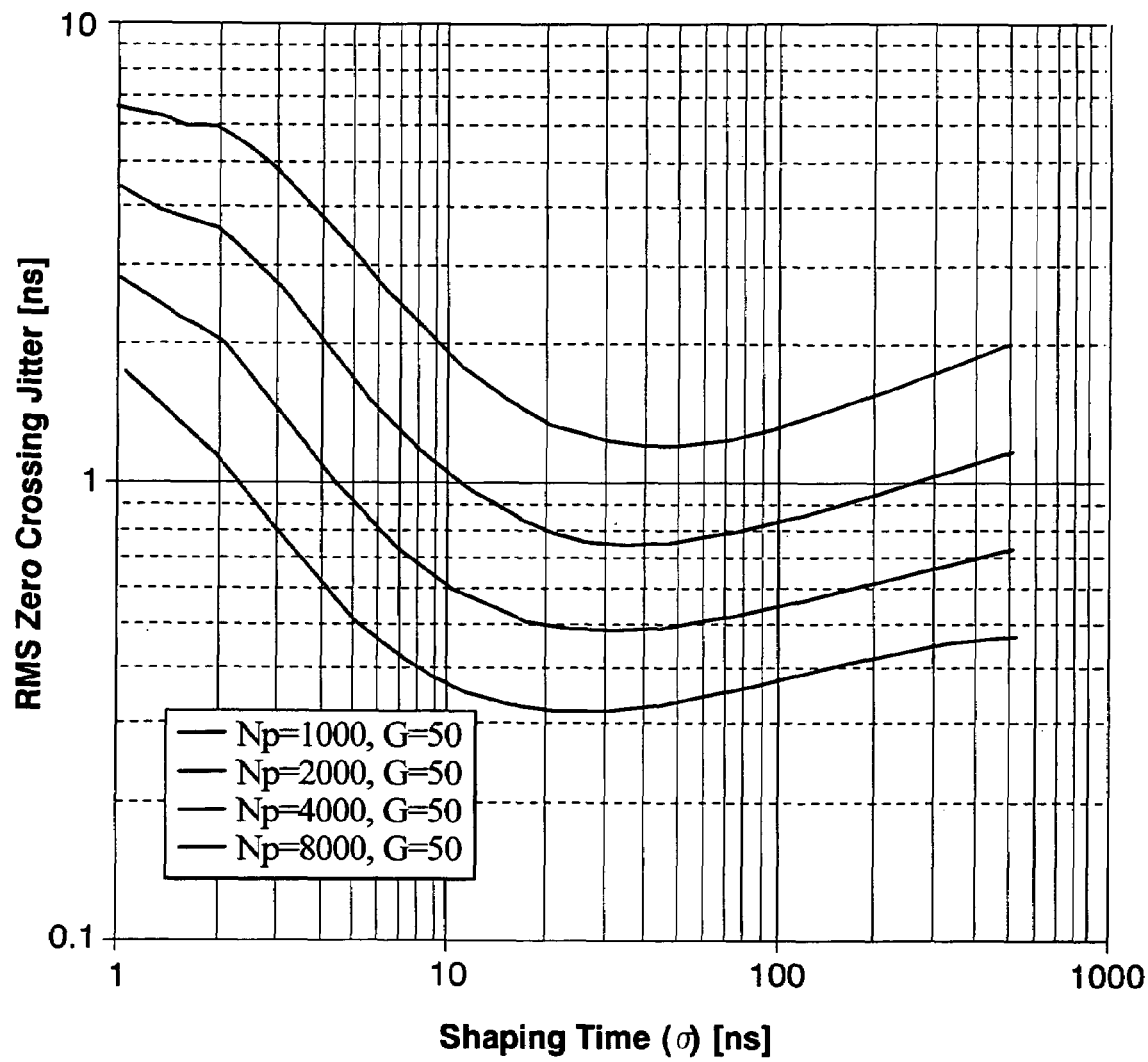
FIG. 31 is a graph representing the timing resolution or Root Mean Square (RMS) zero crossing jitter from the conscious animal PET formed in accordance with the present invention.

The output of the preamplifier 42 is provided to the shaper circuit 44, which preferably includes a pole-zero cancellation network, a 1st-order low pass filter, and a 2nd-order bandpass filter. An analysis was performed to determine the peaking time that optimizes timing resolution. Assuming that the LSO decay time is 40 ns and considering the series noise, the time from the peak to the zero crossing of a bipolar Gaussian between 25 ns to 90 ns would lead to a theoretical optimum of about 700 ps rms zero-crossing jitter, as indicated in FIG. 31. Therefore, the peaking time is preferably set to about 70 ns. Each transistor in the front-end circuitry is preferably optimized to minimize its electronic noise contribution.

The pole-zero network preferably includes a parallel combination of one or more capacitors C2 connected in series and one or more resistances R2 connected in series. The number of capacitors C2 is preferably the same as the number of resistances R2, the number preferably being greater than two (2). The resistance R2 is preferably realized by an FET and the pole-zero network is connected in series with the output of the preamplifier 42. The pole-zero network is preferably used to compensate the reset transistor non-linearity, as well as to reduce the noise contribution from subsequent stages.

The 1 st-order shaper network preferably includes a parallel combination of a capacitor C3 and a resistor R3 connected in parallel across an inverting terminal and an output terminal of an operational amplifier 60. A resistor R4 and a capacitor C4 are preferably connected in series between an output terminal of the operational amplifier 60 and an inverting terminal of an operational amplifier 62. A capacitor C5 and a resistor R5 are preferably connected in parallel across the capacitor C4 and the resistor R5 is connected in parallel across the inverting terminal and the output of the operational amplifier 62, which is essentially the 2nd-order shaper network.

The non-inverting terminal of each of the operational amplifiers 58, 60, 62 is preferably connected to ground and an output terminal of operational amplifier 62 is provided to the ZCD/CFD 46. An N-channel edge/address/priority encoder circuit 64 is shown in FIG. 18, which preferably includes the edge/address/priority encoder circuits 50 shown in FIG. 17 for each of N channels in a detector block. The serial encoder circuit 64 outputs a single serial output signal 52 to the TDC. Further details concerning the front-end electronics for the detector channels are provided in U.S. Pat. No. 5,793,254, which is incorporated herein by reference.

Figure 19:
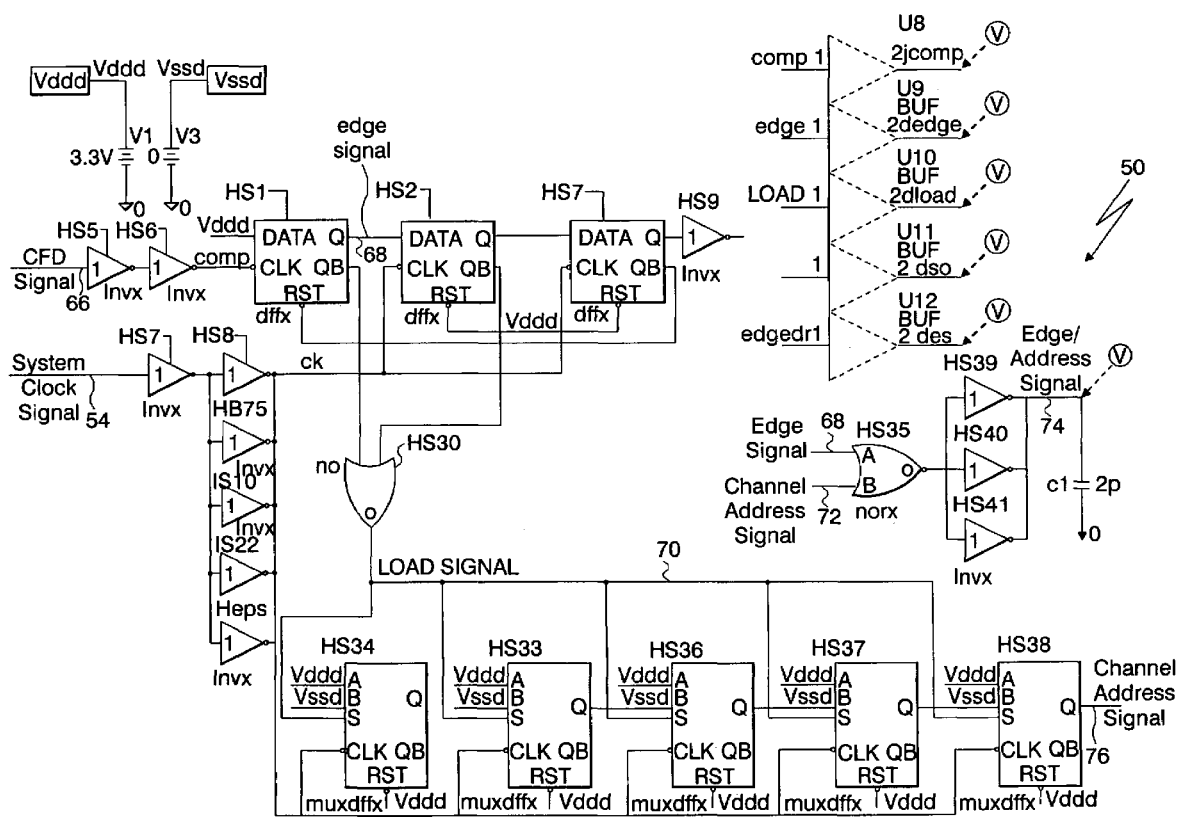
FIG. 19 is a schematic diagram of a preferred embodiment of serial encoding circuitry associated with detector channels in the detector ring formed in accordance with the present invention.
Figure 20A:
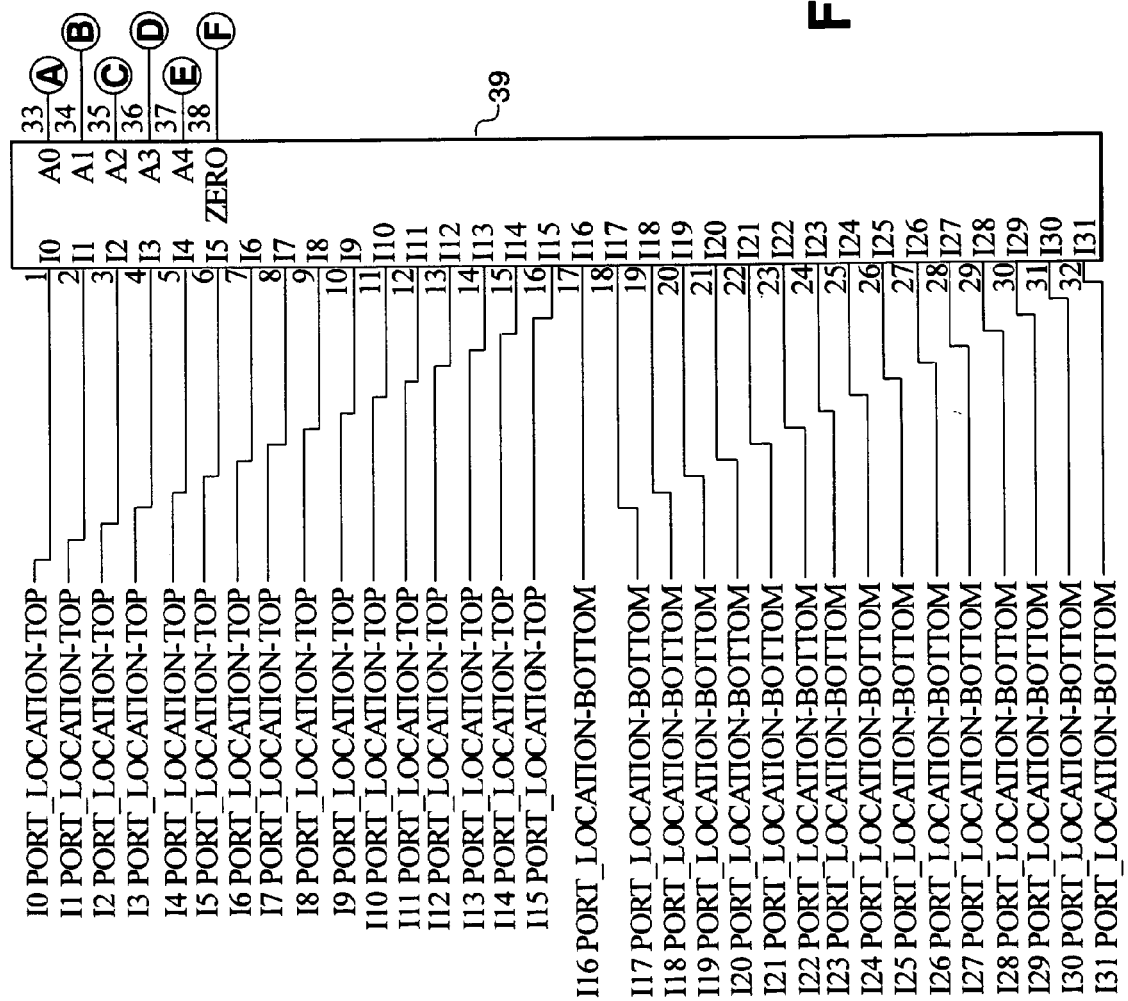
FIGS. 20–29 are schematic diagrams of an Application Specific Integrated Circuit (ASIC) implementation of the serial encoding circuitry formed in accordance with the present invention.
Figure 20B:
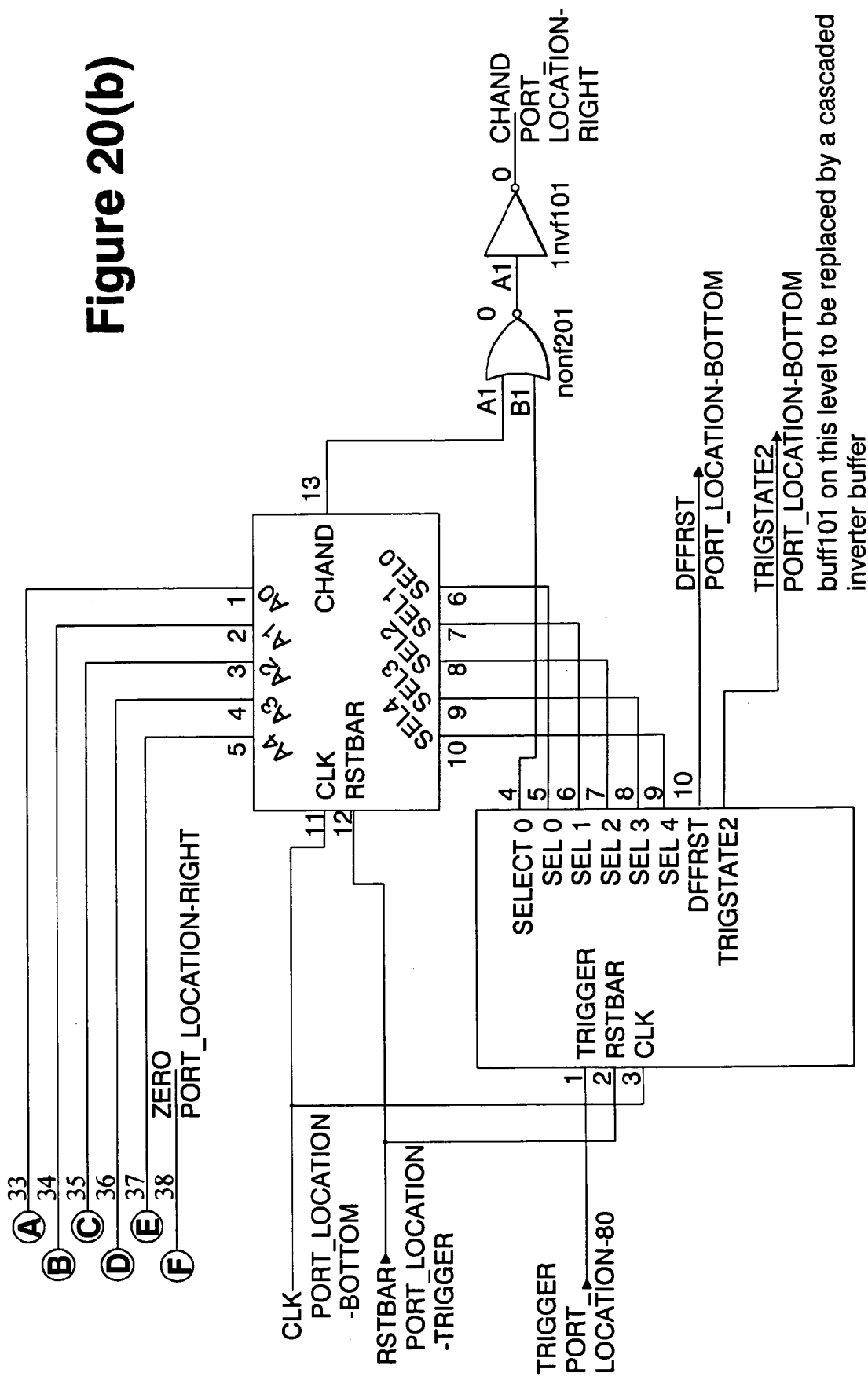
Figure 21:
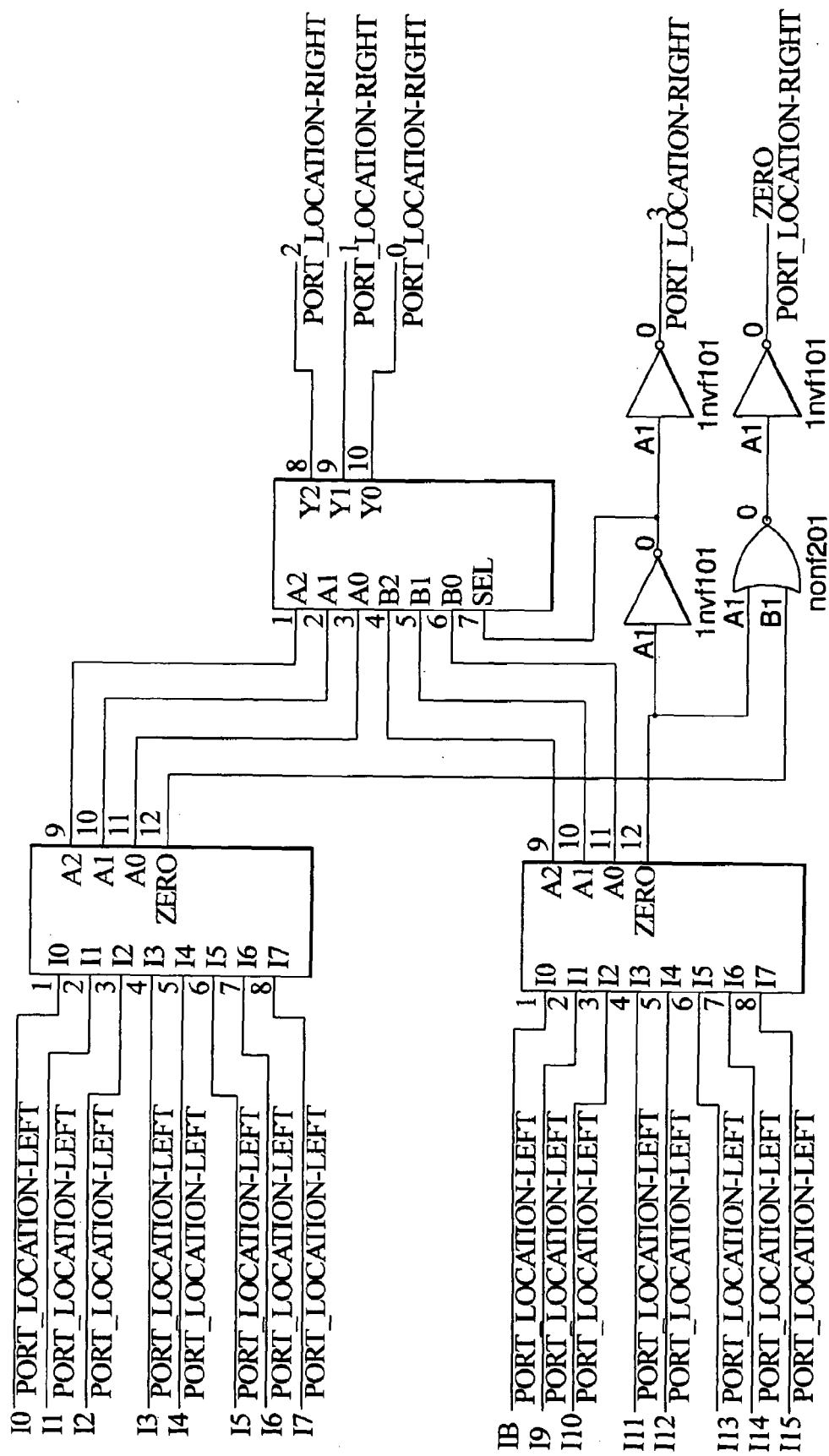
Figure 22A:
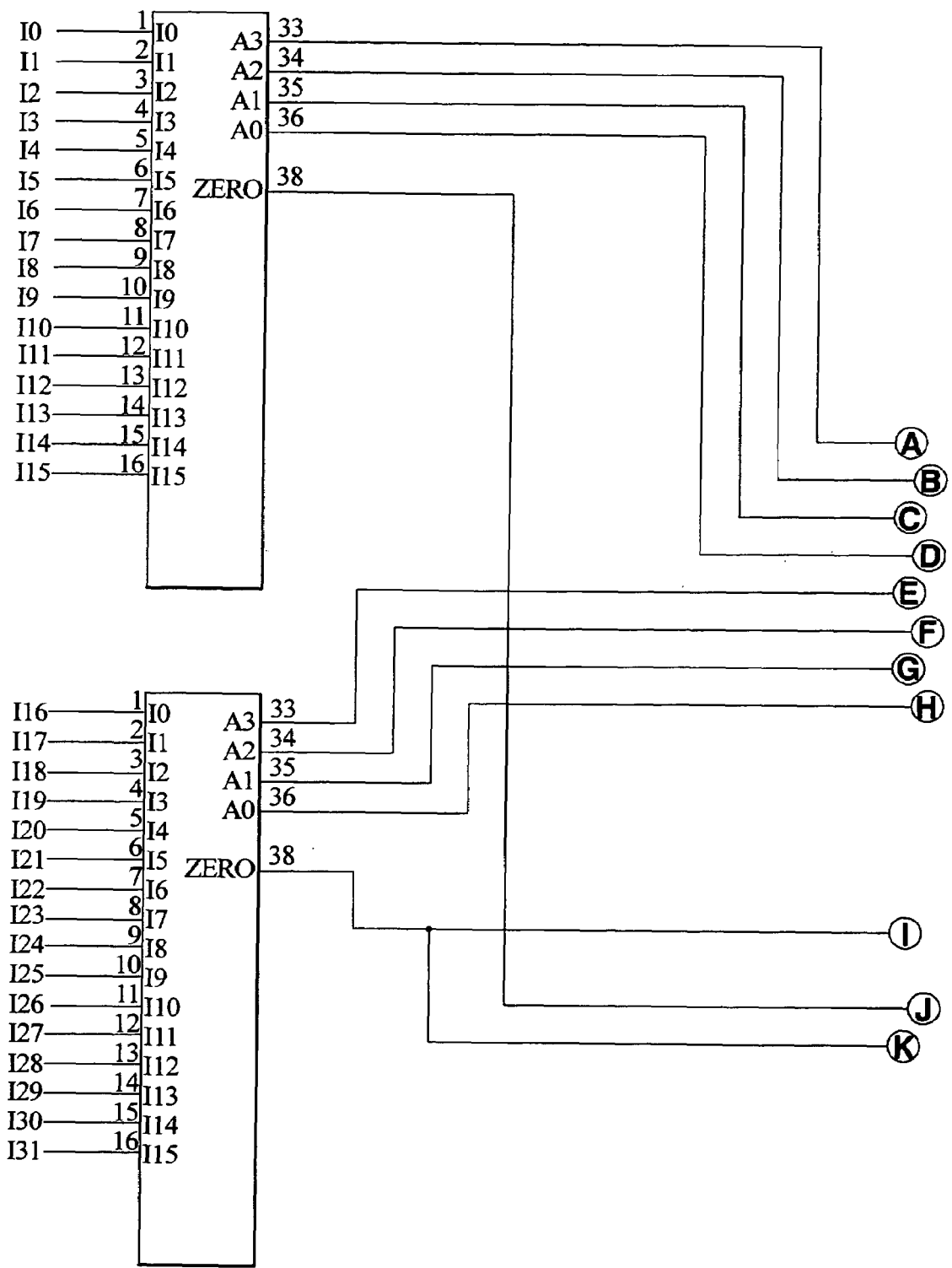
Figure 22B:
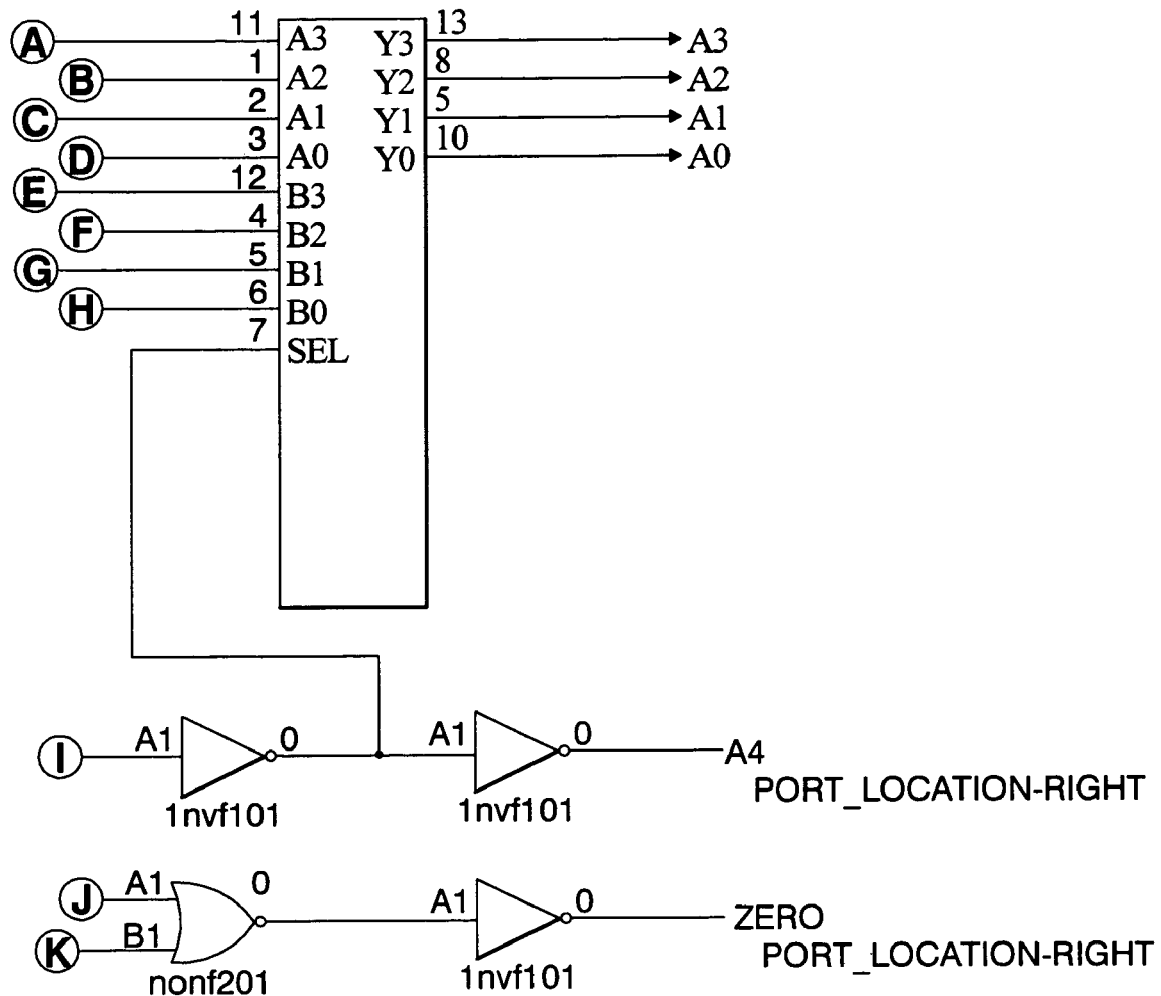
Figure 23:
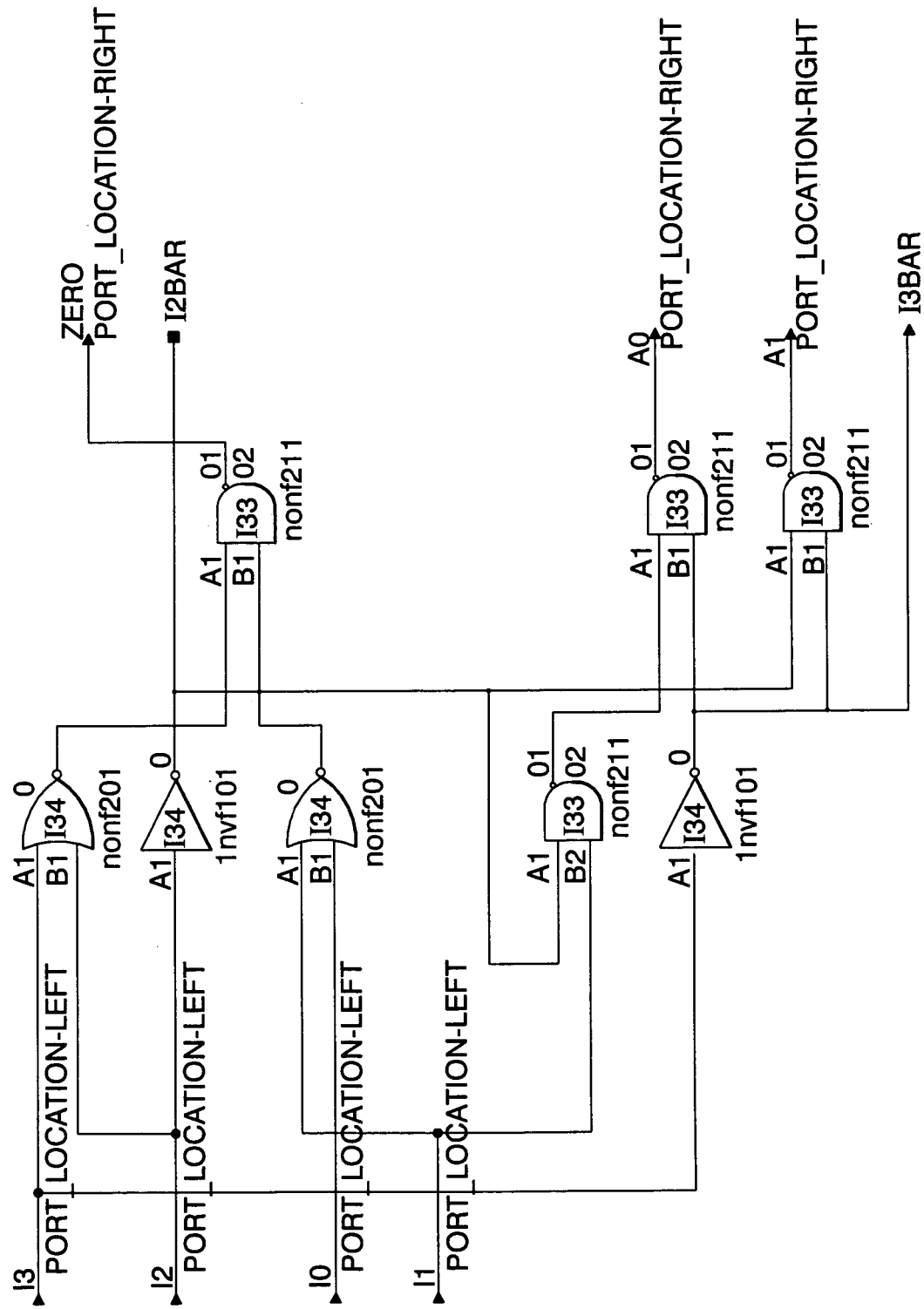
Figure 24:
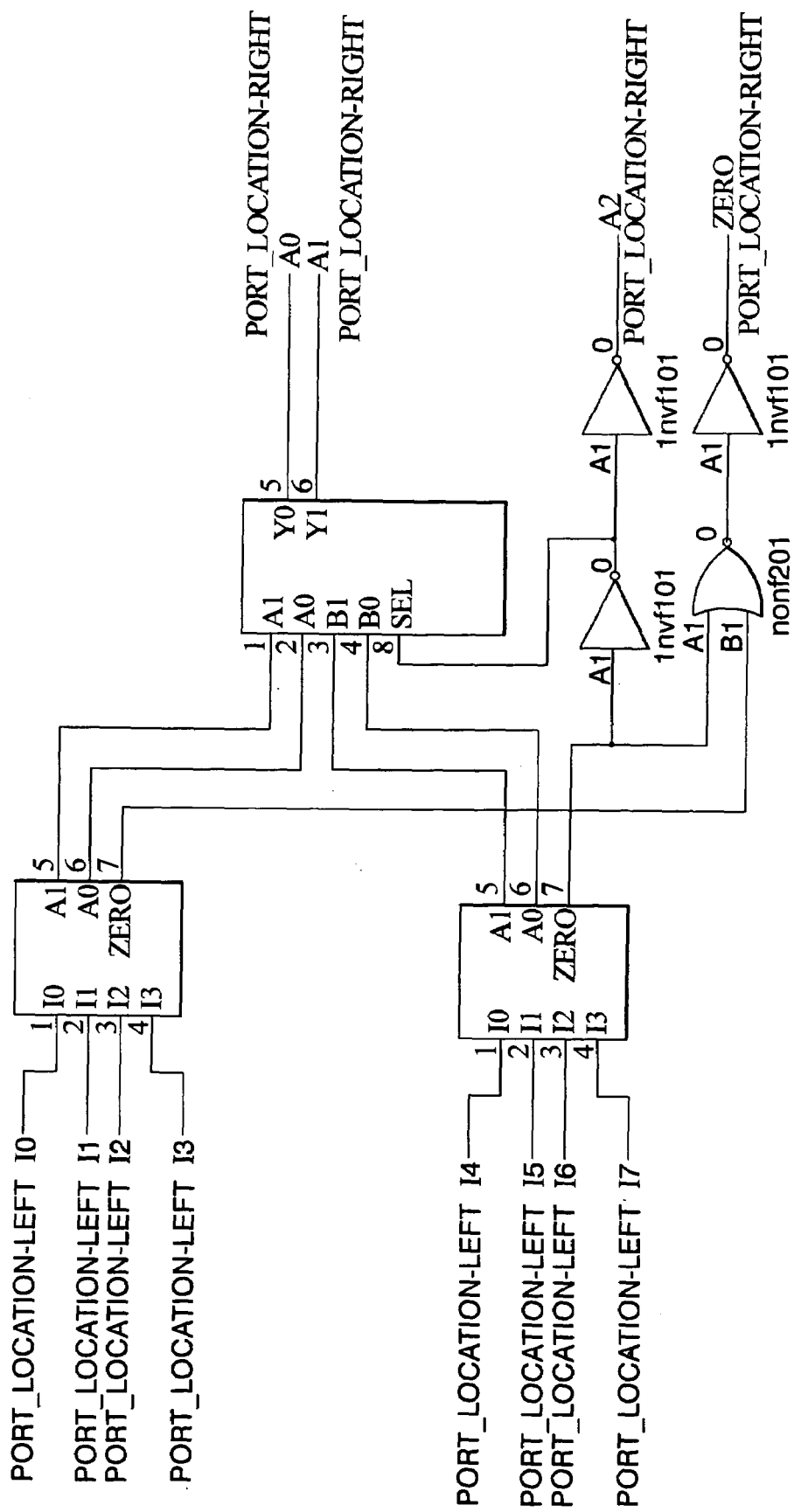
Figure 25A:
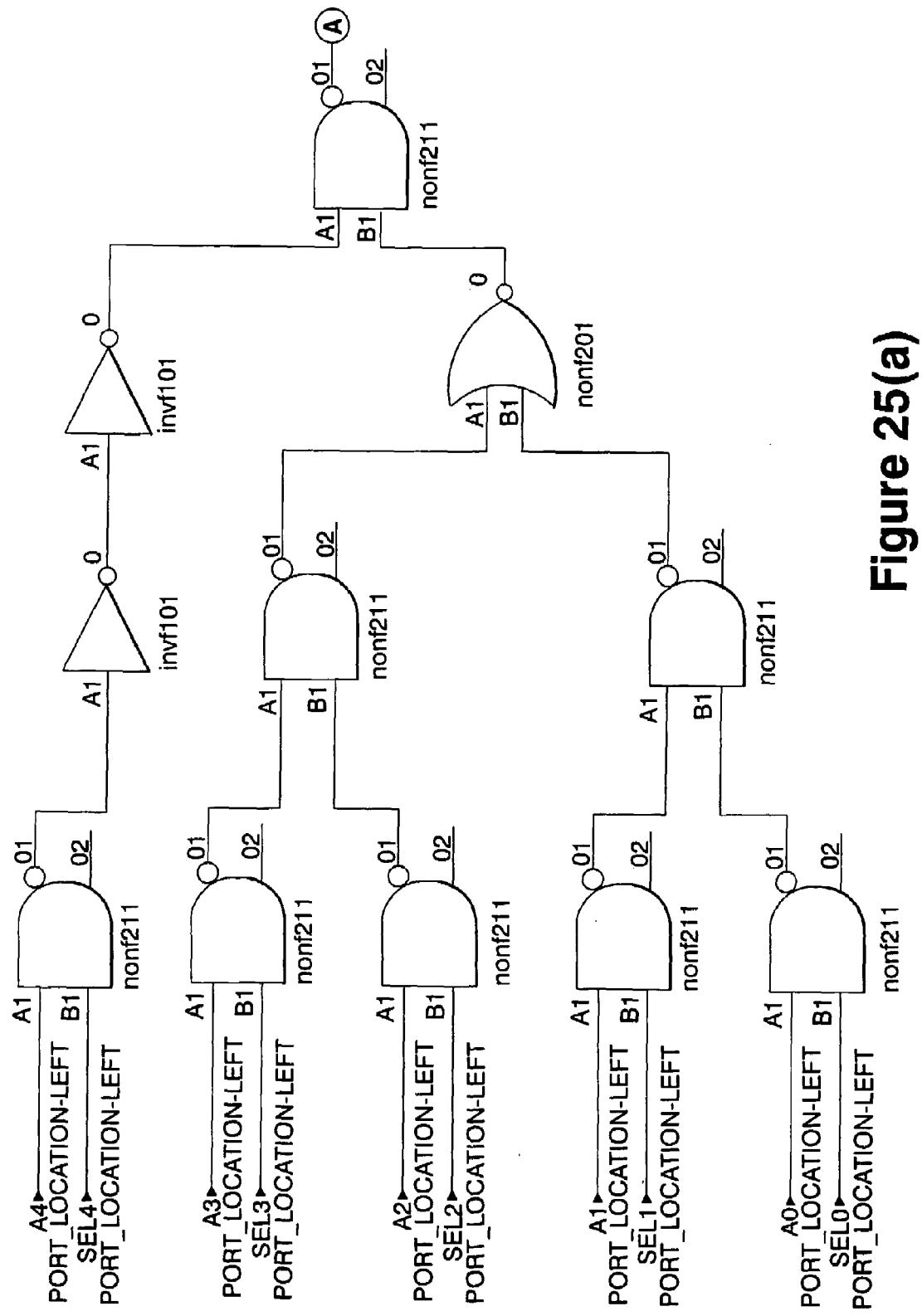
Figure 25B:
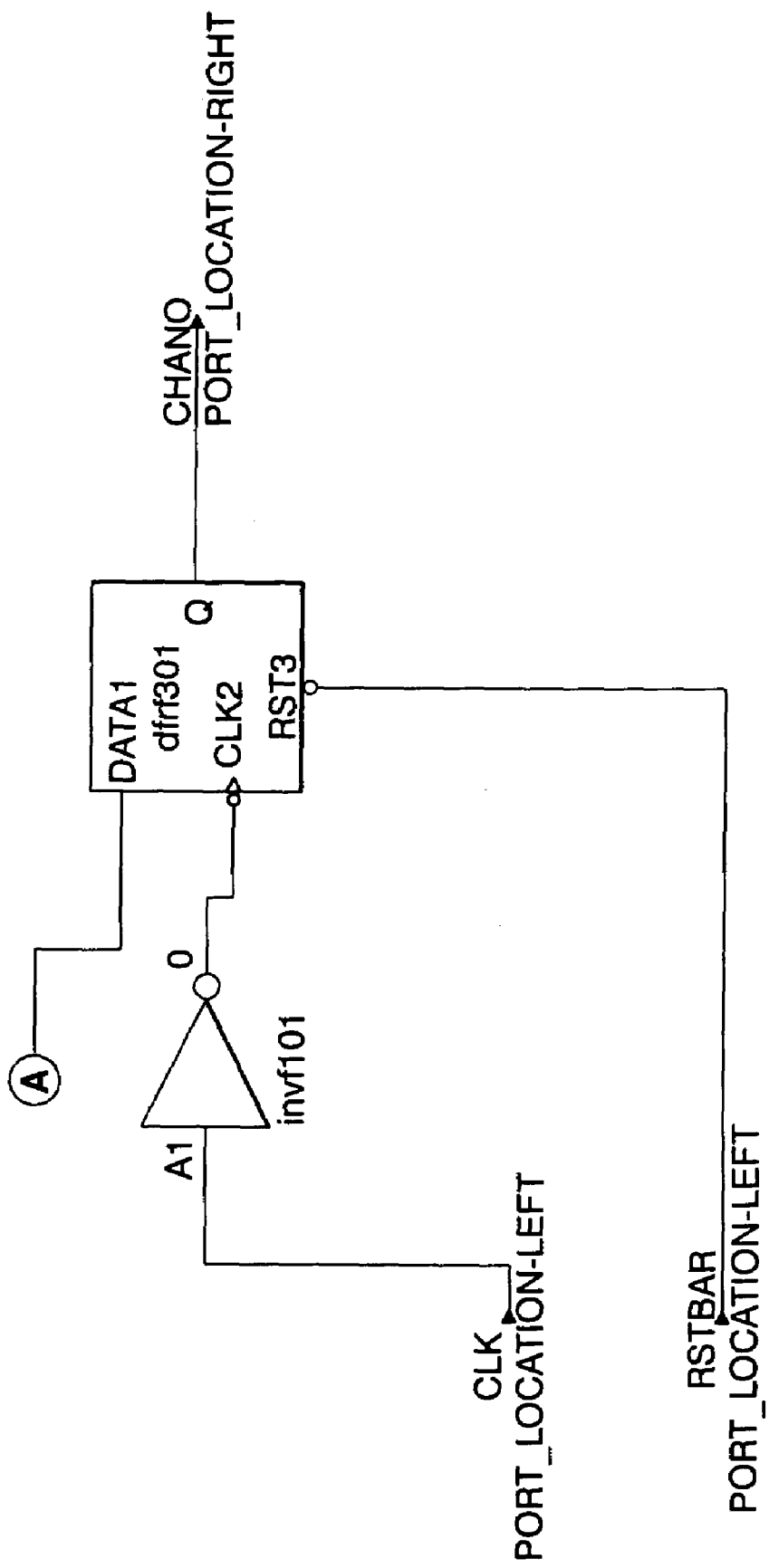
Figure 26:
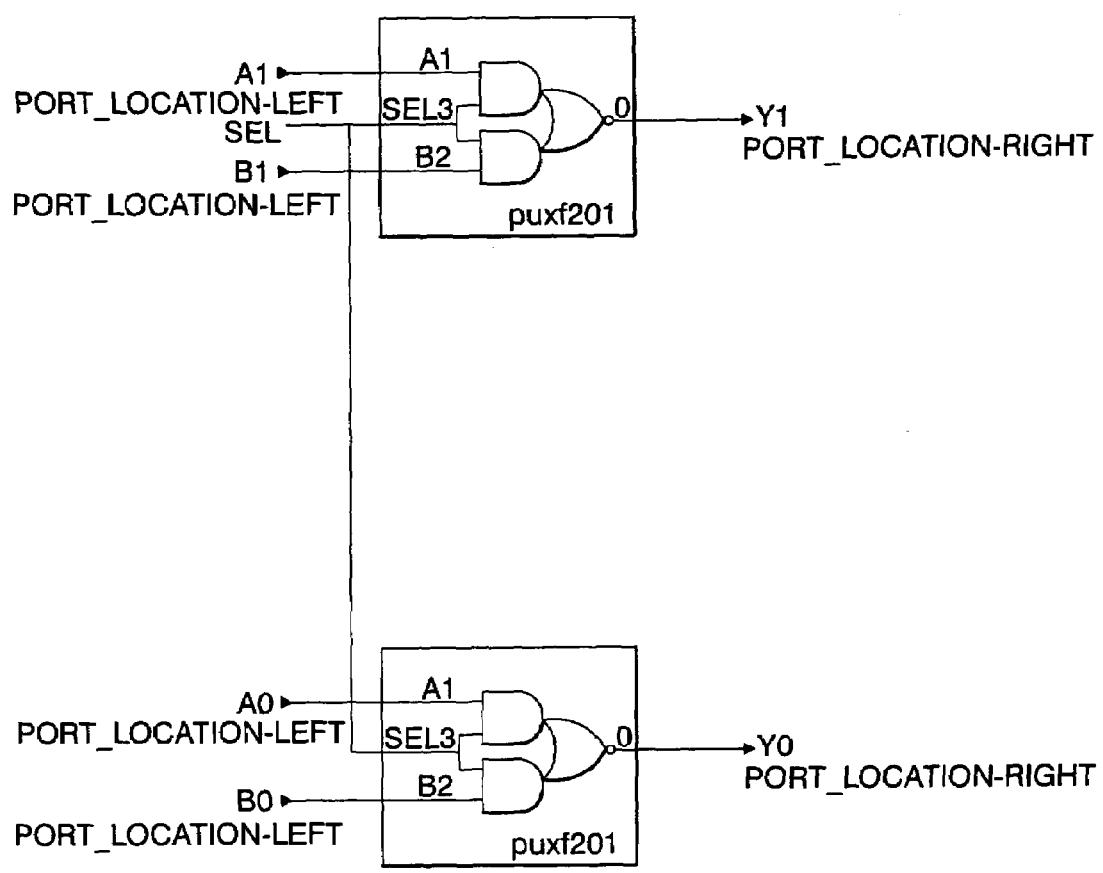
Figure 27:
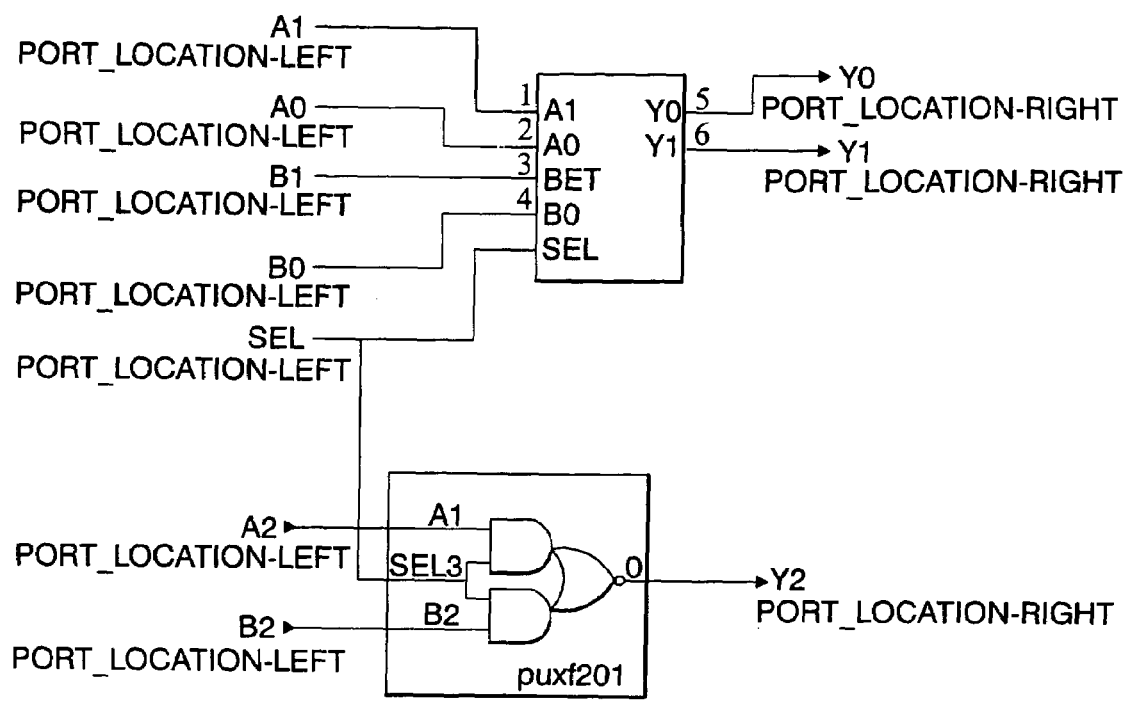
Figure 28:
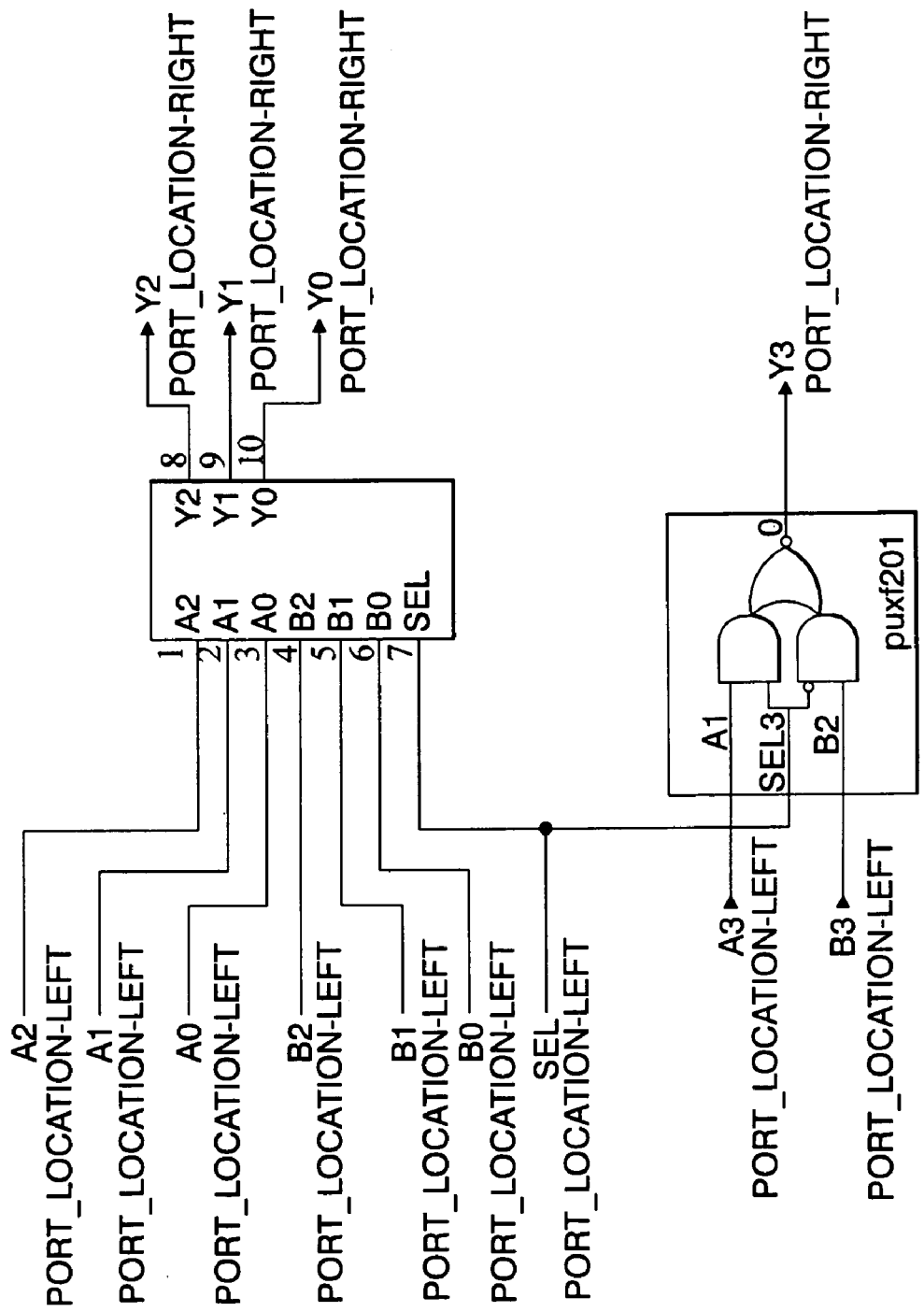
Figure 29A:
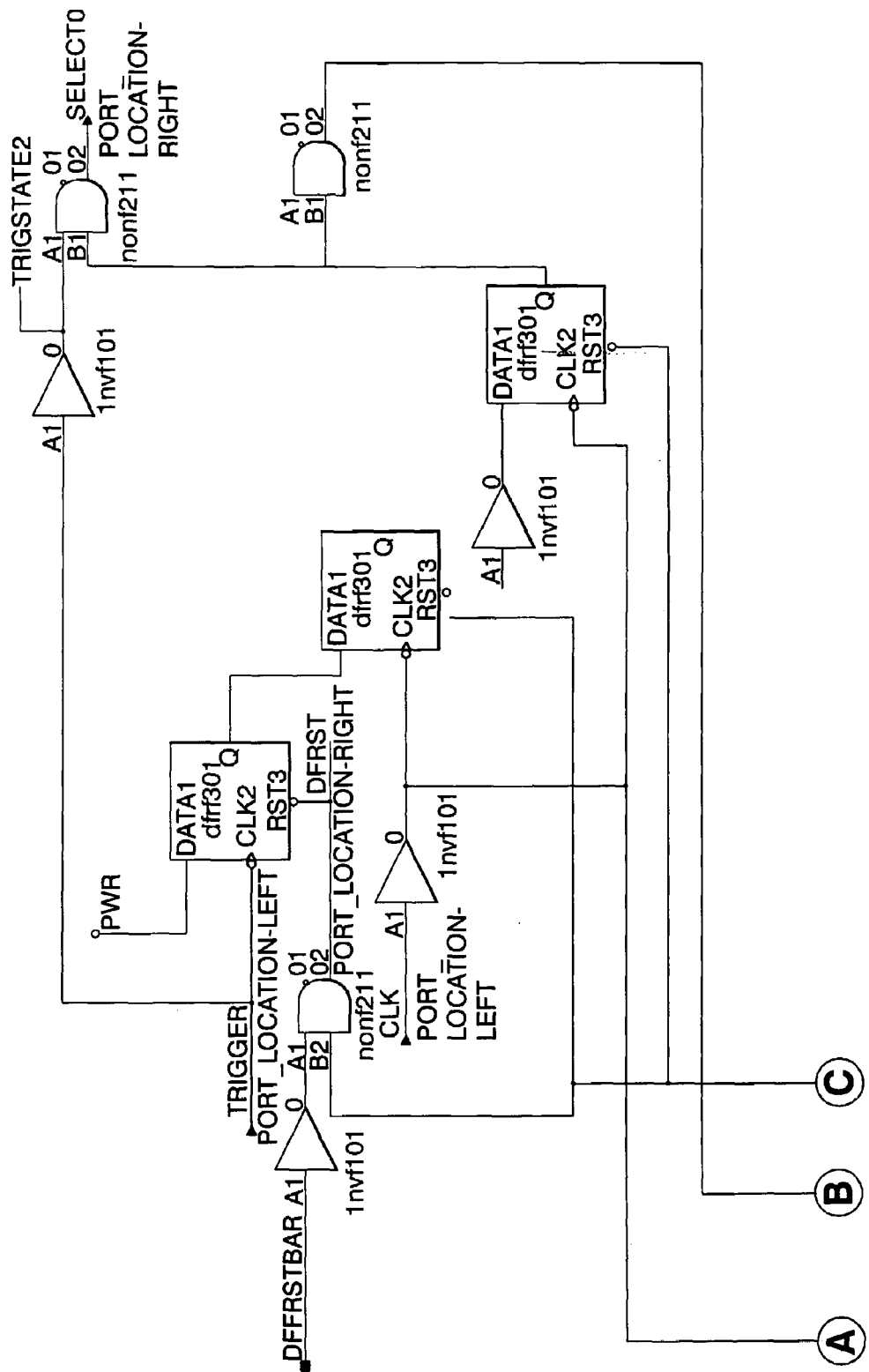
Figure 29B:
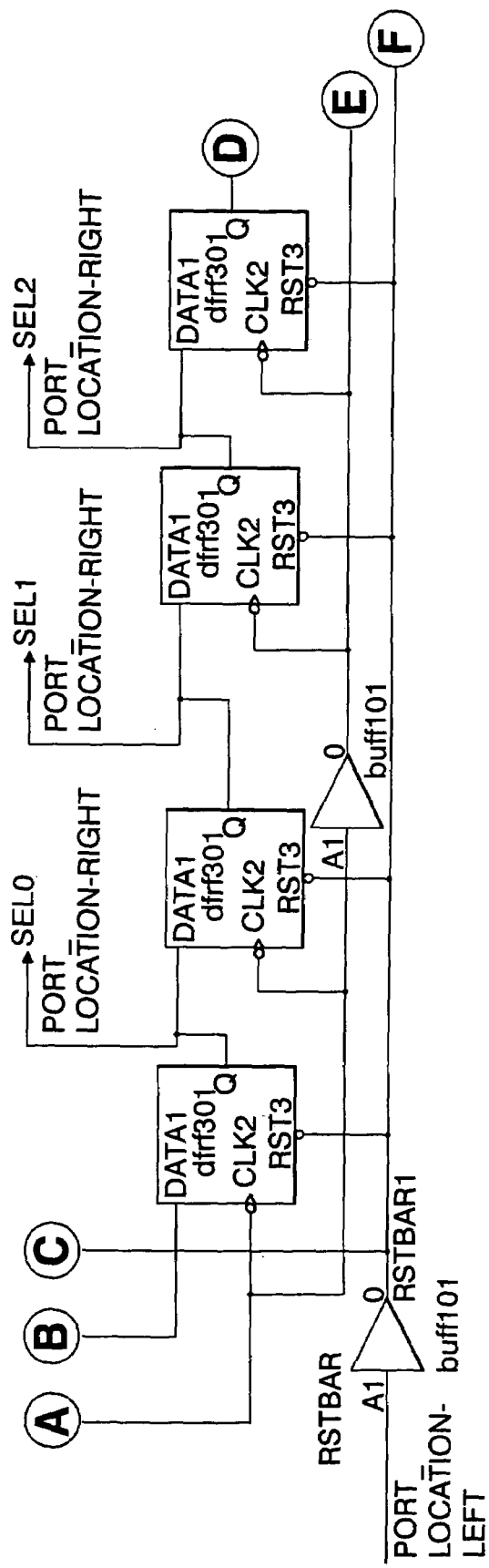
Figure 29C:
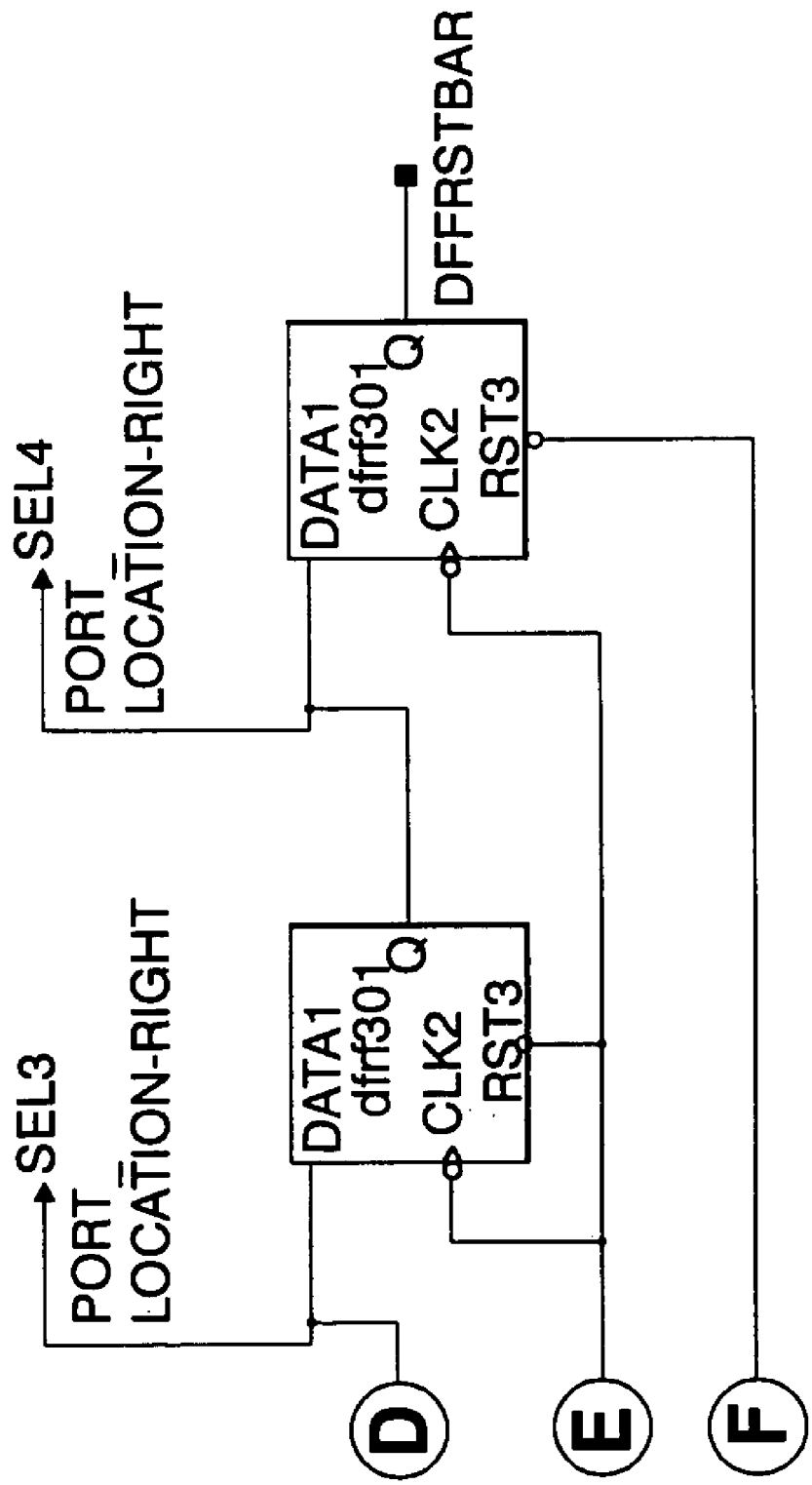

FIG. 19 is a schematic diagram showing an alternative embodiment of the edge/address/priority encoder 50 shown in FIG. 17, which may be repeated for each of the detector channels. A CFD signal 66, which includes a pulse representing the time-of-occurrence of an event is preferably applied to two (2) inverters HS5, HS6 for initial pulse shaping. The output of inverter HS6 is preferably used to asynchronously clock a high level (Vddd) through a flip-flop HS1, which provides in an edge signal 68 outputted from flip-flop HS1. The edge signal 68 is preferably synchronously clocked through two additional flip-flops HS2, HS4 and the inverted output of flip-flop HS4 is used to reset flip-flop HS1. The inverted output of flip flop HS2 and the inverted output of flip flop HS1 are preferably applied to the inputs of a nor gate HS30, the output of which is used as a load signal 70 for a shift register (HS34, HS33, HS36, HS37, HS38).

In the embodiment shown in FIG. 19 the channel address is preferably provided as a 5-bit digital quantity. Each of the A inputs of multiplexed flip flops HS34, HS33, HS36, HS37, HS38 is preferably connected to a high level (Vddd) or a low level (Vssd) to represent corresponding bits of the channel address. For instance, if the channel address is defined by bits A0–A4 (A0 being the least significant bit) then a binary channel address of 11101 is represented by connecting the A input of flip flop HS37 to a low level and connecting the A inputs of the remaining flip flops HS34, HS33, HS36, HS38 to a high level, as shown in FIG. 19.

The load signal 70 is preferably an active high pulse having a duration of about one period of the system clock signal 54. When the load signal 70 is high, the A inputs of each of the multiplexed flip flops HS34, HS33, HS36, HS37, HS38 are loaded into the corresponding flip flop. When the load signal 70 is low, the flip-flops HS34, HS33, HS36, HS37, HS38 function as a 5-bit serial shift register, the output of which is a channel address signal 72. The channel address signal 72 is combined with the edge signal 68 using a nor gate HS35 and inverters HS39, HS40, HS41 to yield an edge/address signal 74.

A timing diagram of these signals is provided in FIG. 15, which shows that the edge/address signal 74 is a combination of asynchronous analog information representing the time-of-occurrence of an event by the position of an edge, as well as synchronous digital information representing the address of the particular channel that detected the event. The combination of this information permits a single serial data link 33 to be shared by each of the channels in a detector block or each of the channels in the detector ring formed in accordance with the present invention.

FIGS. 20–29 are schematic diagrams of an alternative embodiment of the N-channel serial encoder 64 shown in FIG. 18, in which N=32. These diagrams were prepared in contemplation of an ASIC implementation of the encoder 64, which essentially incorporates the encoder circuitry shown in FIG. 19 for each of the 32 channels, as well as circuitry to combine the outputs of each of the channel encoder circuits into a single serial output signal 52 shown in FIG. 18 and a priority encoder to resolve busy link conditions. The ASIC is preferably designed to have minimal power dissipation so as not to affect the gain of the APD detector array, which is sensitive to temperature.

FIG. 19a is a schematic diagram of a preferred embodiment, which is implemented in an ASIC, of the serial encoding circuitry shown in FIG. 19. The preferred embodiment is similar to that shown in FIG. 19, except that a single shift register 67 is used to serialize the addresses for each of the channels in the ASIC. The channel address A0–A4 is preferably generated by a 32-to-5 priority encoder, such as an encoder 39 shown in FIG. 20.

An asynchronous trigger signal 71, which represents the time-of-occurrence of an annihilation event, is preferably applied to a time signal generator 73. A serializing signal 75, which is a synchronous derivative of the trigger signal 71, propagates through the shift register 67 to generate enabling signals Select0–Select4. The enabling signals Selecte0–Select4 gate successive bits of the channel address through combinatorial logic 77 to a flip flop 79 that outputs the serialized channel address signal 72.

Figure 30:
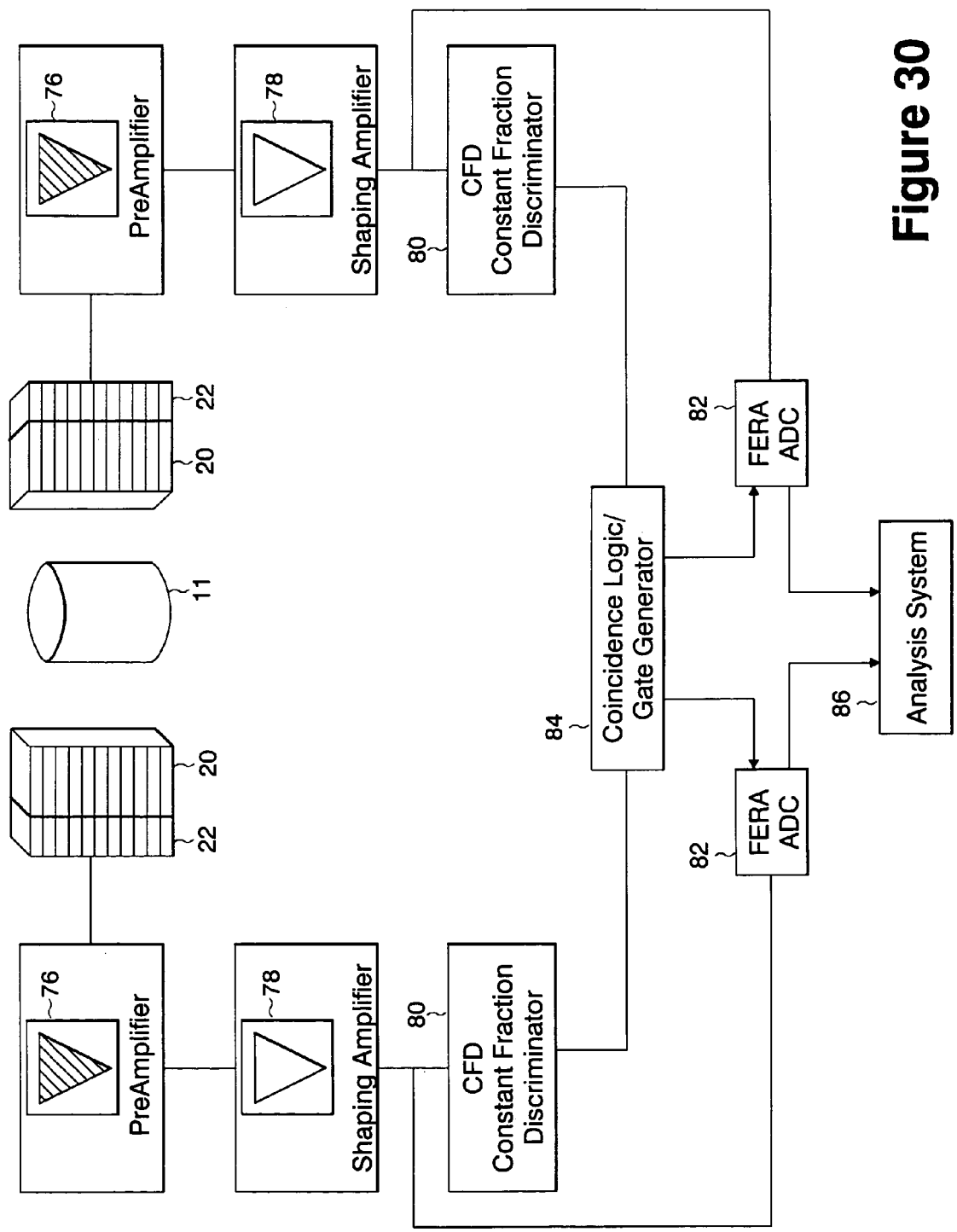
FIG. 30 is a block diagram of an experimental measurement setup for use in collecting sample data for simulated reconstructions in accordance with the present invention.

An experimental measurement setup to measure system sensitivity and resolution is shown in FIG. 30, which is not intended to represent the preferred embodiment of the invention. In FIG. 30, signals from the APD detector array 22 are preferably inputted into a charge sensitive preamplifier 76 and then into shaping amplifiers 78 with about a 70 ns peaking time. The output of the shaping amplifiers 78 are then preferably divided between constant fraction discriminators (CFD) 80 with about a 50 mV threshold and Computer Automated Measurement and Control Fast Encoding and Readout analog-to-digital converters (CAMAC FERA ADC) 82 that digitize these signals. A Nuclear Instrumentation Methods (NIM) logic unit or coincidence logic/gate generator 84 preferably selects coincidence events and generates a gate for the ADCs 82. Data are preferably transferred from the ADCs 82 and analyzed in an external system 86.

Sensitivity of the APD detector array 22 is preferably determined using a known level of radioactivity in a 2 mm line source 11. An estimate of this sensitivity is also preferably calculated for the volume of radioactivity in the field of view of the detectors 22, which is about 0.05 cm3, and compared to the measured value. The measured value is about 0.10 Hz/nCi. The count rate is typically low with this sensitivity, but is preferably increased by integrating over several seconds. It should be noted that the described sensitivity relates to a single pair of detectors that are about 10 mm deep. The sensitivity is preferably enhanced by increasing the quantity of detectors in the array and/or the depth of the LSO crystal arrays 20.

An energy resolution study is preferably performed using the APD detector array 22. The energy resolution is preferably sufficient to clearly delineate a 511 keV signal from the background. LSO crystal arrays 20, which are available from Proteus, Inc., are preferably used in the experiment.

LSO crystal arrays 20 available from CTI provide a signal of about 2500 primary photoelectrons per MeV and an energy resolution of about 23% Full Width Half Maximum (FWHM) for 511 keV gamma rays. Two configurations were tested using the LSO crystal arrays 20 available from Proteus, each having a reflective barrier between the elements, which has excellent reflective properties and improves energy resolution. In one configuration, the reflector was bonded to the crystal surfaces, and in the other, it was not.

The bonded array provides about 2300 primary photoelectrons per MeV and an improved energy resolution of about 17%, while the unbonded surface provides about 2600 primary photoelectrons per MeV and an energy resolution of about 13%. The APD array 22 provides an average gain of about 50, which results in a signal-to-noise ratio of at least 50:1. Differences in the gain of individual channels caused a shift in the associated pulse height spectra. These differences are preferably compensated for by shifting the peak position of the photopeak in each channel to the average peak position of the thirty-two (32) channels in each array. This makes it more convenient to set a threshold such that only photopeak events are used for image reconstruction.

To determine the spatial resolution of the system, the two detector arrays 22 are preferably rotated around various source phantoms 11 to simulate the detector ring of the present invention. Data is collected and reconstructed using a filtered back projection algorithm, well-known to those skilled in the art.

Figure 32A:
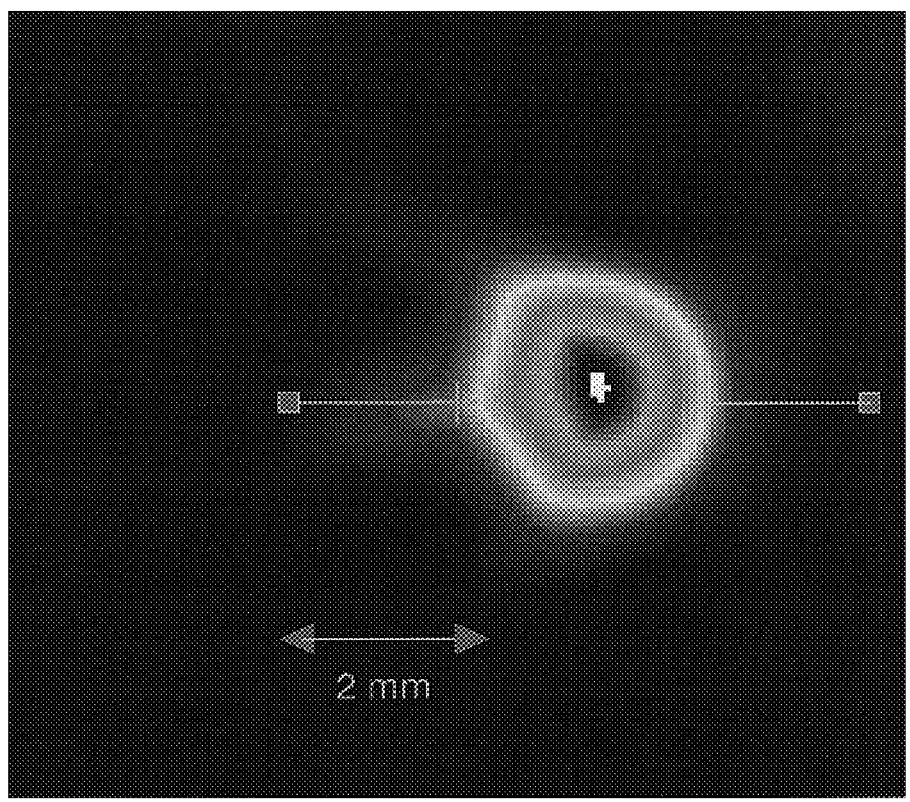
FIG. 32a is a reconstructed image of a 2 mm diameter $^{68}$Ge point source gamma emitter, measured with two gamma coincidence.
Figure 32B:
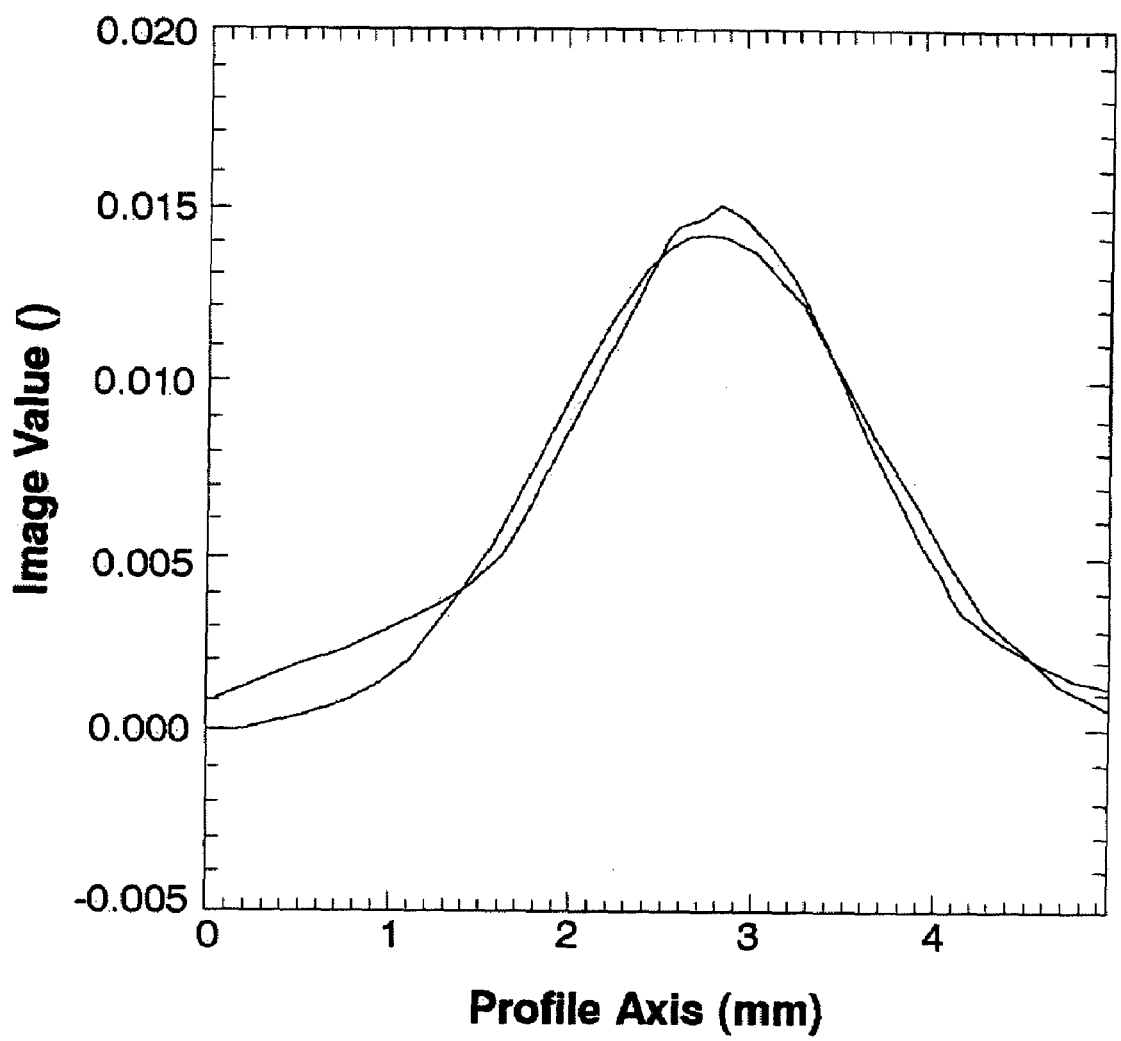

FIG. 32*a* is a reconstructed image of a 2 mm diameter $^{68}$Ge point source gamma emitter 11, measured with two gamma coincidence. Coincidence data is preferably taken by rotating the source between the two detector blocks shown in FIG. 30. Each detector block includes a 4×8 array of 2×2×10 mm LSO crystals coupled via a UV-transparent silicone wafer to a geometrically matched 4×8 APD array. An intensity profile through the center of the reconstructed image, shown in FIG. 32*b*, reveals a full width half maximum (FWHM) spatial resolution of 2.1 mm, in good agreement with simulation results.

Simulations can more readily allow prediction of the resolution across the entire field of view. The SimSET Monte Carlo package is described in K. Lewellen, R. L. Harrison, and S. Vannoy, *The SimSET program*, Monte Carlo Calculations in Nuclear Medicine, Medical Science Series, M. Liungberg, S.-E. Strand, and M. A. King, Eds., "Bristol. Institute of Physics Publishing", pp. 77–92 (1998), which is incorporated herein by reference. The package is modified to accept a discrete-crystal annulus geometry closely approximating the conscious animal PET formed in accordance with the present invention.

Point sources are generated over a range of radii, and the data binned into direct-plane sinograms, which are normalized and then reconstructed using filtered backprojection.

Figure 33:
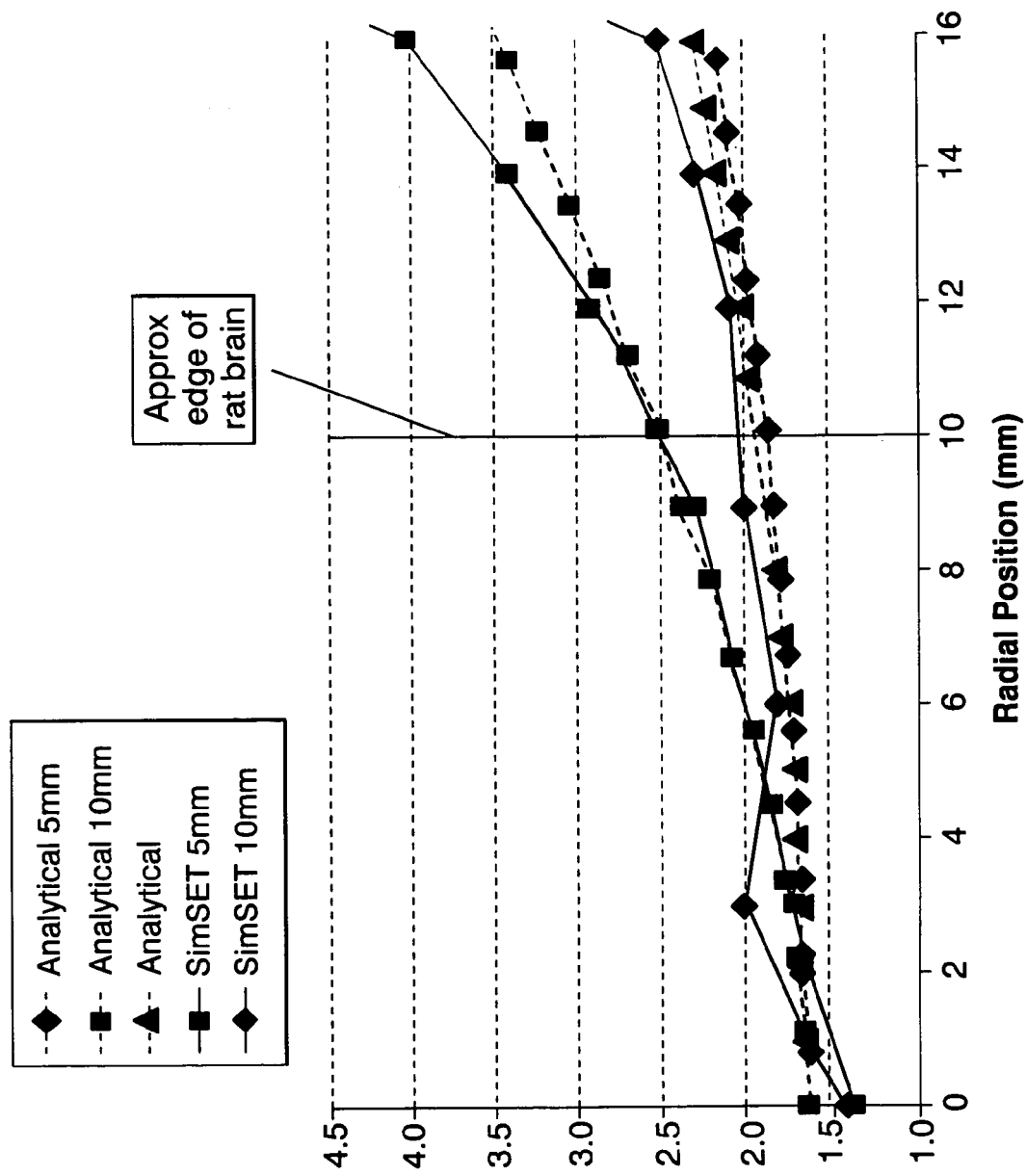
FIG. 33 is a graph of spatial resolution of the tomograph for simulations generated for 5 and 10 mm crystal lengths, which also incorporates the analytical results from FIG. 10.

The resolutions for simulations generated for 5 and 10 mm crystal lengths are shown in FIG. 33, which also includes the analytical results plotted in FIG. 10. The 5 mm length is preferred in the present invention to maintain resolution better than 2 mm throughout the brain at the expense of sensitivity. Alternate embodiments have been described above.

In yet another embodiment, side shielding, especially on the body side of the scanner, is preferably added to the detector ring. A modified version of SimSET is preferably used to model this embodiment in order to optimize the tradeoff between added weight, and acceptance of randoms and scatter from outside the field of view.

In the conscious animal PET formed in accordance with the present invention, the gap between the detectors results in an irregular sampling of the object. The gap degrades the reconstructed images by creating zero efficiency sonogram bins that can not be normalized. This leads to artifacts in the filtered backprojection image. SimSET is used along with measurements to predict and correct the effect of undersampling, thereby improving image quality, preferably by interpolating data into these empty bins from adjacent bins.

Figure 34A:
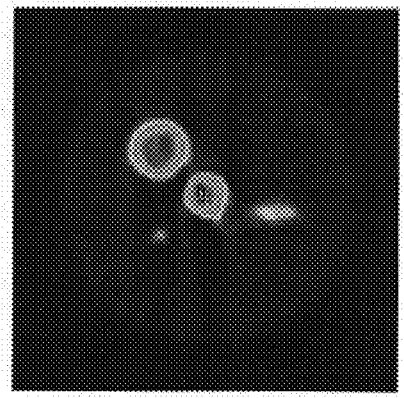
FIG. 34a is a fully sampled reconstructed image of four circular point sources with different positions within the FOV.
Figure 34B:
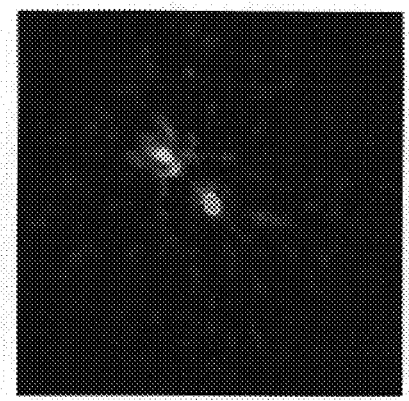
FIG. 34b is a reconstructed image of the same four circular point sources from an undersampled data set.
Figure 34C:
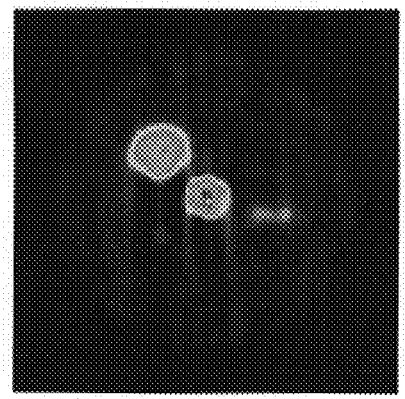
FIG. 34c is a reconstructed image from the undersampled data of FIG. 34b, using interpolation.

FIG. 34*a* shows a fully sampled reconstructed image of four circular point sources with different positions within the FOV. FIG. 34*b* shows the reconstructed image of the same four circular point sources from an undersampled data set. FIG. 34*c* shows the affect of preferably interpolating data into the empty bins on a reconstruction of the undersampled data set of FIG. 34*b*, using SimSET. Interpolation provides significant improvement in image quality in the compact conscious animal PET of the present invention.

SimSET is also preferably used to improve image quality using depth of interaction (DOI) information to correct for parallax errors.

Noise in the electronics and readout system of the conscious animal PET scanner represents a major limitation to timing resolution. Therefore, the Application Specific Integrated Circuit (ASIC) shown in FIGS. 4, 6, and 20–27 is preferably substituted for discrete devices on the detector ring. The ASIC preferably uses 0.18 μm Complementary Metal Oxide Semiconductor (CMOS) technology and is about 1.5×4.2 mm$^2$.

Substitution of the ASIC significantly improves timing resolution. Current experimental data indicate a resolution of about 5 nanoseconds FWHM for the detector without the ASIC. FIG. 31 is a graph representing the timing resolution or Root Mean Square (RMS) zero crossing jitter from the conscious animal PET with the ASIC formed in accordance with the present invention.

As indicated in FIG. 31, for about 1000–2000 photoelectrons produced with a gain of 50 in the APD detector array and a shaping time of about 70 nanoseconds, the timing resolution is about 1 nanosecond. Therefore, with a coincidence timing resolution of about 1 to 2 nanoseconds, much of the interference generated from random noise during acquisition of the input function can be eliminated.

As shown in FIG. 17, the ASIC preferably includes access to analog signals, which are preferably brought off the chip and used externally to measure energy. As shown in FIGS. 17 and 18, the preferred embodiment of the conscious animal PET scanner includes a zero crossing discriminator (ZCD) or constant fraction discriminator (CFD) per channel and the data is transferred over a serial link from the ASIC on the detector ring to a TDC near or on the animal cage. The TDC preferably adds a time stamp and sends the time-of-occurrence and channel address to a remote coincidence processor, as shown in FIG. 13. A Versa Module Europa (VME) system is preferably used to increase the data transfer capability from the detectors to the remote coincidence processor. The VME bus preferably includes a TTL-based backplane which, although the system is asynchronous, sets the data transfer speed to about 20 Mbytes per second.

In addition to reducing complexity, size and expense, the implementation of the ASIC advantageously minimizes the power dissipated on the detector ring, to avoid injury or discomfort to the animal under test. The power dissipated is about 2.6 mW per channel on the ring, and about 3 to 10 Watts at the TDC on the cage.

The conscious animal PET scanner of the present invention is used in the preferred embodiment, to image the brain of a conscious small animal, preferably a rat. The PET scanner may also be worn over a long period of time and used to study, for example, human disease, cancer, efficiency of pharmaceutical drugs, and the effects of drug addiction.

To study brain activity of a rat, for example, glucose is chemically tagged with a radioactive isotope and injected into the rat. The chemically tagged glucose becomes a tracer for brain activity, which is monitored by the head-mounted PET while the rat performs experimental tasks or reacts to different stimuli.

The pharmacokinetics of a pharmaceutical drug can be studied by radioactively tagging the drug of interest and administering it to an animal and/or human by injection or inhalation. Absorption of the drug and its effect on the brain can then be imaged by the conscious animal PET scanner of the present invention, over time, without the deleterious influence of anesthesia on the image data.

Stress on the animal is reduced by the implementation of the suspension support stand, which also allows the conscious animal PET to be worn continuously for long periods of time. The sequential brain images can be directly correlated, since no image shifting occurs.

Thus, the conscious animal PET scanner formed in accordance with the present invention may be used to monitor brain activity of a conscious animal, by attaching to the head or body of a small animal. The counterweighted tether and the lightweight, low power consumption, and compact design of the detector ring allow the conscious animal freedom of movement to perform experimental tasks during monitoring.

In addition, PET images may be acquired on an animal without the need to administer anesthesia, which profoundly disturbs the neurological state of the animal and complicates interpretation of the results. A further advantage of the present invention is the minimization of animal stress during conscious imaging.

The conscious animal PET formed in accordance with the present invention is the first wearable tomograph. Therefore, a further advantage of the present invention is that collective movement of the head and body is allowed while maintaining a fixed position of the tomograph relative to the brain. This results in zero motion within the field of view with a completely awake animal, standard data processing, and lower material cost.

A further advantage of the PET scanner of the present invention is that it can function within the high magnetic fields of a Magnetic Resonance Imaging (MRI) scanner, and therefore allows simultaneous PET and MRI imaging. Such capability is invaluable for simultaneously imaging both structural and physiological information over a long period of time.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention. Those variations include, but are not limited to, a wearable PET scanner adapted to mounting to other areas of the body, and to other animals, as well as to humans.

The invention claimed is:

1. A method of transferring annihilation information from a block comprising N detector channels in a conscious animal positron emission tomography (PET) scanner used to image a portion of a conscious animal, where N is an integer greater than one, an nth detector channel corresponding to a physical location of an nth detector on the block, comprising the steps of:

inputting a jth time pulse on an nth detector channel, the nth detector channel being one of the N detector channels, the jth time pulse comprising a jth position in time, corresponding to a time-of-occurrence of a jth event, j being an integer from 1 to J, J representing a total number of events recorded on the block;

generating a jth time signal, the jth time signal representing a time-of-occurrence of the jth time pulse, the jth time pulse being asynchronous to a clock signal;

generating a jth address signal, the jth address signal comprising an nth address, the nth address representing the nth detector channel recording the jth event, the jth address signal being synchronous to the clock signal;

generating a jth detector channel signal, the jth detector channel signal comprising the jth time signal and the jth address signal;

generating a composite signal, the composite signal comprising at least one of the J detector channel signals from at least one of the N detector channels; and outputting the composite signal serially over a data link.

2. A method of transferring annihilation information from a block comprising N detector channels in a conscious animal positron emission tomography (PET) scanner used to image a portion of a conscious animal, where N is an integer greater than one, an nth detector channel corresponding to a physical location of an nth detector on the block, as defined by claim 1, further comprising the step of adapting the method for use in obtaining an image of a conscious animal brain.

3. A method of transferring annihilation information from a block comprising N detector channels in a conscious animal positron emission tomography (PET) scanner used to image a portion of a conscious animal, where N is an integer greater than one, an nth detector channel corresponding to a physical location of an nth detector on the block, as defined by claim 1, further comprising the steps of:

inputting jth energy information on the nth detector channel, the jth energy information representing an energy content of the jth event;

generating a jth energy signal, the jth energy signal comprising a jth energy pulse, the jth energy pulse comprising a position representing the jth energy information, the jth energy pulse being asynchronous to the clock signal; and incorporating the jth energy signal in the jth detector channel signal.

4. A method of transferring annihilation information from a block comprising N detector channels in a conscious animal positron emission tomography (PET) scanner used to image a portion of a conscious animal, where N is an integer greater than one, an nth detector channel corresponding to a physical location of an nth detector on the block, as defined by claim 1, further comprising the step of incorporating a synchronous delay between the jth time signal and the jth address signal.

5. A method of transferring annihilation information from a block comprising N detector channels in a conscious animal positron emission tomography (PET) scanner used to image a portion of a conscious animal, where N is an integer greater than one, an nth detector channel corresponding to a physical location of an nth detector on the block, as defined by claim 1, wherein the jth detector channel signal comprises a jth packet comprising information representing the jth time signal and the jth address signal, further comprising the step of determining a duration of the packet $T_{packet}$ in accordance with the following equation:

$$T_{packet} = (\log_2(N)+2) * T_{clock} \qquad (1),$$

N representing a quantity of detector channels, $T_{clock}$ representing a period of the clock signal.

6. A method of transferring annihilation information from a block comprising N detector channels in a conscious animal positron emission tomography (PET) scanner used to image a portion of a conscious animal, where N is an integer greater than one, an nth detector channel corresponding to a physical location of an nth detector on the block, as defined by claim 1, wherein the jth detector channel signal comprises a jth packet comprising information representing the jth time signal and the jth address signal, the method further comprising the step of determining a duration of the packet $T_{packet}$ in accordance with the following equation:

$$T_{packet} \lll 1/(N*\text{rate}) \qquad (2),$$

N representing a quantity of detector channels, rate representing an average event rate per detector channel.

7. A method of transferring annihilation information from a block comprising N detector channels in a conscious animal positron emission tomography (PET) scanner used to image a portion of a conscious animal, where N is an integer greater than one, an nth detector channel corresponding to a physical location of an nth detector on the block, as defined by claim 1, further comprising the steps of:

inputting a (j+1)th time pulse, the (j+1)th time pulse comprising a position representing a time-of-occurrence of a (j+1)th event, the time-of-occurrence of the (j+1)th event being substantially the same as the time-of-occurrence of the jth event; and disregarding one of the jth event and the (j+1)th event in accordance with a priority scheme.

8. A method of transferring annihilation information from a block comprising N detector channels in a conscious animal positron emission tomography (PET) scanner used to image a portion of a conscious animal, where N is an integer greater than one, an nth detector channel corresponding to a physical location of an nth detector on the block, as defined by claim 7, wherein the priority scheme includes the step of disregarding one of the jth event and the (j+1)th event associated with a lower channel address.

9. An apparatus to serially transfer annihilation information in a conscious animal positron emission tomography (PET) scanner used to image a portion of a conscious animal, the apparatus comprising:

at least one pair of opposing blocks, each block of the at least one pair of opposing blocks comprising N detector channels, an nth detector channel being one of the N detector channels and corresponding to a physical location of an nth detector on the block, each block of the at least one pair of opposing blocks comprising:

an nth time signal generator associated with the nth detector channel, a jth time pulse being input to the nth time signal generator on the nth detector channel, the jth time pulse comprising a position representing a time-of-occurrence of a jth event, the nth time signal generator generating a jth time signal, the jth time signal representing a time-of-occurrence of the jth time pulse, the jth time pulse being asynchronous to a clock signal, j being an integer from 1 to J, J representing a total number of events recorded on the block;

an address signal generator generating an nth address representing the nth detector channel at which the jth event is recorded, the address signal generator generating a jth address signal, the jth address signal comprising the nth address representing the nth detector channel at which the jth event occurred, the jth address signal being synchronous to the clock signal; and a detector channel signal generator, generating a jth detector channel signal, the jth detector channel signal comprising the jth time signal and the jth address signal, and outputting a composite signal serially over a data link, the composite signal comprising at least one of the J detector channel signals from at least one of the N detector channels.

10. An apparatus to serially transfer annihilation information in a conscious animal positron emission tomography (PET) scanner used to image a portion of a conscious animal, as defined by claim 9, wherein the apparatus is adapted for use in obtaining PET images of an animal brain.

11. An apparatus to serially transfer annihilation information in a conscious animal positron emission tomography (PET) scanner used to image a portion of a conscious animal, as defined by claim 9, further comprising an energy signal generator, the energy signal generator inputting jth energy information on the nth detector channel, the jth energy information comprising an energy content of the jth event, the energy signal generator generating a jth energy signal, the jth energy signal comprising a jth energy pulse, the jth energy pulse comprising a position representing the jth energy information, the jth energy pulse being asynchronous to the clock signal, the detector channel signal generator incorporating the jth energy signal in the jth detector channel signal.

12. An apparatus to serially transfer annihilation information in a conscious animal positron emission tomography (PET) scanner used to image a portion of a conscious animal, as defined by claim 9, wherein the detector channel signal generator incorporates a synchronous delay between the jth time signal and the jth address signal.

13. An apparatus to serially transfer annihilation information in a conscious animal positron emission tomography (PET) scanner used to image a portion of a conscious animal, as defined by claim 9, wherein the detector channel signal generator generates a jth packet, the jth packet comprising information representing the jth time signal and the jth address signal, the detector channel signal generator determining a duration of the packet $T_{packet}$ in accordance with the following equation:

$$T_{packet} = (\log_2(N)+2) * T_{clock} \qquad (1),$$

N representing a quantity of channels, $T_{clock}$ representing a period of the clock signal.

14. An apparatus to serially transfer annihilation information in a conscious animal positron emission tomography (PET) scanner used to image a portion of a conscious animal, as defined by claim 9, wherein the detector channel signal generator determines a duration of the packet $T_{packet}$ in accordance with the following equation:

$$T_{packet} \lll 1/(N*\text{rate}) \qquad (2),$$

N representing a quantity of channels, rate representing an average rate of events per detector channel.

15. An apparatus to serially transfer annihilation information in a conscious animal positron emission tomography (PET) scanner used to image a portion of a conscious animal, as defined by claim 9, further comprising:
a priority encoder, the priority encoder disregarding one of the jth event and a (j+1)th event, the time-of-occurrence of the jth event being substantially the same as the time-of-occurrence of the (j+1)th event.

16. An apparatus to serially transfer annihilation information in a conscious animal positron emission tomography (PET) scanner used to image a portion of a conscious animal, as defined by claim 15, wherein the priority encoder disregards one of the jth event and the (j+1)th event associated with a lower channel address.

17. An apparatus to serially transfer annihilation information in a conscious animal positron emission tomography (PET) scanner used to image a portion of a conscious animal, as defined by claim 9, wherein the apparatus is adapted for implementation in an Application Specific Integrated Circuit (ASIC).

18. An apparatus to serially transfer annihilation information in a conscious animal positron emission tomography (PET) scanner used to image a portion of a conscious animal, as defined by claim 9, wherein the nth time signal generator comprises a flip-flop, the flip flop being clocked by the jth time pulse, the flip flop outputting the jth time signal.

19. An apparatus to serially transfer annihilation information in a conscious animal positron emission tomography (PET) scanner used to image a portion of a conscious animal, as defined by claim 9, wherein the address signal generator comprises a shift register, the shift register being loaded with the nth address in response to the jth time signal, the shift register being clocked by the clock signal.

20. An apparatus to serially transfer annihilation information in a conscious animal positron emission tomography (PET) scanner used to image a portion of a conscious animal, as defined by claim 9, wherein the detector channel signal generator comprises combinatorial logic, the combinatorial logic incorporating the jth time signal and the jth address signal in the jth detector channel signal.

21. A compact conscious animal positron emission tomography (PET) scanner for acquiring images of a portion of a conscious animal, comprising:
a ring tomograph, the ring tomograph comprising an inner surface, the inner surface mounting onto and substantially surrounding the portion of the conscious animal, at least one block pair, at least one of the at least one block pair comprising a first block and a second block, the second block being positioned opposite the first block on the ring tomograph, each of the first block and the second block comprising:
a scintillator layer, the scintillator layer outputting at least one photon in response to a jth event, the jth event being one of a total of J events recorded on the each of the first block and the second block;
a detection array, the detection array comprising N detectors, the nth detector being one the N detectors in the detection array, the nth detector being associated with an nth detector channel, the nth detector outputting a jth detection signal in response to detecting the at least one photon corresponding to the jth event;
a front-end array, the front end array comprising N front ends, the nth front end being one of the N front ends in the front end array, the nth front end being associated with the nth detector channel, the nth front end outputting a jth time pulse in response to receiving the jth detection signal;
a serial encoder comprising:
N time signal generators, the nth time signal generator inputting the jth time pulse on the nth detector channel, the nth detector channel being one of the N detector channels, the jth time pulse comprising a position representing a time-of-occurrence of the jth event, the nth time signal generator generating a jth time signal, the jth time signal representing a time-of-occurrence of the jth time pulse, the jth time pulse being asynchronous to a clock signal;
an address signal generator, the address signal generator generating an nth address, the nth address representing the nth detector channel at which the jth event is recorded, the address signal generator generating a jth address signal, the jth address signal comprising the nth address representing the nth detector channel at which the jth event is recorded, the jth address signal being synchronous to the clock signal; and
a detector channel signal generator, the detector channel signal generator generating a jth detector channel signal, the jth detector channel signal comprising the jth time signal and the jth address signal, the detector channel signal generator serially outputting at least one of the detector channel signals from at least one of the N detector channels.

22. A compact conscious animal positron emission tomography (PET) scanner for acquiring images of a portion of a conscious animal as defined in claim 21, wherein at least one of the N front ends further comprises at least one of a preamplifier, a shaper network, a zero-crossing detector, and a constant fraction discriminator.

23. A compact conscious animal positron emission tomography (PET) scanner for acquiring images of a portion of a conscious animal as defined in claim 21, wherein the scanner is adapted for use in obtaining PET images of an animal brain.

24. A compact conscious animal positron emission tomography (PET) scanner for acquiring images of a portion of a conscious animal as defined in claim 23, wherein the animal brain is a rat brain.

25. A compact conscious animal positron emission tomography (PET) scanner for acquiring images of a portion of a conscious animal as defined in claim 21, wherein the serial encoder further comprises N energy signal generators, the nth energy signal generator inputting jth energy information on the nth detector channel, the jth energy information comprising an energy content of the jth event, the nth energy signal generator generating a jth energy signal, the jth energy signal comprising a jth energy pulse, the jth energy pulse comprising a position representing the jth energy information, the jth energy pulse being asynchronous to the clock signal, the detector channel signal generator incorporating the jth energy signal in the jth detector channel signal.

26. A compact conscious animal positron emission tomography (PET) scanner for acquiring images of a portion of a conscious animal as defined in claim 21, wherein the detector channel signal generator generates a jth packet, the jth packet comprising information representing the jth time signal and the jth address signal, the detector channel signal generator determining a duration of the packet $T_{packet}$ in accordance with the following equation:

$$T_{packet} \lll 1/(N^*\text{rate}) \qquad (2),$$

N representing a quantity of channels, rate representing an average rate of events per detector channel.

27. A compact conscious animal positron emission tomography (PET) scanner for acquiring images of a portion of a conscious animal as defined in claim 21, wherein the serial encoder further comprises a priority encoder, the time-of-occurrence of the jth event being substantially the same as the time-of-occurrence of a (j+1)th event, the priority encoder disregarding one of the jth event and the (j+1)th event in accordance with a priority scheme.

28. A compact conscious animal positron emission tomography (PET) scanner for acquiring images of a portion of a conscious animal as defined in claim 27, wherein the priority scheme includes the step of disregarding one of the jth event and the (j+1)th event associated with a lower address.

29. A compact conscious animal positron emission tomography (PET) scanner for acquiring a portion of a conscious animal as defined in claim 21, wherein the front-end array and the serial encoder are adapted for implementation in an Application Specific Integrated Circuit (ASIC).

30. A compact conscious animal positron emission tomography (PET) scanner for acquiring images of a portion of a conscious animal as defined in claim 21, wherein the scintillator layer comprises a scintillator array, the scintillator array comprising N crystals, the nth crystal being one of a plurality of the N crystals in the scintillator array, the nth crystal being associated with the nth detector channel, the nth crystal outputting at least one photon in response to receiving gamma radiation from a jth event.

31. A compact conscious animal positron emission tomography (PET) scanner for acquiring images of a portion of a conscious animal as defined in claim 30, wherein the scintillator array comprises lutetium oxyorthosilicate (LSO) and the detection array comprises avalanche photodiodes (APD).

32. A compact conscious animal positron emission tomography (PET) scanner for acquiring images of a portion of a conscious animal as defined in claim 21, wherein each of the first block and the second block comprises a second detection array, the scintillator layer comprising a solid block of lutetium oxyorthosilicate (LSO), the solid block of LSO comprising a first LSO surface and a second LSO surface, the detection array being substantially adjacent to the first LSO surface, the second detection array being substantially adjacent to the second LSO surface.

33. A compact conscious animal positron emission tomography (PET) scanner for acquiring images of a portion of a conscious animal as defined in claim 30, each of the first block and the second block further comprising a second detection array and a second scintillator array.

* * * * *

UNITED STATES PATENT AND TRADEMARK OFFICE
CERTIFICATE OF CORRECTION

PATENT NO.        : 7,126,126 B2                                                   Page 1 of 1
APPLICATION NO. : 10/687797
DATED             : October 24, 2006
INVENTOR(S)       : David J. Schlyer et al.

It is certified that error appears in the above-identified patent and that said Letters Patent is hereby corrected as shown below:

On The Title Page, Item (75) Inventors; First inventor should read

--David J. Schlyer--.

Signed and Sealed this

Thirtieth Day of January, 2007

JON W. DUDAS
*Director of the United States Patent and Trademark Office*